(12) United States Patent
Konzak et al.

(10) Patent No.: US 10,570,411 B2
(45) Date of Patent: Feb. 25, 2020

(54) WHEAT PLANTS HAVING INCREASED TOLERANCE TO IMIDAZOLINONE HERBICIDES

(71) Applicants: BASF SE, Ludwigshafen (DE); Agrigenetics, Inc., Indianapolis, IN (US)

(72) Inventors: Calvin Konzak, Pullman, WA (US); Iwona Birk, Raleigh, NC (US); Bijay Singh, Cary, NC (US)

(73) Assignees: BASF Aktiengesellschaft, Ludwigshafen (DE); Agrigenetics Inc., Midland, MI (US)

( * ) Notice: Subject to any disclaimer, the term of this patent is extended or adjusted under 35 U.S.C. 154(b) by 441 days.

(21) Appl. No.: 15/199,016

(22) Filed: Jun. 30, 2016

(65) Prior Publication Data

US 2016/0376605 A1    Dec. 29, 2016

Related U.S. Application Data

(62) Division of application No. 10/559,161, filed as application No. PCT/EP2004/005222 on May 14, 2004, now Pat. No. 9,382,526.

(60) Provisional application No. 60/473,828, filed on May 28, 2003.

(51) Int. Cl.
C12N 15/82     (2006.01)
A01H 5/10      (2018.01)
C12Q 1/6895    (2018.01)

(52) U.S. Cl.
CPC ........... *C12N 15/8274* (2013.01); *A01H 5/10* (2013.01); *C12N 15/8278* (2013.01); *C12Q 1/6895* (2013.01); *C12Y 401/03* (2013.01)

(58) Field of Classification Search
CPC .................................................. A01H 6/4678
See application file for complete search history.

(56) References Cited

U.S. PATENT DOCUMENTS 7,829,762 B2 *  11/2010  Bowran ................... A01H 5/10
                                                    800/260

* cited by examiner

*Primary Examiner* — David H Kruse

(74) *Attorney, Agent, or Firm* — Lowenstein Sander LLP

(57) ABSTRACT

The present invention is directed to wheat plants and triticale plants having increased tolerance to an imidazolinone herbicide. More particularly, the present invention includes wheat plants or triticale plants containing one or more *Triticum turgidum* IMI nucleic acids. The present invention also includes seeds produced by these wheat plants and triticale plants, and methods of controlling weeds in the vicinity of these wheat plants and triticale plants.

16 Claims, 23 Drawing Sheets

Specification includes a Sequence Listing.

FIG.1A

```
                         1                                                50
Utopia_Als2     (1)   TCCCCCGCCGCCACCTCCGCCGCGCCTCCCGCCACCGCGCTCCGGCCGTG
Ciccio_Als2     (1)   TCCCCCGCCGCCACCTCCGCCGCGCCTCCCGCCACCGCGCTCCGGCCGTG
Colosseo_Als2   (1)   TCCCCCGCCGCCACCTCCGCCGCGCCTCCCGCCACCGCGCTCCGGCCGTG
Consensus       (1)   TCCCCCGCCGCCACCTCCGCCGCGCCTCCCGCCACCGCGCTCCGGCCGTG 51                                               100
Utopia_Als2     (51)  GGGCCCCTCCGAGCCCCGTAAGGGCGCCGACATCCTCGTCGAGGCGCTGG
Ciccio_Als2     (51)  GGGCCCCTCCGAGCCCCGTAAGGGCGCCGACATCCTCGTCGAGGCGCTGG
Colosseo_Als2   (51)  GGGCCCCTCCGAGCCCCGTAAGGGCGCCGACATCCTCGTCGAGGCGCTGG
Consensus       (51)  GGGCCCCTCCGAGCCCCGTAAGGGCGCCGACATCCTCGTCGAGGCGCTGG 101                                              150
Utopia_Als2     (101) AGCGCTGCGGCATCGTCGACGTCTTCGCCTACCCTGGCGGCGCGTCCATG
Ciccio_Als2     (101) AGCGCTGCGGCATCGTCGACGTCTTCGCCTACCCTGGCGGCGCGTCCATG
Colosseo_Als2   (101) AGCGCTGCGGCATCGTCGACGTCTTCGCCTACCCTGGCGGCGCGTCCATG
Consensus       (101) AGCGCTGCGGCATCGTCGACGTCTTCGCCTACCCTGGCGGCGCGTCCATG 151                                              200
Utopia_Als2     (151) GAGATCCACCAGGCGCTGACGCGCTCGCCAGTCATCACCAACCACCTCTT
Ciccio_Als2     (151) GAGATCCACCAGGCGCTGACGCGCTCGCCAGTCATCACCAACCACCTCTT
Colosseo_Als2   (151) GAGATCCACCAGGCGCTGACGCGCTCGCCAGTCATCACCAACCACCTCTT
Consensus       (151) GAGATCCACCAGGCGCTGACGCGCTCGCCAGTCATCACCAACCACCTCTT 201                                              250
Utopia_Als2     (201) CCGCCACGAGCAGGGGAGGCGTTCGCGGCGTCCGGGTACGCCCGCGCGT
Ciccio_Als2     (201) CCGCCACGAGCAGGGGAGGCGTTCGCGGCGTCCGGGTACGCCCGCGCGT
Colosseo_Als2   (201) CCGCCACGAGCAGGGGAGGCGTTCGCGGCGTCCGGGTACGCCCGCGCGT
Consensus       (201) CCGCCACGAGCAGGGGAGGCGTTCGCGGCGTCCGGGTACGCCCGCGCGT 251                                              300
Utopia_Als2     (251) CCGGCCGCGTCGGCGTCTGCGTCGCCACCTCCGGCCCGGGGGCCACCAAC
Ciccio_Als2     (251) CCGGCCGCGTCGGCGTCTGCGTCGCCACCTCCGGCCCGGGGGCCACCAAC
Colosseo_Als2   (251) CCGGCCGCGTCGGCGTCTGCGTCGCCACCTCCGGCCCGGGGGCCACCAAC
Consensus       (251) CCGGCCGCGTCGGCGTCTGCGTCGCCACCTCCGGCCCGGGGGCCACCAAC 301                                              350
Utopia_Als2     (301) CTCGTCTCCGCGCTCGCCGACGCTCTCCTCGACTCCATCCCCATGGTCGC
Ciccio_Als2     (301) CTCGTCTCCGCGCTCGCCGACGCTCTCCTCGACTCCATCCCCATGGTCGC
Colosseo_Als2   (301) CTCGTCTCCGCGCTCGCCGACGCTCTCCTCGACTCCATCCCCATGGTCGC
Consensus       (301) CTCGTCTCCGCGCTCGCCGACGCTCTCCTCGACTCCATCCCCATGGTCGC 351                                              400
Utopia_Als2     (351) CATCACGGGCCAGGTCCCCGCCGCATGATCGGCACGGATGCGTTCCAGG
Ciccio_Als2     (351) CATCACGGGCCAGGTCCCCGCCGCATGATCGGCACGGATGCGTTCCAGG
Colosseo_Als2   (351) CATCACGGGCCAGGTCCCCGCCGCATGATCGGCACGGATGCGTTCCAGG
Consensus       (351) CATCACGGGCCAGGTCCCCGCCGCATGATCGGCACGGATGCGTTCCAGG 401                                              450
Utopia_Als2     (401) AGACGCCCATCGTGGAGGTCACGCGCTCCATCACCAAGCACAACTACCTG
Ciccio_Als2     (401) AGACGCCCATCGTGGAGGTCACGCGCTCCATCACCAAGCACAACTACCTG
Colosseo_Als2   (401) AGACGCCCATCGTGGAGGTCACGCGCTCCATCACCAAGCACAACTACCTG
Consensus       (401) AGACGCCCATCGTGGAGGTCACGCGCTCCATCACCAAGCACAACTACCTG
```

FIG.1B

```
                      451                                                500
Utopia_Als2    (451)  GTCCTTGACGTGGAGGATATCCCCCGCGTCATCCAGGAAGCCTTCTTCCT
Ciccio_Als2    (451)  GTCCTTGACGTGGAGGATATCCCCCGCGTCATCCAGGAAGCCTTCTTCCT
Colosseo_Als2  (451)  GTCCTTGACGTGGAGGATATCCCCCGCGTCATCCAGGAAGCCTTCTTCCT
Consensus      (451)  GTCCTTGACGTGGAGGATATCCCCCGCGTCATCCAGGAAGCCTTCTTCCT 501                                                550
Utopia_Als2    (501)  CGCATCCTCTGGCCGCCCGGGGCCGGTGCTCCTTGATATCCCCAAGGACA
Ciccio_Als2    (501)  CGCATCCTCTGGCCGCCCGGGGCCGGTGCTGGTTGATATCCCCAAGGACA
Colosseo_Als2  (501)  CGCATCCTCTGGCCGCCCGGGGCCGGTGCTGGTTGATATCCCCAAGGACA
Consensus      (501)  CGCATCCTCTGGCCGCCCGGGGCCGGTGCTGGTTGATATCCCCAAGGACA 551                                                600
Utopia_Als2    (551)  TCCAGCAGCAGATGGCTGTGCCTGTCTGGGACACGCCGATGAGTTTGCCA
Ciccio_Als2    (551)  TCCAGCAGCAGATGGCTGTGCCTGTCTGGGACACGCCGATGAGTTTGCCA
Colosseo_Als2  (551)  TCCAGCAGCAGATGGCTGTGCCTGTCTGGGACACGCCGATGAGTTTGCCA
Consensus      (551)  TCCAGCAGCAGATGGCTGTGCCTGTCTGGGACACGCCGATGAGTTTGCCA 601                                                650
Utopia_Als2    (601)  GGGTACATCGCCCGCCTGCCCAAGCCACCATCTACTGAATCGCTTGAGCA
Ciccio_Als2    (601)  GGGTACATCGCCCGCCTGCCCAAGCCACCATCTACTGAATCGCTTGAGCA
Colosseo_Als2  (601)  GGGTACATCGCCCGCCTGCCCAAGCCACCATCTACTGAATCGCTTGAGCA
Consensus      (601)  GGGTACATCGCCCGCCTGCCCAAGCCACCATCTACTGAATCGCTTGAGCA 651                                                700
Utopia_Als2    (651)  GGTCCTGCGTCTGGTTGGCGAGTCACGGCGCCCAATTCTGTATGTTGGTG
Ciccio_Als2    (651)  GGTCCTGCGTCTGGTTGGCGAGTCACGGCGCCCAATTCTGTATGTTGGTG
Colosseo_Als2  (651)  GGTCCTGCGTCTGGTTGGCGAGTCACGGCGCCCAATTCTGTATGTTGGTG
Consensus      (651)  GGTCCTGCGTCTGGTTGGCGAGTCACGGCGCCCAATTCTGTATGTTGGTG 701                                                750
Utopia_Als2    (701)  GTGGCTGCGCTGCATCTGGTGAGGAGTTGCGCCGCTTTGTTGAGCTCACT
Ciccio_Als2    (701)  GTGGCTGCGCTGCATCTGGTGAGGAGTTGCGCCGCTTTGTTGAGCTCACT
Colosseo_Als2  (701)  GTGGCTGCGCTGCATCTGGTGAGGAGTTGCGCCGCTTTGTTGAGCTCACT
Consensus      (701)  GTGGCTGCGCTGCATCTGGTGAGGAGTTGCGCCGCTTTGTTGAGCTCACT 751                                                800
Utopia_Als2    (751)  GGGATTCCAGTTACAACTACTCTTATGGGCCTTGGCAACTTCCCCAGTGA
Ciccio_Als2    (751)  GGGATTCCAGTTACAACTACTCTTATGGGCCTTGGCAACTTCCCCAGTGA
Colosseo_Als2  (751)  GGGATTCCAGTTACAACTACTCTTATGGGCCTTGGCAACTTCCCCAGTGA
Consensus      (751)  GGGATTCCAGTTACAACTACTCTTATGGGCCTTGGCAACTTCCCCAGTGA 801                                                850
Utopia_Als2    (801)  CGACCCACTGTCTCTGCGCATGCTGGGGATGCATGGCACTGTGTATGCAA
Ciccio_Als2    (801)  CGACCCACTGTCTCTGCGCATGCTGGGGATGCATGGCACTGTGTATGCAA
Colosseo_Als2  (801)  CGACCCACTGTCTCTGCGCATGCTGGGGATGCATGGCACTGTGTATGCAA
Consensus      (801)  CGACCCACTGTCTCTGCGCATGCTGGGGATGCATGGCACTGTGTATGCAA 851                                                900
Utopia_Als2    (851)  ATTATGCAGTAGATAAGGCTGACCTGTTGCTTGCATTTGGTGTGCGGTTT
Ciccio_Als2    (851)  ATTATGCAGTAGATAAGGCTGACCTGTTGCTTGCATTTGGTGTGCGGTTT
Colosseo_Als2  (851)  ATTATGCAGTAGATAAGGCTGACCTGTTGCTTGCATTTGGTGTGCGGTTT
Consensus      (851)  ATTATGCAGTAGATAAGGCTGACCTGTTGCTTGCATTTGGTGTGCGGTTT
```

FIG.1C

```
                            901                                              950
Utopia_Als2    ( 901) GATGATCGTGTGACCGGGAAAATCGAGGCTTTTGCAAGCAGGTCCAAGAT
Ciccio_Als2    ( 901) GATGATCGTGTGACCGGGAAAATCGAGGCTTTTGCAAGCAGGTCCAAGAT
Colosseo_Als2  ( 901) GATGATCGTGTGACCGGGAAAATCGAGGCTTTTGCAAGCAGGTCCAAGAT
    Consensus  ( 901) GATGATCGTGTGACCGGGAAAATCGAGGCTTTTGCAAGCAGGTCCAAGAT 951                                             1000
Utopia_Als2    ( 951) TGTGCACATTGACATTGACCCAGCTGAGATTGGCAAGAACAAGCAGCCAC
Ciccio_Als2    ( 951) TGTGCACATTGACATTGACCCAGCTGAGATTGGCAAGAACAAGCAGCCAC
Colosseo_Als2  ( 951) TGTGCACATTGACATTGACCCAGCTGAGATTGGCAAGAACAAGCAGCCAC
    Consensus  ( 951) TGTGCACATTGACATTGACCCAGCTGAGATTGGCAAGAACAAGCAGCCAC 1001                                             1050
Utopia_Als2    (1001) ATGTCTCCATTTGTGCAGATGTTAAGCTTGCTTTACAGGGGTTGAATGCT
Ciccio_Als2    (1001) ATGTCTCCATTTGTGCAGATGTTAAGCTTGCTTTACAGGGGTTGAATGCT
Colosseo_Als2  (1001) ATGTCTCCATTTGTGCAGATGTTAAGCTTGCTTTACAGGGGTTGAATGCT
    Consensus  (1001) ATGTCTCCATTTGTGCAGATGTTAAGCTTGCTTTACAGGGGTTGAATGCT 1051                                             1100
Utopia_Als2    (1051) CTATTAAATGGGAGCAAAGCACAACAGGGTCTGGATTTTGGTCCATGGCA
Ciccio_Als2    (1051) CTATTAAATGGGAGCAAAGCACAACAGGGTCTGGATTTTGGTCCATGGCA
Colosseo_Als2  (1051) CTATTAAATGGGAGCAAAGCACAACAGGGTCTGGATTTTGGTCCATGGCA
    Consensus  (1051) CTATTAAATGGGAGCAAAGCACAACAGGGTCTGGATTTTGGTCCATGGCA 1101                                             1150
Utopia_Als2    (1101) CAAGGAGTTGGATCAGCAGAAGAGGGAGTTTCCTCTAGGATTCAAGACTT
Ciccio_Als2    (1101) CAAGGAGTTGGATCAGCAGAAGAGGGAGTTTCCTCTAGGATTCAAGACTT
Colosseo_Als2  (1101) CAAGGAGTTGGATCAGCAGAAGAGGGAGTTTCCTCTAGGATTCAAGACTT
    Consensus  (1101) CAAGGAGTTGGATCAGCAGAAGAGGGAGTTTCCTCTAGGATTCAAGACTT 1151                                             1200
Utopia_Als2    (1151) TTGGTGAGGCCATCCCGCCGCAATATGCTATCCAGGTACTGGATGAGCTG
Ciccio_Als2    (1151) TTGGTGAGGCCATCCCGCCGCAATATGCTATCCAGGTACTGGATGAGCTG
Colosseo_Als2  (1151) TTGGTGAGGCCATCCCGCCGCAATATGCTATCCAGGTACTGGATGAGCTG
    Consensus  (1151) TTGGTGAGGCCATCCCGCCGCAATATGCTATCCAGGTACTGGATGAGCTG 1201                                             1250
Utopia_Als2    (1201) ACAAAAGGGGAGGCGATCATTGCCACCGGTGTTGGGCAGCATCAGATGTG
Ciccio_Als2    (1201) ACAAAAGGGGAGGCGATCATTGCCACCGGTGTTGGGCAGCATCAGATGTG
Colosseo_Als2  (1201) ACAAAAGGGGAGGCGATCATTGCCACCGGTGTTGGGCAGCATCAGATGTG
    Consensus  (1201) ACAAAAGGGGAGGCGATCATTGCCACCGGTGTTGGGCAGCATCAGATGTG 1251                                             1300
Utopia_Als2    (1251) GGCGGCTCAGTATTACACTTACAAGCGGCCACGGCAGTGGCTGTCTTCGT
Ciccio_Als2    (1251) GGCGGCTCAGTATTACACTTACAAGCGGCCACGGCAGTGGCTGTCTTCGT
Colosseo_Als2  (1251) GGCGGCTCAGTATTACACTTACAAGCGGCCACGGCAGTGGCTGTCTTCGT
    Consensus  (1251) GGCGGCTCAGTATTACACTTACAAGCGGCCACGGCAGTGGCTGTCTTCGT 1301                                             1350
Utopia_Als2    (1301) CCGGTTTGGGTGCAATGGGATTTGGGTTGCCAGCTGCAGCTGGCGCTGCT
Ciccio_Als2    (1301) CCGGTTTGGGTGCAATGGGATTTGGGTTGCCAGCTGCAGCTGGCGCTGCT
Colosseo_Als2  (1301) CCGGTTTGGGTGCAATGGGATTTGGGTTGCCAGCTGCAGCTGGCGCTGCT
    Consensus  (1301) CCGGTTTGGGTGCAATGGGATTTGGGTTGCCAGCTGCAGCTGGCGCTGCT
```

FIG.1D

```
                              1351                                              1400
Utopia_Als2    (1351)  GTGGCCAACCCAGGTGTTACAGTTGTTGACATTGATGGGGATGGTAGTTT
Ciccio_Als2    (1351)  GTGGCCAACCCAGGTGTTACAGTTGTTGACATTGATGGGGATGGTAGTTT
Colosseo_Als2  (1351)  GTGGCCAACCCAGGTGTTACAGTTGTTGACATTGATGGGGATGGTAGTTT
Consensus      (1351)  GTGGCCAACCCAGGTGTTACAGTTGTTGACATTGATGGGGATGGTAGTTT 1401                                              1450
Utopia_Als2    (1401)  CCTCATGAACATTCAGGAGTTGCCGTTGATCCGTATTGAGAACCTCCCAG
Ciccio_Als2    (1401)  CCTCATGAACATTCAGGAGTTGGCGTTGATCCGTATTGAGAACCTCCCAG
Colosseo_Als2  (1401)  CCTCATGAACATTCAGGAGTTGGCGTTGATCCGTATTGAGAACCTCCCAG
Consensus      (1401)  CCTCATGAACATTCAGGAGTTGGCGTTGATCCGTATTGAGAACCTCCCAG 1451                                              1500
Utopia_Als2    (1451)  TGAAGGTGATGATATTGAACAACCAGCATCTGGGAATGGTGGTGCAGTGG
Ciccio_Als2    (1451)  TGAAGGTGATGATATTGAACAACCAGCATCTGGGAATGGTGGTGCAGTGG
Colosseo_Als2  (1451)  TGAAGGTGATGATATTGAACAACCAGCATCTGGGAATGGTGGTGCAGTGG
Consensus      (1451)  TGAAGGTGATGATATTGAACAACCAGCATCTGGGAATGGTGGTGCAGTGG 1501                                              1550
Utopia_Als2    (1501)  GAGGATAGGTTTTACAAGGCCAACCGGGCGCACACATACCTTGGCAACCC
Ciccio_Als2    (1501)  GAGGATAGGTTTTACAAGGCCAACCGGGCGCACACATACCTTGGCAACCC
Colosseo_Als2  (1501)  GAGGATAGGTTTTACAAGGCCAACCGGGCGCACACATACCTTGGCAACCC
Consensus      (1501)  GAGGATAGGTTTTACAAGGCCAACCGGGCGCACACATACCTTGGCAACCC 1551                                              1600
Utopia_Als2    (1551)  AGAAAATGAGGGTGAGATATATCCAGATTTTGTGACGATTGCTAAAGGAT
Ciccio_Als2    (1551)  AGAAAATGAGGGTGAGATATATCCAGATTTTGTGACGATTGCTAAAGGAT
Colosseo_Als2  (1551)  AGAAAATGAGGGTGAGATATATCCAGATTTTGTGACGATTGCTAAAGGAT
Consensus      (1551)  AGAAAATGAGGGTGAGATATATCCAGATTTTGTGACGATTGCTAAAGGAT 1601                                              1650
Utopia_Als2    (1601)  TCAACGTTCCGGCAGTTCGTGTGACGAAGAAGAGCGAAGTCACTGCAGCA
Ciccio_Als2    (1601)  TCAACGTTCCGGCAGTTCGTGTGACGAAGAAGAGCGAAGTCACTGCAGCA
Colosseo_Als2  (1601)  TCAACGTTCCGGCAGTTCGTGTGACGAAGAAGAGCGAAGTCACTGCAGCA
Consensus      (1601)  TCAACGTTCCGGCAGTTCGTGTGACGAAGAAGAGCGAAGTCACTGCAGCA 1651                                              1700
Utopia_Als2    (1651)  ATCAAGAAGATGCTTGAGACCCCAGGGCCATACTTGTTGGATATCATTGT
Ciccio_Als2    (1651)  ATCAAGAAGATGCTTGAGACCGCAGGGCCATACTTGTTGGATATCATTGT
Colosseo_Als2  (1651)  ATCAAGAAGATGCTTGAGACCCCAGGGCCATACTTGTTGGATATCATTGT
Consensus      (1651)  ATCAAGAAGATGCTTGAGACCCCAGGGCCATACTTGTTGGATATCATTGT 1701                                              1750
Utopia_Als2    (1701)  CCCGCATCAGGAGCACGTGCTGCCTATGATCCCAAGCGGTGGTGCTTTTA
Ciccio_Als2    (1701)  CCCGCATCAGGAGCACGTGCTGCCTATGATCCCAAGCGGTGGTGCTTTTA
Colosseo_Als2  (1701)  CCCGCATCAGGAGCACGTGCTGCCTATGATCCCAAGCGGTGGTGCTTTTA
Consensus      (1701)  CCCGCATCAGGAGCACGTGCTGCCTATGATCCCAAGCGGTGGTGCTTTTA 1751                      1788
Utopia_Als2    (1751)  AGGACATGATCATGGAGGGTGATGGCAGGACCTCGTAC
Ciccio_Als2    (1751)  AGGACATGATCATGGAGGGTGATGGCAGGACCTCGTAC
Colosseo_Als2  (1751)  AGGACATGATCATGGAGGGTGATGGCAGGACCTCGTAC
Consensus      (1751)  AGGACATGATCATGGAGGGTGATGGCAGGACCTCGTAC
```

FIG.2A

```
                          1                                                  50
Ciccio_Als3      (1)   TCCCCCGCCGCCACCTCCGCCGCGCCCCCGCCACCGCGCTCCGGCCCTG
Colosseo_Als3    (1)   TCCCCCGCCGCCACCTCCGCCGCGCCCCCGCCACCGCGCTCCGGCCCTG
Utopia_Als3      (1)   TCCCCCGCCGCCACCTCCGCCGCGCCCCCGCCACCGCGCTCCGGCCCTG
Consensus        (1)   TCCCCCGCCGCCACCTCCGCCGCGCCCCCGCCACCGCGCTCCGGCCCTG 51                                                 100
Ciccio_Als3     (51)   GGGCCCGTCCGAGCCCCGCAAGGGCGCCGACATCCTCGTCGAGGCGCTCG
Colosseo_Als3   (51)   GGGCCCGTCCGAGCCCCGCAAGGGCGCCGACATCCTCGTCGAGGCGCTCG
Utopia_Als3     (51)   GGGCCCGTCCGAGCCCCGCAAGGGCGCCGACATCCTCGTCGAGGCGCTCG
Consensus       (51)   GGGCCCGTCCGAGCCCCGCAAGGGCGCCGACATCCTCGTCGAGGCGCTCG 101                                                150
Ciccio_Als3    (101)   AGCGCTGCGGCATCGTCGACGTATTCGCCTACCCCGGCGGCGCGTCCATG
Colosseo_Als3  (101)   AGCGCTGCGGCATCGTCGACGTATTCGCCTACCCCGGCGGCGCGTCCATG
Utopia_Als3    (101)   AGCGCTGCGGCATCGTCGACGTATTCGCCTACCCCGGCGGCGCGTCCATG
Consensus      (101)   AGCGCTGCGGCATCGTCGACGTATTCGCCTACCCCGGCGGCGCGTCCATG 151                                                200
Ciccio_Als3    (151)   GAGATCCACCAGGCGCTGACGCGCTCGCCCGTCATCACCAACCACCTCTT
Colosseo_Als3  (151)   GAGATCCACCAGGCGCTGACGCGCTCGCCCGTCATCACCAACCACCTCTT
Utopia_Als3    (151)   GAGATCCACCAGGCGCTGACGCGCTCGCCCGTCATCACCAACCACCTCTT
Consensus      (151)   GAGATCCACCAGGCGCTGACGCGCTCGCCCGTCATCACCAACCACCTCTT 201                                                250
Ciccio_Als3    (201)   CCGCCACGAGCAGGGGAGGCGTTCGCGGCGTCCGGCTACGCCCGCGCGT
Colosseo_Als3  (201)   CCGCCACGAGCAGGGGAGGCGTTCGCGGCGTCCGGCTACGCCCGCGCGT
Utopia_Als3    (201)   CCGCCACGAGCAGGGGAGGCGTTCGCGGCGTCCGGCTACGCCCGCGCGT
Consensus      (201)   CCGCCACGAGCAGGGGAGGCGTTCGCGGCGTCCGGCTACGCCCGCGCGT 251                                                300
Ciccio_Als3    (251)   CCGGCCGCGTCGGCGTCTGCGTCGCCACCTCCGGCCCGGGGGCCACCAAC
Colosseo_Als3  (251)   CCGGCCGCGTCGGCGTCTGCGTCGCCACCTCCGGCCCGGGGGCCACCAAC
Utopia_Als3    (251)   CCGGCCGCGTCGGCGTCTGCGTCGCCACCTCCGGCCCGGGGGCCACCAAC
Consensus      (251)   CCGGCCGCGTCGGCGTCTGCGTCGCCACCTCCGGCCCGGGGGCCACCAAC 301                                                350
Ciccio_Als3    (301)   CTCGTCTCCGCGCTCGCTGACGCCCTCCTCGACTCCATCCCCATGGTCGC
Colosseo_Als3  (301)   CTCGTCTCCGCGCTCGCTGACGCCCTCCTCGACTCCATCCCCATGGTCGC
Utopia_Als3    (301)   CTCGTCTCCGCGCTCGCTGACGCCCTCCTCGACTCCATCCCCATGGTCGC
Consensus      (301)   CTCGTCTCCGCGCTCGCTGACGCCCTCCTCGACTCCATCCCCATGGTCGC 351                                                400
Ciccio_Als3    (351)   CATCACGGGCCAGGTCCCCCGCCGCATGATCGGCACGGACGCGTTCCAGG
Colosseo_Als3  (351)   CATCACGGGCCAGGTCCCCCGCCGCATGATCGGCACGGACGCGTTCCAGG
Utopia_Als3    (351)   CATCACGGGCCAGGTCCCCCGCCGCATGATCGGCACGGACGCGTTCCAGG
Consensus      (351)   CATCACGGGCCAGGTCCCCCGCCGCATGATCGGCACGGACGCGTTCCAGG 401                                                450
Ciccio_Als3    (401)   AGACGCCCATAGTGGAGGTCACGCGCTCCATCACCAAGCACAACTACCTG
Colosseo_Als3  (401)   AGACGCCCATAGTGGAGGTCACGCGCTCCATCACCAAGCACAACTACCTG
Utopia_Als3    (401)   AGAGGCCCATAGTGGAGGTCACGCGCTCCATCACCAAGCACAACTACCTG
Consensus      (401)   AGACGCCCATAGTGGAGGTCACGCGCTCCATCACCAAGCACAACTACCTG
```

FIG.2B

```
                           451                                                  500
  Ciccio_Als3       (451)  GTCCTTGACGTGGAGGATATCCCCCGCGTCATCCAGGAAGCCTTCTTCCT
Colosseo_Als3       (451)  GTCCTTGACGTGGAGGATATCCCCCGCGTCATCCAGGAAGCCTTCTTCCT
  Utopia_Als3       (451)  GTCCTTGACGTGGAGGATATCCCCCGCGTCATCCAGGAAGCCTTCTTCCT
    Consensus       (451)  GTCCTTGACGTGGAGGATATCCCCCGCGTCATCCAGGAAGCCTTCTTCCT 501                                                  550
  Ciccio_Als3       (501)  CGCGTCCTCTGGCCGCCCGGGGCCGGTGCTGGTTGATATCCCCAAGGATA
Colosseo_Als3       (501)  CGCGTCCTCTGGCCGCCCGGGGCCGGTGCTGGTTGATATCCCCAAGGATA
  Utopia_Als3       (501)  CGCGTCCTCTGGCCGCCCGGGGCCGGTGCTGGTTGATATCCCCAAGGATA
    Consensus       (501)  CGCGTCCTCTGGCCGCCCGGGGCCGGTGCTGGTTGATATCCCCAAGGATA 551                                                  600
  Ciccio_Als3       (551)  TCCAGCAGCAGATGGCCGTGCCTATCTGGGACACGCCGATGAGTTTGCCA
Colosseo_Als3       (551)  TCCAGCAGCAGATGGCCGTGCCTATCTGGGACACGCCGATGAGTTTGCCA
  Utopia_Als3       (551)  TCCAGCAGCAGATGGCCGTGCCTATCTGGGACACGCCGATGAGTTTGCCA
    Consensus       (551)  TCCAGCAGCAGATGGCCGTGCCTATCTGGGACACGCCGATGAGTTTGCCA 601                                                  650
  Ciccio_Als3       (601)  GGGTACATCGCCCGCCTGCCCAAGCCACCATCTACTGAATCGCTTGAGCA
Colosseo_Als3       (601)  GGGTACATCGCCCGCCTGCCCAAGCCACCATCTACTGAATCGCTTGAGCA
  Utopia_Als3       (601)  GGGTACATCGCCCGCCTGCCCAAGCCACCATCTACTGAATCGCTTGAGCA
    Consensus       (601)  GGGTACATCGCCCGCCTGCCCAAGCCACCATCTACTGAATCGCTTGAGCA 651                                                  700
  Ciccio_Als3       (651)  GGTCCTGCGTCTGGTTGGCGAGTCACGGCGCCCAATTCTGTATGTTGGTG
Colosseo_Als3       (651)  GGTCCTGCGTCTGGTTGGCGAGTCACGGCGCCCAATTCTGTATGTTGGTG
  Utopia_Als3       (651)  GGTCCTGCGTCTGGTTGGCGAGTCACGGCGCCCAATTCTGTATGTTGGTG
    Consensus       (651)  GGTCCTGCGTCTGGTTGGCGAGTCACGGCGCCCAATTCTGTATGTTGGTG 701                                                  750
  Ciccio_Als3       (701)  GTGGCTGCGCTGCATCCGGCGAGGAGTTGCGCCGCTTTGTTGAGCTCACT
Colosseo_Als3       (701)  GTGGCTGCGCTGCATCCGGCGAGGAGTTGCGCCGCTTTGTTGAGCTCACT
  Utopia_Als3       (701)  GTGGCTGCGCTGCATCCGGCGAGGAGTTGCGCCGCTTTGTTGAGCTCACT
    Consensus       (701)  GTGGCTGCGCTGCATCCGGCGAGGAGTTGCGCCGCTTTGTTGAGCTCACT 751                                                  800
  Ciccio_Als3       (751)  GGGATTCCGGTTACAACTACTCTGATGGGCCTTGGCAACTTCCCCAGCGA
Colosseo_Als3       (751)  GGGATTCCGGTTACAACTACTCTGATGGGCCTTGGCAACTTCCCCAGCGA
  Utopia_Als3       (751)  GGGATTCCGGTTACAACTACTCTGATGGGCCTTGGCAACTTCCCCAGCGA
    Consensus       (751)  GGGATTCCGGTTACAACTACTCTGATGGGCCTTGGCAACTTCCCCAGCGA 801                                                  850
  Ciccio_Als3       (801)  CGACCCACTGTCTCTGCGCATGCTTGGGATGCATGGCACTGTGTATGCAA
Colosseo_Als3       (801)  CGACCCACTGTCTCTGCGCATGCTTGGGATGCATGGCACTGTGTATGCAA
  Utopia_Als3       (801)  CGACCCACTGTCTCTGCGCATGCTTGGGATGCATGGCACTGTGTATGCAA
    Consensus       (801)  CGACCCACTGTCTCTGCGCATGCTTGGGATGCATGGCACTGTGTATGCAA 851                                                  900
  Ciccio_Als3       (851)  ATTATGCAGTCGATAAGGCTGACCTGTTGCTTGCATTTGGTGTGCGGTTT
Colosseo_Als3       (851)  ATTATGCAGTCGATAAGGCTGACCTGTTGCTTGCATTTGGTGTGCGGTTT
  Utopia_Als3       (851)  ATTATGCAGTCGATAAGGCTGACCTGTTGCTTGCATTTGGTGTGCGGTTT
    Consensus       (851)  ATTATGCAGTCGATAAGGCTGACCTGTTGCTTGCATTTGGTGTGCGGTTT
```

FIG.2C

```
                     901                                                  950
Ciccio_Als3    (901) GATGATCGCGTGACTGGGAAAATCGAGGCCTTTGCAAGCAGGTCCAAGAT
Colosseo_Als3  (901) GATGATCGCGTGACTGGGAAAATCGAGGCCTTTGCAAGCAGGTCCAAGAT
Utopia_Als3    (901) GATGATCGCGTGACTGGGAAAATCGAGGCCTTTGCAAGCAGGTCCAAGAT
Consensus      (901) GATGATCGCGTGACTGGGAAAATCGAGGCCTTTGCAAGCAGGTCCAAGAT 951                                                 1000
Ciccio_Als3    (951) TGTGCACATTGACATTGACCCAGCTGAGATTGGCAAGAACAAGCAGCCAC
Colosseo_Als3  (951) TGTGCACATTGACATTGACCCAGCTGAGATTGGCAAGAACAAGCAGCCAC
Utopia_Als3    (951) TGTGCACATTGACATTGACCCAGCTGAGATTGGCAAGAACAAGCAGCCAC
Consensus      (951) TGTGCACATTGACATTGACCCAGCTGAGATTGGCAAGAACAAGCAGCCAC 1001                                                 1050
Ciccio_Als3   (1001) ATGTCTCCATTTGTGCAGATGTTAAGCTTGCTTTACAGGGGTTGAATGCT
Colosseo_Als3 (1001) ATGTCTCCATTTGTGCAGATGTTAAGCTTGCTTTACAGGGGTTGAATGCT
Utopia_Als3   (1001) ATGTCTCCATTTGTGCAGATGTTAAGCTTGCTTTACAGGGGTTGAATGCT
Consensus     (1001) ATGTCTCCATTTGTGCAGATGTTAAGCTTGCTTTACAGGGGTTGAATGCT 1051                                                 1100
Ciccio_Als3   (1051) CTATTAAATGGGAGCAAAGCACAACAGGGTCTGGATTTTGGTCCATGGCA
Colosseo_Als3 (1051) CTATTAAATGGGAGCAAAGCACAACAGGGTCTGGATTTTGGTCCATGGCA
Utopia_Als3   (1051) CTATTAAATGGGAGCAAAGCACAACAGGGTCTGGATTTTGGTCCATGGCA
Consensus     (1051) CTATTAAATGGGAGCAAAGCACAACAGGGTCTGGATTTTGGTCCATGGCA 1101                                                 1150
Ciccio_Als3   (1101) CAAGGAGTTGGATCAGCAGAAGAGGGAGTTTCCTCTAGGATTCAAGACTT
Colosseo_Als3 (1101) CAAGGAGTTGGATCAGCAGAAGAGGGAGTTTCCTCTAGGATTCAAGACTT
Utopia_Als3   (1101) CAAGGAGTTGGATCAGCAGAAGAGGGAGTTTCCTCTAGGATTCAAGACTT
Consensus     (1101) CAAGGAGTTGGATCAGCAGAAGAGGGAGTTTCCTCTAGGATTCAAGACTT 1151                                                 1200
Ciccio_Als3   (1151) TTGGCGAGGCCATCCCGCCGCAATATGCTATCCAGGTACTGGATGAGCTG
Colosseo_Als3 (1151) TTGGCGAGGCCATCCCGCCGCAATATGCTATCCAGGTACTGGATGAGCTG
Utopia_Als3   (1151) TTGGCGAGGCCATCCCGCCGCAATATGCTATCCAGGTACTGGATGAGCTG
Consensus     (1151) TTGGCGAGGCCATCCCGCCGCAATATGCTATCCAGGTACTGGATGAGCTG 1201                                                 1250
Ciccio_Als3   (1201) ACAAAAGGGGAGGCGATCATTGCTACTGGTGTTGGGCAGCACCAGATGTG
Colosseo_Als3 (1201) ACAAAAGGGGAGGCGATCATTGCTACTGGTGTTGGGCAGCACCAGATGTG
Utopia_Als3   (1201) ACAAAAGGGGAGGCGATCATTGCTACTGGTGTTGGGCAGCACCAGATGTG
Consensus     (1201) ACAAAAGGGGAGGCGATCATTGCTACTGGTGTTGGGCAGCACCAGATGTG 1251                                                 1300
Ciccio_Als3   (1251) GGCGGCTCAGTATTACACTTACAAGCGGCCACGGCAGTGGCTGTCTTCGT
Colosseo_Als3 (1251) GGCGGCTCAGTATTACACTTACAAGCGGCCACGGCAGTGGCTGTCTTCGT
Utopia_Als3   (1251) GGCGGCTCAGTATTACACTTACAAGCGGCCACGGCAGTGGCTGTCTTCGT
Consensus     (1251) GGCGGCTCAGTATTACACTTACAAGCGGCCACGGCAGTGGCTGTCTTCGT 1301                                                 1350
Ciccio_Als3   (1301) CTGGTTTGGGGGCAATGGGATTTGGGTTACCAGCTGCAGCTGGCGCTGCT
Colosseo_Als3 (1301) CTGGTTTGGGGGCAATGGGATTTGGGTTACCAGCTGCAGCTGGCGCTGCT
Utopia_Als3   (1301) CTGGTTTGGGGGCAATGGGATTTGGGTTACCAGCTGCAGCTGGCGCTGCT
Consensus     (1301) CTGGTTTGGGGGCAATGGGATTTGGGTTACCAGCTGCAGCTGGCGCTGCT
```

FIG.2D

```
                           1351                                                1400
Ciccio_Als3    (1351)  GTGGCCAACCCAGGTGTTACAGTTGTTGACATTGATGGAGATGGTAGTTT
Colosseo_Als3  (1351)  GTGGCCAACCCAGGTGTTACAGTTGTTGACATTGATGGAGATGGTAGTTT
Utopia_Als3    (1351)  GTGGCCAACCCAGGTGTTACAGTTGTTGACATTGATGGAGATGGTAGTTT
Consensus      (1351)  GTGGCCAACCCAGGTGTTACAGTTGTTGACATTGATGGAGATGGTAGTTT 1401                                                1450
Ciccio_Als3    (1401)  CCTCATGAACATTCAGGAGTTGGCATTGATCCGTATTGAGAACCTCCCTG
Colosseo_Als3  (1401)  CCTCATGAACATTCAGGAGTTGGCATTGATCCGTATTGAGAACCTCCCTG
Utopia_Als3    (1401)  CCTCATGAACATTCAGGAGTTGGCATTGATCCGTATTGAGAACCTCCCTG
Consensus      (1401)  CCTCATGAACATTCAGGAGTTGGCATTGATCCGTATTGAGAACCTCCCTG 1451                                                1500
Ciccio_Als3    (1451)  TGAAGGTGATGATATTGAACAACCAGCATCTGGGAATGGTGGTGCAATGG
Colosseo_Als3  (1451)  TGAAGGTGATGATATTGAACAACCAGCATCTGGGAATGGTGGTGCAATGG
Utopia_Als3    (1451)  TGAAGGTGATGATATTGAACAACCAGCATCTGGGAATGGTGGTGCAATGG
Consensus      (1451)  TGAAGGTGATGATATTGAACAACCAGCATCTGGGAATGGTGGTGCAATGG 1501                                                1550
Ciccio_Als3    (1501)  GAGGATAGGTTTTACAAGGCCAATCGGGCGCACACATACCTTGGCAACCC
Colosseo_Als3  (1501)  GAGGATAGGTTTTACAAGGCCAATCGGGCGCACACATACCTTGGCAACCC
Utopia_Als3    (1501)  GAGGATAGGTTTTACAAGGCCAATCGGGCGCACACATACCTTGGCAACCC
Consensus      (1501)  GAGGATAGGTTTTACAAGGCCAATCGGGCGCACACATACCTTGGCAACCC 1551                                                1600
Ciccio_Als3    (1551)  AGAAAATGAGAGTGAGATATATCCAGATTTTGTGACGATTGCTAAAGGAT
Colosseo_Als3  (1551)  AGAAAATGAGAGTGAGATATATCCAGATTTTGTGACGATTGCTAAAGGAT
Utopia_Als3    (1551)  AGAAAATGAGAGTGAGATATATCCAGATTTTGTGACGATTGCTAAAGGAT
Consensus      (1551)  AGAAAATGAGAGTGAGATATATCCAGATTTTGTGACGATTGCTAAAGGAT 1601                                                1650
Ciccio_Als3    (1601)  TCAACGTTCCGGCAGTTCGTGTGACGAAGAAGAGCGAAGTCACTGCAGCA
Colosseo_Als3  (1601)  TCAACGTTCCGGCAGTTCGTGTGACGAAGAAGAGCGAAGTCACTGCAGCA
Utopia_Als3    (1601)  TCAACGTTCCGGCAGTTCGTGTGACGAAGAAGAGCGAAGTCACTGCAGCA
Consensus      (1601)  TCAACGTTCCGGCAGTTCGTGTGACGAAGAAGAGCGAAGTCACTGCAGCA 1651                                                1700
Ciccio_Als3    (1651)  ATCAAGAAGATGCTTGAGACCCCAGGGCCATACTTGTTGGATATCATCGT
Colosseo_Als3  (1651)  ATCAAGAAGATGCTTGAGACCCCAGGGCCATACTTGTTGGATATCATCGT
Utopia_Als3    (1651)  ATCAAGAAGATGCTTGAGACCCCAGGGCCATACTTGTTGGATATCATCGT
Consensus      (1651)  ATCAAGAAGATGCTTGAGACCCCAGGGCCATACTTGTTGGATATCATCGT 1701                                                1750
Ciccio_Als3    (1701)  CCCGCATCAGGAGCACGTGCTGCCTATGATCCCAAGCGGTGGTGCTTTCA
Colosseo_Als3  (1701)  CCCGCATCAGGAGCACGTGCTGCCTATGATCCCAAGCGGTGGTGCTTTCA
Utopia_Als3    (1701)  CCCGCATCAGGAGCACGTGCTGCCTATGATCCCAAGCGGTGGTGCTTTCA
Consensus      (1701)  CCCGCATCAGGAGCACGTGCTGCCTATGATCCCAAGCGGTGGTGCTTTCA 1751                        1788
Ciccio_Als3    (1751)  AGGACATGATCATGGAGGGTGATGGCAGGACCTCGTAC
Colosseo_Als3  (1751)  AGGACATGATCATGGAGGGTGATGGCAGGACCTCGTAC
Utopia_Als3    (1751)  AGGACATGATCATGGAGGGTGATGGCAGGACCTCGTAC
Consensus      (1751)  AGGACATGATCATGGAGGGTGATGGCAGGACCTCGTAC
```

FIG.3A

```
                         1                                                  50
    CI19_Als2      (1)   TCCCCCGCCGCCACCTCCGCCGCGCCTCCCGCCACCGCGCTCCGGCCGTG
    Ciccio_Als2    (1)   TCCCCCGCCGCCACCTCCGCCGCGCCTCCCGCCACCGCGCTCCGGCCGTG
    UT15_Als2      (1)                   CGCGCCTCCCGCCACCGCGCTCCGGCCGTG
    UT19_Als2      (1)                             CACCGCGCTCCGGCCGTG
    Consensus      (1)   TCCCCCGCCGCCACCTCCGCCGCGCCTCCCGCCACCGCGCTCCGGCCGTG 51                                                100
    CI19_Als2     (51)   GGGCCCCTCCGAGCCCCGTAAGGGCGCCGACATCCTCGTCGAGGCGCTGG
    Ciccio_Als2   (51)   GGGCCCCTCCGAGCCCCGTAAGGGCGCCGACATCCTCGTCGAGGCGCTGG
    UT15_Als2     (31)   GGGCCCCTCCGAGCCCCGCAAGGGCGCCGACATCCTCGTCGAGGCGCTGG
    UT19_Als2     (19)   GGGCCCCTCCGAGCCCCGTAAGGGCGCCGACATCCTCGTCGAGGCGCTGG
    Consensus     (51)   GGGCCCCTCCGAGCCCCGYAAGGGCGCCGACATCCTCGTCGAGGCGCTGG 101                                               150
    CI19_Als2    (101)   AGCGCTGCGGCATCGTCGACGTCTTCGCCTACCCTGGCGGCGCGTCCATG
    Ciccio_Als2  (101)   AGCGCTGCGGCATCGTCGACGTCTTCGCCTACCCTGGCGGCGCGTCCATG
    UT15_Als2     (81)   AGCGCTGCGGCATCGTCGACGTCTTCGCCTACCCTGGCGGCGCGTCCATG
    UT19_Als2     (69)   AGCGCTGCGGCATCGTCGACGTCTTCGCCTACCCTGGCGGCGCGTCCATG
    Consensus    (101)   AGCGCTGCGGCATCGTCGACGTCTTCGCCTACCCTGGCGGCGCGTCCATG 151                                               200
    CI19_Als2    (151)   GAGATCCACCAGGCGCTGACGCGCTCGCCAGTCATCACCAACCACCTCTT
    Ciccio_Als2  (151)   GAGATCCACCAGGCGCTGACGCGCTCGCCAGTCATCACCAACCACCTCTT
    UT15_Als2    (131)   GAGATCCACCAGGCGCTGACGCGCTCGCCAGTCATCACCAACCACCTCTT
    UT19_Als2    (119)   GAGATCCACCAGGCGCTGACGCGCTCGCCAGTCATCACCAACCACCTCTT
    Consensus    (151)   GAGATCCACCAGGCGCTGACGCGCTCGCCAGTCATCACCAACCACCTCTT 201                                               250
    CI19_Als2    (201)   CCGCCACGAGCAGGGGGAGGCGTTCGCGGCGTCCGGGTACGCCCGCGCGT
    Ciccio_Als2  (201)   CCGCCACGAGCAGGGGGAGGCGTTCGCGGCGTCCGGGTACGCCCGCGCGT
    UT15_Als2    (181)   CCGCCACGAGCAGGGGGAGGCGTTCGCGGCGTCCGGGTACGCCCGCGCGT
    UT19_Als2    (169)   CCGCCACGAGCAGGGGGAGGCGTTCGCGGCGTCCGGGTACGCCCGCGCGT
    Consensus    (201)   CCGCCACGAGCAGGGGGAGGCGTTCGCGGCGTCCGGGTACGCCCGCGCGT 251                                               300
    CI19_Als2    (251)   CCGGCCGCGTCGGCGTCTGCGTCGCCACCTCCGGCCCGGGGGCCACCAAC
    Ciccio_Als2  (251)   CCGGCCGCGTCGGCGTCTGCGTCGCCACCTCCGGCCCGGGGGCCACCAAC
    UT15_Als2    (231)   CCGGCCGCGTCGGCGTCTGCGTCGCCACCTCCGGCCCGGGGGCCACCAAC
    UT19_Als2    (219)   CCGGCCGCGTCGGCGTCTGCGTCGCCACCTCCGGCCCGGGGGCCACCAAC
    Consensus    (251)   CCGGCCGCGTCGGCGTCTGCGTCGCCACCTCCGGCCCGGGGGCCACCAAC 301                                               350
    CI19_Als2    (301)   CTCGTCTCCGCGCTCGCCGACGCTCTCCTCGACTCCATCCCCATGGTCGC
    Ciccio_Als2  (301)   CTCGTCTCCGCGCTCGCCGACGCTCTCCTCGACTCCATCCCCATGGTCGC
    UT15_Als2    (281)   CTCGTCTCCGCGCTCGCCGACGCTCTCCTCGACTCCATCCCCATGGTCGC
    UT19_Als2    (269)   CTCGTCTCCGCGCTCGCCGACGCTCTCCTCGACTCCATCCCCATGGTCGC
    Consensus    (301)   CTCGTCTCCGCGCTCGCCGACGCTCTCCTCGACTCCATCCCCATGGTCGC
```

FIG.3B

```
              351                                                    400
CI19_Als2    (351) CATCACGGGCCAGGTCCCCCGCCGCATGATCGGCACGGATGCGTTCCAGG
Ciccio_Als2  (351) CATCACGGGCCAGGTCCCCCGCCGCATGATCGGCACGGATGCGTTCCAGG
UT15_Als2    (331) CATCACGGGCCAGGTCCCCCGCCGCATGATCGGCACGGATGCGTTCCAGG
UT19_Als2    (319) CATCACGGGCCAGGTCCCCCGCCGCATGATCGGCACGGATGCGTTCCAGG
Consensus    (351) CATCACGGGCCAGGTCCCCCGCCGCATGATCGGCACGGATGCGTTCCAGG 401                                                    450
CI19_Als2    (401) AGACGCCCATCGTGGAGGTCACGCGCTCCATCACCAAGCACAACTACCTG
Ciccio_Als2  (401) AGACGCCCATCGTGGAGGTCACGCGCTCCATCACCAAGCACAACTACCTG
UT15_Als2    (381) AGACGCCCATCGTGGAGGTCACGCGCTCCATCACCAAGCACAACTACCTG
UT19_Als2    (369) AGACGCCCATCGTGGAGGTCACGCGCTCCATCACCAAGCACAACTACCTG
Consensus    (401) AGACGCCCATCGTGGAGGTCACGCGCTCCATCACCAAGCACAACTACCTG 451                                                    500
CI19_Als2    (451) GTCCTTGACGTGGAGGATATCCCCCGCGTCATCCAGGAAGCCTTCTTCCT
Ciccio_Als2  (451) GTCCTTGACGTGGAGGATATCCCCCGCGTCATCCAGGAAGCCTTCTTCCT
UT15_Als2    (431) GTCCTTGACGTGGAGGATATCCCCCGCGTCATCCAGGAAGCCTTCTTCCT
UT19_Als2    (419) GTCCTTGACGTGGAGGATATCCCCCGCGTCATCCAGGAAGCCTTCTTCCT
Consensus    (451) GTCCTTGACGTGGAGGATATCCCCCGCGTCATCCAGGAAGCCTTCTTCCT 501                                                    550
CI19_Als2    (501) CGCATCCTCTGGCCGCCCGGGGCCGGTGCTGGTTGATATCCCCAAGGACA
Ciccio_Als2  (501) CGCATCCTCTGGCCGCCCGGGGCCGGTGCTGGTTGATATCCCCAAGGACA
UT15_Als2    (481) CGCATCCTCTGGCCGCCCGGGGCCGGTGCTGGTTGATATCCCCAAGGACA
UT19_Als2    (469) CGCATCCTCTGGCCGCCCGGGGCCGGTGCTGGTTGATATCCCCAAGGACA
Consensus    (501) CGCATCCTCTGGCCGCCCGGGGCCGGTGCTGGTTGATATCCCCAAGGACA 551                                                    600
CI19_Als2    (551) TCCAGCAGCAGATGGCTGTGCCTGTCTGGGACACGCCGATGAGTTTGCCA
Ciccio_Als2  (551) TCCAGCAGCAGATGGCTGTGCCTGTCTGGGACACGCCGATGAGTTTGCCA
UT15_Als2    (531) TCCAGCAGCAGATGGCTGTGCCTGTCTGGGACACGCCGATGAGTTTGCCA
UT19_Als2    (519) TCCAGCAGCAGATGGCTGTGCCTGTCTGGGACACGCCGATGAGTTTGCCA
Consensus    (551) TCCAGCAGCAGATGGCTGTGCCTGTCTGGGACACGCCGATGAGTTTGCCA 601                                                    650
CI19_Als2    (601) GGGTACATCGCCCGCCTGCCCAAGCCACCATCTACTGAATCGCTTGAGCA
Ciccio_Als2  (601) GGGTACATCGCCCGCCTGCCCAAGCCACCATCTACTGAATCGCTTGAGCA
UT15_Als2    (581) GGGTACATCGCCCGCCTGCCCAAGCCACCATCTACTGAATCGCTTGAGCA
UT19_Als2    (569) GGGTACATCGCCCGCCTGCCCAAGCCACCATCTACTGAATCGCTTGAGCA
Consensus    (601) GGGTACATCGCCCGCCTGCCCAAGCCACCATCTACTGAATCGCTTGAGCA 651                                                    700
CI19_Als2    (651) GGTCCTGCGTCTGGTTGGCGAGTCACGGCGCCCAATTCTGTATGTTGGTG
Ciccio_Als2  (651) GGTCCTGCGTCTGGTTGGCGAGTCACGGCGCCCAATTCTGTATGTTGGTG
UT15_Als2    (631) GGTCCTGCGTCTGGTTGGCGAGTCACGGCGCCCAATTCTGTATGTTGGTG
UT19_Als2    (619) GGTCCTGCGTCTGGTTGGCGAGTCACGGCGCCCAATTCTGTATGTTGGTG
Consensus    (651) GGTCCTGCGTCTGGTTGGCGAGTCACGGCGCCCAATTCTGTATGTTGGTG 701                                                    750
CI19_Als2    (701) GTGGCTGCGCTGCATCTGGTGAGGAGTTGCGCCGCTTTGTTGAGCTCACT
Ciccio_Als2  (701) GTGGCTGCGCTGCATCTGGTGAGGAGTTGCGCCGCTTTGTTGAGCTCACT
UT15_Als2    (681) GTGGCTGCGCTGCATCTGGTGAGGAGTTGCGCCGCTTTGTTGAGCTCACT
UT19_Als2    (669) GTGGCTGCGCTGCATCTGGTGAGGAGTTGCGCCGCTTTGTTGAGCTCACT
Consensus    (701) GTGGCTGCGCTGCATCTGGTGAGGAGTTGCGCCGCTTTGTTGAGCTCACT
```

FIG.3C

```
                        751                                                 800
   CI19_Als2    ( 751)  GGGATTCCAGTTACAACTACTCTTATGGGCCTTGGCAACTTCCCCAGTGA
 Ciccio_Als2    ( 751)  GGGATTCCAGTTACAACTACTCTTATGGGCCTTGGCAACTTCCCCAGTGA
   UT15_Als2    ( 731)  GGGATTCCAGTTACAACTACTCTTATGGGCCTTGGCAACTTCCCCAGTGA
   UT19_Als2    ( 719)  GGGATTCCAGTTACAACTACTCTTATGGGCCTTGGCAACTTCCCCAGTGA
    Consensus   ( 751)  GGGATTCCAGTTACAACTACTCTTATGGGCCTTGGCAACTTCCCCAGTGA 801                                                 850
   CI19_Als2    ( 801)  CGACCCACTGTCTCTGCGCATGCTGGCGATGCATGGCACTGTGTATGCAA
 Ciccio_Als2    ( 801)  CGACCCACTGTCTCTGCGCATGCTGGGGATGCATGGCACTGTGTATGCAA
   UT15_Als2    ( 781)  CGACCCACTGTCTCTGCGCATGCTGGGGATGCATGGCACTGTGTATGCAA
   UT19_Als2    ( 769)  CGACCCACTGTCTCTGCGCATGCTGGGGATGCATGGCACTGTGTATGCAA
    Consensus   ( 801)  CGACCCACTGTCTCTGCGCATGCTGGGGATGCATGGCACTGTGTATGCAA 851                                                 900
   CI19_Als2    ( 851)  ATTATGCAGTAGATAAGGCTGACCTGTTGCTTGCATTTGGTGTGCGGTTT
 Ciccio_Als2    ( 851)  ATTATGCAGTAGATAAGGCTGACCTGTTGCTTGCATTTGGTGTGCGGTTT
   UT15_Als2    ( 831)  ATTATGCAGTAGATAAGGCTGACCTGTTGCTTGCATTTGGTGTGCGGTTT
   UT19_Als2    ( 819)  ATTATGCAGTAGATAAGGCTGACCTGTTGCTTGCATTTGGTGTGCGGTTT
    Consensus   ( 851)  ATTATGCAGTAGATAAGGCTGACCTGTTGCTTGCATTTGGTGTGCGGTTT 901                                                 950
   CI19_Als2    ( 901)  GATGATCGTGTGACCGGGAAAATCGAGGCTTTTGCAAGCAGGTCCAAGAT
 Ciccio_Als2    ( 901)  GATGATCGTGTGACCGGGAAAATCGAGGCTTTTGCAAGCAGGTCCAAGAT
   UT15_Als2    ( 881)  GATGATCGTGTGACCGGGAAAATCGAGGCTTTTGCAAGCAGGTCCAAGAT
   UT19_Als2    ( 869)  GATGATCGTGTGACCGGGAAAATCGAGGCTTTTGCAAGCAGGTCCAAGAT
    Consensus   ( 901)  GATGATCGTGTGACCGGGAAAATCGAGGCTTTTGCAAGCAGGTCCAAGAT 951                                                1000
   CI19_Als2    ( 951)  TGTGCACATTGACATTGACCCAGCTGAGATTGGCAAGAACAAGCAGCCAC
 Ciccio_Als2    ( 951)  TGTGCACATTGACATTGACCCAGCTGAGATTGGCAAGAACAAGCAGCCAC
   UT15_Als2    ( 931)  TGTGCACATTGACATTGACCCAGCTGAGATTGGCAAGAACAAGCAGCCAC
   UT19_Als2    ( 919)  TGTGCACATTGACATTGACCCAGCTGAGATTGGCAAGAACAAGCAGCCAC
    Consensus   ( 951)  TGTGCACATTGACATTGACCCAGCTGAGATTGGCAAGAACAAGCAGCCAC 1001                                                1050
   CI19_Als2    (1001)  ATGTCTCCATTTGTGCAGATGTTAAGCTTGCTTTACAGGGGTTGAATGCT
 Ciccio_Als2    (1001)  ATGTCTCCATTTGTGCAGATGTTAAGCTTGCTTTACAGGGGTTGAATGCT
   UT15_Als2    ( 981)  ATGTCTCCATTTGTGCAGATGTTAAGCTTGCTTTACAGGGGTTGAATGCT
   UT19_Als2    ( 969)  ATGTCTCCATTTGTGCAGATGTTAAGCTTGCTTTACAGGGGTTGAATGCT
    Consensus   (1001)  ATGTCTCCATTTGTGCAGATGTTAAGCTTGCTTTACAGGGGTTGAATGCT 1051                                                1100
   CI19_Als2    (1051)  CTATTAAATGGGAGCAAAGCACAACAGGGTCTGGATTTTGGTCCATGGCA
 Ciccio_Als2    (1051)  CTATTAAATGGGAGCAAAGCACAACAGGGTCTGGATTTTGGTCCATGGCA
   UT15_Als2    (1031)  CTATTAAATGGGAGCAAAGCACAACAGGGTCTGGATTTTGGTCCATGGCA
   UT19_Als2    (1019)  CTATTAAATGGGAGCAAAGCACAACAGGGTCTGGATTTTGGTCCATGGCA
    Consensus   (1051)  CTATTAAATGGGAGCAAAGCACAACAGGGTCTGGATTTTGGTCCATGGCA 1101                                                1150
   CI19_Als2    (1101)  CAAGGAGTTGGATCAGCAGAAGAGGGAGTTTCCTCTAGGATTCAAGACTT
 Ciccio_Als2    (1101)  CAAGGAGTTGGATCAGCAGAAGAGGGAGTTTCCTCTAGGATTCAAGACTT
   UT15_Als2    (1081)  CAAGGAGTTGGATCAGCAGAAGAGGGAGTTTCCTCTAGGATTCAAGACTT
   UT19_Als2    (1069)  CAAGGAGTTGGATCAGCAGAAGAGGGAGTTTCCTCTAGGATTCAAGACTT
    Consensus   (1101)  CAAGGAGTTGGATCAGCAGAAGAGGGAGTTTCCTCTAGGATTCAAGACTT
```

FIG.3D

```
                    1151                                                    1200
    CI19_Als2  (1151) TTGGTGAGGCCATCCCGCCGCAATATGCTATCCAGGTACTGGATGAGCTG
  Ciccio_Als2  (1151) TTGGTGAGGCCATCCCGCCGCAATATGCTATCCAGGTACTGGATGAGCTG
    UT15_Als2  (1131) TTGGTGAGGCCATCCCGCCGCAATATGCTATCCAGGTACTGGATGAGCTG
    UT19_Als2  (1119) TTGGTGAGGCCATCCCGCCGCAATATGCTATCCAGGTACTGGATGAGCTG
    Consensus  (1151) TTGGTGAGGCCATCCCGCCGCAATATGCTATCCAGGTACTGGATGAGCTG 1201                                                    1250
    CI19_Als2  (1201) ACAAAAGGGGAGGCGATCATTGCCACCGGTGTTGGGCAGCATCAGATGTG
  Ciccio_Als2  (1201) ACAAAAGGGGAGGCGATCATTGCCACCGGTGTTGGGCAGCATCAGATGTG
    UT15_Als2  (1181) ACAAAAGGGGAGGCGATCATTGCCACCGGTGTTGGGCAGCATCAGATGTG
    UT19_Als2  (1169) ACAAAAGGGGAGGCGATCATTGCCACCGGTGTTGGGCAGCATCAGATGTG
    Consensus  (1201) ACAAAAGGGGAGGCGATCATTGCCACCGGTGTTGGGCAGCATCAGATGTG 1251                                                    1300
    CI19_Als2  (1251) GGCGGCTCAGTATTACACTTACAAGCGGCCACGGCAGTGGCTGTCTTCGT
  Ciccio_Als2  (1251) GGCGGCTCAGTATTACACTTACAAGCGGCCACGGCAGTGGCTGTCTTCGT
    UT15_Als2  (1231) GGCGGCTCAGTATTACACTTACAAGCGGCCACGGCAGTGGCTGTCTTCGT
    UT19_Als2  (1219) GGCGGCTCAGTATTACACTTACAAGCGGCCACGGCAGTGGCTGTCTTCGT
    Consensus  (1251) GGCGGCTCAGTATTACACTTACAAGCGGCCACGGCAGTGGCTGTCTTCGT 1301                                                    1350
    CI19_Als2  (1301) CCGGTTTGGGTGCAATGGGATTTGGGTTGCCAGCTGCAGCTGGCGCTGCT
  Ciccio_Als2  (1301) CCGGTTTGGGTGCAATGGGATTTGGGTTGCCAGCTGCAGCTGGCGCTGCT
    UT15_Als2  (1281) CCGGTTTGGGTGCAATGGGATTTGGGTTGCCAGCTGCAGCTGGCGCTGCT
    UT19_Als2  (1269) CCGGTTTGGGTGCAATGGGATTTGGGTTGCCAGCTGCAGCTGGCGCTGCT
    Consensus  (1301) CCGGTTTGGGTGCAATGGGATTTGGGTTGCCAGCTGCAGCTGGCGCTGCT 1351                                                    1400
    CI19_Als2  (1351) GTGGCCAACCCAGGTGTTACAGTTGTTGACATTGATGGGGATGGTAGTTT
  Ciccio_Als2  (1351) GTGGCCAACCCAGGTGTTACAGTTGTTGACATTGATGGGGATGGTAGTTT
    UT15_Als2  (1331) GTGGCCAACCCAGGTGTTACAGTTGTTGACATTGATGGGGATGGTAGTTT
    UT19_Als2  (1319) GTGGCCAACCCAGGTGTTACAGTTGTTGACATTGATGGGGATGGTAGTTT
    Consensus  (1351) GTGGCCAACCCAGGTGTTACAGTTGTTGACATTGATGGGGATGGTAGTTT 1401                                                    1450
    CI19_Als2  (1401) CCTCATGAACATTCAGGAGTTGGCGTTGATCCGTATTGAGAACCTCCCAG
  Ciccio_Als2  (1401) CCTCATGAACATTCAGGAGTTGGCGTTGATCCGTATTGAGAACCTCCCAG
    UT15_Als2  (1381) CCTCATGAACATTCAGGAGTTGGCGTTGATCCGTATTGAGAACCTCCCAG
    UT19_Als2  (1369) CCTCATGAACATTCAGGAGTTGGCGTTGATCCGTATTGAGAACCTCCCAG
    Consensus  (1401) CCTCATGAACATTCAGGAGTTGGCGTTGATCCGTATTGAGAACCTCCCAG 1451                                                    1500
    CI19_Als2  (1451) TGAAGGTGATGATATTGAACAACCAGCATCTGGGAATGGTGGTGCAGTGG
  Ciccio_Als2  (1451) TGAAGGTGATGATATTGAACAACCAGCATCTGGGAATGGTGGTGCAGTGG
    UT15_Als2  (1431) TGAAGGTGATGATATTGAACAACCAGCATCTGGGAATGGTGGTGCAGTGG
    UT19_Als2  (1419) TGAAGGTGATGATATTGAACAACCAGCATCTGGGAATGGTGGTGCAGTGG
    Consensus  (1451) TGAAGGTGATGATATTGAACAACCAGCATCTGGGAATGGTGGTGCAGTGG 1501                                                    1550
    CI19_Als2  (1501) GAGGATAGGTTTTACAAGGCCAACCGGGCGCACACATACCTTGGCAACCC
  Ciccio_Als2  (1501) GAGGATAGGTTTTACAAGGCCAACCGGGCGCACACATACCTTGGCAACCC
    UT15_Als2  (1481) GAGGATAGGTTTTACAAGGCCAACCGGGCGCACACATACCTTGGCAACCC
    UT19_Als2  (1469) GAGGATAGGTTTTACAAGGCCAACCGGGCGCACACATACCTTGGCAACCC
    Consensus  (1501) GAGGATAGGTTTTACAAGGCCAACCGGGCGCACACATACCTTGGCAACCC
```

FIG.3E

```
                    1551                                            1600
CI19_Als2    (1551) AGAAAATGAGGGTGAGATATATCCAGATTTTGTGACGATTGCTAAAGGAT
Ciccio_Als2  (1551) AGAAAATGAGGGTGAGATATATCCAGATTTTGTGACGATTGCTAAAGGAT
UT15_Als2    (1531) AGAAAATGAGGGTGAGATATATCCAGATTTTGTGACGATTGCTAAAGGAT
UT19_Als2    (1519) AGAAAATGAGGGTGAGATATATCCAGATTTTGTGACGATTGCTAAAGGAT
Consensus    (1551) AGAAAATGAGGGTGAGATATATCCAGATTTTGTGACGATTGCTAAAGGAT 1601                                            1650
CI19_Als2    (1601) TCAACGTTCCGGCAGTTCGTGTGACGAAGAAGAGCGAAGTCACTGCAGCA
Ciccio_Als2  (1601) TCAACGTTCCGGCAGTTCGTGTGACGAAGAAGAGCGAAGTCACTGCAGCA
UT15_Als2    (1581) TCAACGTTCCGGCAGTTCGTGTGACGAAGAAGAGCGAAGTCACTGCAGCA
UT19_Als2    (1569) TCAACGTTCCGGCAGTTCGTGTGACGAAGAAGAGCGAAGTCACTGCAGCA
Consensus    (1601) TCAACGTTCCGGCAGTTCGTGTGACGAAGAAGAGCGAAGTCACTGCAGCA 1651                                            1700
CI19_Als2    (1651) ATCAAGAAGATGCTTGAGACCCCAGGGCCATACTTGTTGGATATCATTGT
Ciccio_Als2  (1651) ATCAAGAAGATGCTTGAGACCCCAGGGCCATACTTGTTGGATATCATTGT
UT15_Als2    (1631) ATCAAGAAGATGCTTGAGACCCCAGGGCCATACTTGTTGGATATCATTGT
UT19_Als2    (1619) ATCAAGAAGATGCTTGAGACCCCAGGGCCATACTTGTTGGATATCATTGT
Consensus    (1651) ATCAAGAAGATGCTTGAGACCCCAGGGCCATACTTGTTGGATATCATTGT 1701                                            1750
CI19_Als2    (1701) CCCGCATCAGGAGCACGTGCTGCCTATGATCCCAAACGGTGGTGCTTTTA
Ciccio_Als2  (1701) CCCGCATCAGGAGCACGTGCTGCCTATGATCCCAAGCGGTGGTGCTTTTA
UT15_Als2    (1681) CCCGCATCAGGAGCACGTGCTGCCTATGATCCCAAGCGGTGGTGCTTTTA
UT19_Als2    (1669) CCCGCATCAGGAGCACGTGCTGCCTATGATCCCAAGCGGTGGTGCTTTTA
Consensus    (1701) CCCGCATCAGGAGCACGTGCTGCCTATGATCCCAARCGGTGGTGCTTTTA 1751                       1788
CI19_Als2    (1751) AGGACATGATCATGGAGGGTGATGGCAGGACCTCGTAC
Ciccio_Als2  (1751) AGGACATGATCATGGAGGGTGATGGCAGGACCTCGTAC
UT15_Als2    (1731) AGGACATGATCATGGAGGGTGATGGCAGGACCTCGTAC
UT19_Als2    (1719) AGGACATGATCATGGAGGGTGATGGCAGGACCTCGTAC
Consensus    (1751) AGGACATGATCATGGAGGGTGATGGCAGGACCTCGTAC
```

FIG.4A

```
                  1                                                  50
CI19_Als2    (1)  SPAATSAAPPATALRPWGPSEPRKGADILVEALERCGIVDVFAYPGGASM
Ciccio_Als2  (1)  SPAATSAAPPATALRPWGPSEPRKGADILVEALERCGIVDVFAYPGGASM
UT15_Als2    (1)         APPATALRPWGPSEPRKGADILVEALERCGIVDVFAYPGGASM
UT19_Als2    (1)             TALRPWGPSEPRKGADILVEALERCGIVDVFAYPGGASM
Consensus    (1)  SPAATSAAPPATALRPWGPSEPRKGADILVEALERCGIVDVFAYPGGASM 51                                                 100
CI19_Als2    (51) EIHQALTRSPVITNHLFRHEQGEAFAASGYARASGRVGVCVATSGPGATN
Ciccio_Als2  (51) EIHQALTRSPVITNHLFRHEQGEAFAASGYARASGRVGVCVATSGPGATN
UT15_Als2    (44) EIHQALTRSPVITNHLFRHEQGEAFAASGYARASGRVGVCVATSGPGATN
UT19_Als2    (40) EIHQALTRSPVITNHLFRHEQGEAFAASGYARASGRVGVCVATSGPGATN
Consensus    (51) EIHQALTRSPVITNHLFRHEQGEAFAASGYARASGRVGVCVATSGPGATN 101                                                150
CI19_Als2   (101) LVSALADALLDSIPMVAITGQVPRRMIGTDAFQETPIVEVTRSITKHNYL
Ciccio_Als2 (101) LVSALADALLDSIPMVAITGQVPRRMIGTDAFQETPIVEVTRSITKHNYL
UT15_Als2    (94) LVSALADALLDSIPMVAITGQVPRRMIGTDAFQETPIVEVTRSITKHNYL
UT19_Als2    (90) LVSALADALLDSIPMVAITGQVPRRMIGTDAFQETPIVEVTRSITKHNYL
Consensus   (101) LVSALADALLDSIPMVAITGQVPRRMIGTDAFQETPIVEVTRSITKHNYL 151                                                200
CI19_Als2   (151) VLDVEDIPRVIQEAFFLASSGRPGPVLVDIPKDIQQQMAVPVWDTPMSLP
Ciccio_Als2 (151) VLDVEDIPRVIQEAFFLASSGRPGPVLVDIPKDIQQQMAVPVWDTPMSLP
UT15_Als2   (144) VLDVEDIPRVIQEAFFLASSGRPGPVLVDIPKDIQQQMAVPVWDTPMSLP
UT19_Als2   (140) VLDVEDIPRVIQEAFFLASSGRPGPVLVDIPKDIQQQMAVPVWDTPMSLP
Consensus   (151) VLDVEDIPRVIQEAFFLASSGRPGPVLVDIPKDIQQQMAVPVWDTPMSLP 201                                                250
CI19_Als2   (201) GYIARLPKPPSTESLEQVLRLVGESRRPILYVGGGCAASGEELRRFVELT
Ciccio_Als2 (201) GYIARLPKPPSTESLEQVLRLVGESRRPILYVGGGCAASGEELRRFVELT
UT15_Als2   (194) GYIARLPKPPSTESLEQVLRLVGESRRPILYVGGGCAASGEELRRFVELT
UT19_Als2   (190) GYIARLPKPPSTESLEQVLRLVGESRRPILYVGGGCAASGEELRRFVELT
Consensus   (201) GYIARLPKPPSTESLEQVLRLVGESRRPILYVGGGCAASGEELRRFVELT 251                                                300
CI19_Als2   (251) GIPVTTTLMGLGNFPSDDPLSLRMLGMHGTVYANYAVDKADLLLAFGVRF
Ciccio_Als2 (251) GIPVTTTLMGLGNFPSDDPLSLRMLGMHGTVYANYAVDKADLLLAFGVRF
UT15_Als2   (244) GIPVTTTLMGLGNFPSDDPLSLRMLGMHGTVYANYAVDKADLLLAFGVRF
UT19_Als2   (240) GIPVTTTLMGLGNFPSDDPLSLRMLGMHGTVYANYAVDKADLLLAFGVRF
Consensus   (251) GIPVTTTLMGLGNFPSDDPLSLRMLGMHGTVYANYAVDKADLLLAFGVRF 301                                                350
CI19_Als2   (301) DDRVTGKIEAFASRSKIVHIDIDPAEIGKNKQPHVSICADVKLALQGLNA
Ciccio_Als2 (301) DDRVTGKIEAFASRSKIVHIDIDPAEIGKNKQPHVSICADVKLALQGLNA
UT15_Als2   (294) DDRVTGKIEAFASRSKIVHIDIDPAEIGKNKQPHVSICADVKLALQGLNA
UT19_Als2   (290) DDRVTGKIEAFASRSKIVHIDIDPAEIGKNKQPHVSICADVKLALQGLNA
Consensus   (301) DDRVTGKIEAFASRSKIVHIDIDPAEIGKNKQPHVSICADVKLALQGLNA
```

FIG.4B

```
                    351                                                  400
CI19_Als2    (351)  LLNGSKAQQGLDFGPWHKELDQQKREFPLGFKTFGEAIPPQYAIQVLDEL
Ciccio_Als2  (351)  LLNGSKAQQGLDFGPWHKELDQQKREFPLGFKTFGEAIPPQYAIQVLDEL
UT15_Als2    (344)  LLNGSKAQQGLDFGPWHKELDQQKREFPLGFKTFGEAIPPQYAIQVLDEL
UT19_Als2    (340)  LLNGSKAQQGLDFGPWHKELDQQKREFPLGFKTFGEAIPPQYAIQVLDEL
Consensus    (351)  LLNGSKAQQGLDFGPWHKELDQQKREFPLGFKTFGEAIPPQYAIQVLDEL 401                                                  450
CI19_Als2    (401)  TKGEAIIATGVGQHQMWAAQYYTYKRPRQWLSSSGLGAMGFGLPAAAGAA
Ciccio_Als2  (401)  TKGEAIIATGVGQHQMWAAQYYTYKRPRQWLSSSGLGAMGFGLPAAAGAA
UT15_Als2    (394)  TKGEAIIATGVGQHQMWAAQYYTYKRPRQWLSSSGLGAMGFGLPAAAGAA
UT19_Als2    (390)  TKGEAIIATGVGQHQMWAAQYYTYKRPRQWLSSSGLGAMGFGLPAAAGAA
Consensus    (401)  TKGEAIIATGVGQHQMWAAQYYTYKRPRQWLSSSGLGAMGFGLPAAAGAA 451                                                  500
CI19_Als2    (451)  VANPGVTVVDIDGDGSFLMNIQELALIRIENLPVKVMILNNQHLGMVVQW
Ciccio_Als2  (451)  VANPGVTVVDIDGDGSFLMNIQELALIRIENLPVKVMILNNQHLGMVVQW
UT15_Als2    (444)  VANPGVTVVDIDGDGSFLMNIQELALIRIENLPVKVMILNNQHLGMVVQW
UT19_Als2    (440)  VANPGVTVVDIDGDGSFLMNIQELALIRIENLPVKVMILNNQHLGMVVQW
Consensus    (451)  VANPGVTVVDIDGDGSFLMNIQELALIRIENLPVKVMILNNQHLGMVVQW 501                                                  550
CI19_Als2    (501)  EDRFYKANRAHTYLGNPENEGEIYPDFVTIAKGFNVPAVRVTKKSEVTAA
Ciccio_Als2  (501)  EDRFYKANRAHTYLGNPENEGEIYPDFVTIAKGFNVPAVRVTKKSEVTAA
UT15_Als2    (494)  EDRFYKANRAHTYLGNPENEGEIYPDFVTIAKGFNVPAVRVTKKSEVTAA
UT19_Als2    (490)  EDRFYKANRAHTYLGNPENEGEIYPDFVTIAKGFNVPAVRVTKKSEVTAA
Consensus    (501)  EDRFYKANRAHTYLGNPENEGEIYPDFVTIAKGFNVPAVRVTKKSEVTAA 551                                                  600
CI19_Als2    (551)  IKKMLETPGPYLLDIIVPHQEHVLPMIPNGGAFKDMIMEGDGRTSY
Ciccio_Als2  (551)  IKKMLETPGPYLLDIIVPHQEHVLPMIPSGGAFKDMIMEGDGRTSY
UT15_Als2    (544)  IKKMLETPGPYLLDIIVPHQEHVLPMIPSGGAFKDMIMEGDGRTSY
UT19_Als2    (540)  IKKMLETPGPYLLDIIVPHQEHVLPMIPSGGAFKDMIMEGDGRTSY
Consensus    (551)  IKKMLETPGPYLLDIIVPHQEHVLPMIPXGGAFKDMIMEGDGRTSY
```

FIG.5A

```
                          1                                                50
     UT15_Als3     (1)    --------------------------------------------------
     UT19_Als3     (1)    --------------------------------------------------
 Utopia_Als3_ORF   (1)    TCCCCCGCCGCCACCTCCGCCGCGCCCCCCGCCACCGCGCTCCGGCCCTG
     Consensus     (1)

51                                               100
     UT15_Als3     (1)    ------------------CCGCAAGGGCGCCGACATCCTCGTCGAGGCGCTCG
     UT19_Als3     (1)    ------------------------------GACATCCTCGTCGAGGCGCTCG
 Utopia_Als3_ORF   (51)   GGGCCCGTCCGAGCCCCGCAAGGGCGCCGACATCCTCGTCGAGGCGCTCG
     Consensus     (51)                     CCGCAAGGGCGCCGACATCCTCGTCGAGGCGCTCG 101                                              150
     UT15_Als3     (36)   AGCGCTGCGGCATCGTCGACGTATTCGCCTACCCCGGCGGC CGTCCATG
     UT19_Als3     (23)   AGCGCTGCGGCATCGTCGACGTATTCGCCTACCCCGGCGGC CGTCCATG
 Utopia_Als3_ORF  (101)   AGCGCTGCGGCATCGTCGACGTATTCGCCTACCCCGGCGGCGCGTCCATG
     Consensus    (101)   AGCGCTGCGGCATCGTCGACGTATTCGCCTACCCCGGCGGCRCGTCCATG 151                                              200
     UT15_Als3     (86)   GAGATCCACCAGGCGCTGACGCGCTCGCCCGTCATCACCAACCACCTCTT
     UT19_Als3     (73)   GAGATCCACCAGGCGCTGACGCGCTCGCCCGTCATCACCAACCACCTCTT
 Utopia_Als3_ORF  (151)   GAGATCCACCAGGCGCTGACGCGCTCGCCCGTCATCACCAACCACCTCTT
     Consensus    (151)   GAGATCCACCAGGCGCTGACGCGCTCGCCCGTCATCACCAACCACCTCTT 201                                              250
     UT15_Als3    (136)   CCGCCACGAGCAGGGGGAGGCGTTCGCGGCGTCCGGCTACGCCCGCGCGT
     UT19_Als3    (123)   CCGCCACGAGCAGGGGGAGGCGTTCGCGGCGTCCGGCTACGCCCGCGCGT
 Utopia_Als3_ORF  (201)   CCGCCACGAGCAGGGGGAGGCGTTCGCGGCGTCCGGCTACGCCCGCGCGT
     Consensus    (201)   CCGCCACGAGCAGGGGGAGGCGTTCGCGGCGTCCGGCTACGCCCGCGCGT 251                                              300
     UT15_Als3    (186)   CCGGCCGCGTCGGCGTCTGCGTCGCCACCTCCGGCCCGGGGGCCACCAAC
     UT19_Als3    (173)   CCGGCCGCGTCGGCGTCTGCGTCGCCACCTCCGGCCCGGGGGCCACCAAC
 Utopia_Als3_ORF  (251)   CCGGCCGCGTCGGCGTCTGCGTCGCCACCTCCGGCCCGGGGGCCACCAAC
     Consensus    (251)   CCGGCCGCGTCGGCGTCTGCGTCGCCACCTCCGGCCCGGGGGCCACCAAC 301                                              350
     UT15_Als3    (236)   CTCGTCTCCGCGCTCGCTGACGCCCTCCTCGACTCCATCCCCATGGTCGC
     UT19_Als3    (223)   CTCGTCTCCGCGCTCGCTGACGCCCTCCTCGACTCCATCCCCATGGTCGC
 Utopia_Als3_ORF  (301)   CTCGTCTCCGCGCTCGCTGACGCCCTCCTCGACTCCATCCCCATGGTCGC
     Consensus    (301)   CTCGTCTCCGCGCTCGCTGACGCCCTCCTCGACTCCATCCCCATGGTCGC 351                                              400
     UT15_Als3    (286)   CATCACGGGCCAGGTCCCCCGCCGCATGATCGGCACGGACGCGTTCCAGG
     UT19_Als3    (273)   CATCACGGGCCAGGTCCCCCGCCGCATGATCGGCACGGACGCGTTCCAGG
 Utopia_Als3_ORF  (351)   CATCACGGGCCAGGTCCCCCGCCGCATGATCGGCACGGACGCGTTCCAGG
     Consensus    (351)   CATCACGGGCCAGGTCCCCCGCCGCATGATCGGCACGGACGCGTTCCAGG 401                                              450
     UT15_Als3    (336)   AGACGCCCATAGTGGAGGTCACGCGCTCCATCACCAAGCACAACTACCTG
     UT19_Als3    (323)   AGACGCCCATAGTGGAGGTCACGCGCTCCATCACCAAGCACAACTACCTG
 Utopia_Als3_ORF  (401)   AGACGCCCATAGTGGAGGTCACGCGCTCCATCACCAAGCACAACTACCTG
     Consensus    (401)   AGACGCCCATAGTGGAGGTCACGCGCTCCATCACCAAGCACAACTACCTG
```

FIG.5B

```
                         451                                                500
     UT15_Als3    (386)  GTCCTTGACGTGGAGGATATCCCCCGCGTCATCCAGGAAGCCTTCTTCCT
     UT19_Als3    (373)  GTCCTTGACGTGGAGGATATCCCCCGCGTCATCCAGGAAGCCTTCTTCCT
Utopia_Als3_ORF   (451)  GTCCTTGACGTGGAGGATATCCCCCGCGTCATCCAGGAAGCCTTCTTCCT
     Consensus    (451)  GTCCTTGACGTGGAGGATATCCCCCGCGTCATCCAGGAAGCCTTCTTCCT 501                                                550
     UT15_Als3    (436)  CGCGTCCTCTGGCCGCCCGGGGCCGGTGCTGGTTGATATCCCCAAGGATA
     UT19_Als3    (423)  CGCGTCCTCTGGCCGCCCGGGGCCGGTGCTGGTTGATATCCCCAAGGATA
Utopia_Als3_ORF   (501)  CGCGTCCTCTGGCCGCCCGGGGCCGGTGCTGGTTGATATCCCCAAGGATA
     Consensus    (501)  CGCGTCCTCTGGCCGCCCGGGGCCGGTGCTGGTTGATATCCCCAAGGATA 551                                                600
     UT15_Als3    (486)  TCCAGCAGCAGATGGCCGTGCCTATCTGGGACACGCCGATGAGTTTGCCA
     UT19_Als3    (473)  TCCAGCAGCAGATGGCCGTGCCTATCTGGGACACGCCGATGAGTTTGCCA
Utopia_Als3_ORF   (551)  TCCAGCAGCAGATGGCCGTGCCTATCTGGGACACGCCGATGAGTTTGCCA
     Consensus    (551)  TCCAGCAGCAGATGGCCGTGCCTATCTGGGACACGCCGATGAGTTTGCCA 601                                                650
     UT15_Als3    (536)  GGGTACATCGCCCGCCTGCCCAAGCCACCATCTACTGAATCGCTTGAGCA
     UT19_Als3    (523)  GGGTACATCGCCCGCCTGCCCAAGCCACCATCTACTGAATCGCTTGAGCA
Utopia_Als3_ORF   (601)  GGGTACATCGCCCGCCTGCCCAAGCCACCATCTACTGAATCGCTTGAGCA
     Consensus    (601)  GGGTACATCGCCCGCCTGCCCAAGCCACCATCTACTGAATCGCTTGAGCA 651                                                700
     UT15_Als3    (586)  GGTCCTGCGTCTGGTTGGCGAGTCACGGCGCCCAATTCTGTATGTTGGTG
     UT19_Als3    (573)  GGTCCTGCGTCTGGTTGGCGAGTCACGGCGCCCAATTCTGTATGTTGGTG
Utopia_Als3_ORF   (651)  GGTCCTGCGTCTGGTTGGCGAGTCACGGCGCCCAATTCTGTATGTTGGTG
     Consensus    (651)  GGTCCTGCGTCTGGTTGGCGAGTCACGGCGCCCAATTCTGTATGTTGGTG 701                                                750
     UT15_Als3    (636)  GTGGCTGCGCTGCATCCGGCGAGGAGTTGCGCCGCTTTGTTGAGCTCACT
     UT19_Als3    (623)  GTGGCTGCGCTGCATCCGGCGAGGAGTTGCGCCGCTTTGTTGAGCTCACT
Utopia_Als3_ORF   (701)  GTGGCTGCGCTGCATCCGGCGAGGAGTTGCGCCGCTTTGTTGAGCTCACT
     Consensus    (701)  GTGGCTGCGCTGCATCCGGCGAGGAGTTGCGCCGCTTTGTTGAGCTCACT 751                                                800
     UT15_Als3    (686)  GGGATTCCGGTTACAACTACTCTGATGGGCCTTGGCAACTTCCCCAGCGA
     UT19_Als3    (673)  GGGATTCCGGTTACAACTACTCTGATGGGCCTTGGCAACTTCCCCAGCGA
Utopia_Als3_ORF   (751)  GGGATTCCGGTTACAACTACTCTGATGGGCCTTGGCAACTTCCCCAGCGA
     Consensus    (751)  GGGATTCCGGTTACAACTACTCTGATGGGCCTTGGCAACTTCCCCAGCGA 801                                                850
     UT15_Als3    (736)  CGACCCACTGTCTCTGCGCATGCTTGGGATGCATGGCACTGTGTATGCAA
     UT19_Als3    (723)  CGACCCACTGTCTCTGCGCATGCTTGGGATGCATGGCACTGTGTATGCAA
Utopia_Als3_ORF   (801)  CGACCCACTGTCTCTGCGCATGCTTGGGATGCATGGCACTGTGTATGCAA
     Consensus    (801)  CGACCCACTGTCTCTGCGCATGCTTGGGATGCATGGCACTGTGTATGCAA 851                                                900
     UT15_Als3    (786)  ATTATGCAGTCGATAAGGCTGACCTGTTGCTTGCATTTGGTGTGCGGTTT
     UT19_Als3    (773)  ATTATGCAGTCGATAAGGCTGACCTGTTGCTTGCATTTGGTGTGCGGTTT
Utopia_Als3_ORF   (851)  ATTATGCAGTCGATAAGGCTGACCTGTTGCTTGCATTTGGTGTGCGGTTT
     Consensus    (851)  ATTATGCAGTCGATAAGGCTGACCTGTTGCTTGCATTTGGTGTGCGGTTT
```

FIG.5C

```
                      901                                                  950
UT15_Als3     (836)   GATGATCGCGTGACTGGGAAAATCGAGGCCTTTGCAAGCAGGTCCAAGAT
UT19_Als3     (823)   GATGATCGCGTGACTGGGAAAATCGAGGCCTTTGCAAGCAGGTCCAAGAT
Utopia_Als3_ORF (901) GATGATCGCGTGACTGGGAAAATCGAGGCCTTTGCAAGCAGGTCCAAGAT
Consensus     (901)   GATGATCGCGTGACTGGGAAAATCGAGGCCTTTGCAAGCAGGTCCAAGAT 951                                                 1000
UT15_Als3     (886)   TGTGCACATTGACATTGACCCAGCTGAGATTGGCAAGAACAAGCAGCCAC
UT19_Als3     (873)   TGTGCACATTGACATTGACCCAGCTGAGATTGGCAAGAACAAGCAGCCAC
Utopia_Als3_ORF (951) TGTGCACATTGACATTGACCCAGCTGAGATTGGCAAGAACAAGCAGCCAC
Consensus     (951)   TGTGCACATTGACATTGACCCAGCTGAGATTGGCAAGAACAAGCAGCCAC 1001                                                1050
UT15_Als3     (936)   ATGTCTCCATTTGTGCAGATGTTAAGCTTGCTTTACAGGGGTTGAATGCT
UT19_Als3     (923)   ATGTCTCCATTTGTGCAGATGTTAAGCTTGCTTTACAGGGGTTGAATGCT
Utopia_Als3_ORF (1001) ATGTCTCCATTTGTGCAGATGTTAAGCTTGCTTTACAGGGGTTGAATGCT
Consensus     (1001)  ATGTCTCCATTTGTGCAGATGTTAAGCTTGCTTTACAGGGGTTGAATGCT 1051                                                1100
UT15_Als3     (986)   CTATTAAATGGGAGCAAAGCACAACAGGGTCTGGATTTTGGTCCATGGCA
Utopia19_Als3 (973)   CTATTAAATGGGAGCAAAGCACAACAGGGTCTGGATTTTGGTCCATGGCA
Utopia_Als3_ORF (1051) CTATTAAATGGGAGCAAAGCACAACAGGGTCTGGATTTTGGTCCATGGCA
Consensus     (1051)  CTATTAAATGGGAGCAAAGCACAACAGGGTCTGGATTTTGGTCCATGGCA 1101                                                1150
UT15_Als3     (1036)  CAAGGAGTTGGATCAGCAGAAGAGGGAGTTTCCTCTAGGATTCAAGACTT
UT19_Als3     (1023)  CAAGGAGTTGGATCAGCAGAAGAGGGAGTTTCCTCTAGGATTCAAGACTT
Utopia_Als3_ORF (1101) CAAGGAGTTGGATCAGCAGAAGAGGGAGTTTCCTCTAGGATTCAAGACTT
Consensus     (1101)  CAAGGAGTTGGATCAGCAGAAGAGGGAGTTTCCTCTAGGATTCAAGACTT 1151                                                1200
UT15_Als3     (1086)  TTGGCGAGGCCATCCCGCCGCAATATGCTATCCAGGTACTGGATGAGCTG
UT19_Als3     (1073)  TTGGCGAGGCCATCCCGCCGCAATATGCTATCCAGGTACTGGATGAGCTG
Utopia_Als3_ORF (1151) TTGGCGAGGCCATCCCGCCGCAATATGCTATCCAGGTACTGGATGAGCTG
Consensus     (1151)  TTGGCGAGGCCATCCCGCCGCAATATGCTATCCAGGTACTGGATGAGCTG 1201                                                1250
UT15_Als3     (1136)  ACAAAAGGGGAGGCGATCATTGCTACTGGTGTTGGGCAGCACCAGATGTG
UT19_Als3     (1123)  ACAAAAGGGGAGGCGATCATTGCTACTGGTGTTGGGCAGCACCAGATGTG
Utopia_Als3_ORF (1201) ACAAAAGGGGAGGCGATCATTGCTACTGGTGTTGGGCAGCACCAGATGTG
Consensus     (1201)  ACAAAAGGGGAGGCGATCATTGCTACTGGTGTTGGGCAGCACCAGATGTG 1251                                                1300
UT12_Als3     (1)     -GCGGCTCAGTATTACACTTACAAGCGGCCACGGCAGTGGCTGTCTTCGT
UT15_Als3     (1186)  GGCGGCTCAGTATTACACTTACAAGCGGCCACGGCAGTGGCTGTCTTCGT
UT19_Als3     (1173)  GGCGGCTCAGTATTACACTTACAAGCGGCCACGGCAGTGGCTGTCTTCGT
Utopia_Als3_ORF (1251) GGCGGCTCAGTATTACACTTACAAGCGGCCACGGCAGTGGCTGTCTTCGT
Consensus     (1251)  GGCGGCTCAGTATTACACTTACAAGCGGCCACGGCAGTGGCTGTCTTCGT 1301                                                1350
UT12_Als3     (50)    CTGGTTTGGGGGCAATGGGATTTGGGTTACCAGCTGCAGCTGGCGCTGCT
UT15_Als3     (1236)  CTGGTTTGGGGGCAATGGGATTTGGGTTACCAGCTGCAGCTGGCGCTGCT
UT19_Als3     (1223)  CTGGTTTGGGGGCAATGGGATTTGGGTTACCAGCTGCAGCTGGCGCTGCT
Utopia_Als3_ORF (1301) CTGGTTTGGGGGAATGGGATTTGGGTTACCAGCTGCAGCTGGCGCTGCT
Consensus     (1301)  CTGGTTTGGGGGCAATGGGATTTGGGTTACCAGCTGCAGCTGGCGCTGCT
```

FIG. 5D

```
                              1351                                              1400
    UT12_Als3       (100)    GTGGCCAACCCAGGTGTTACAGTTGTTGACATTGATGGAGATGGTAGTTT
    UT15_Als3      (1286)    GTGGCCAACCCAGGTGTTACAGTTGTTGACATTGATGGAGATGGTAGTTT
    UT19_Als3      (1273)    GTGGCCAACCCAGGTGTTACAGTTGTTGACATTGATGGAGATGGTAGTTT
 Utopia_Als3_ORF   (1351)    GTGGCCAACCCAGGTGTTACAGTTGTTGACATTGATGGAGATGGTAGTTT
       Consensus   (1351)    GTGGCCAACCCAGGTGTTACAGTTGTTGACATTGATGGAGATGGTAGTTT 1401                                              1450
    UT12_Als3       (150)    CCTCATGAACATTCAGGAGTTGGCATTGATCCGTATTGAGAACCTCCCTG
    UT15_Als3      (1336)    CCTCATGAACATTCAGGAGTTGGCATTGATCCGTATTGAGAACCTCCCTG
    UT19_Als3      (1323)    CCTCATGAACATTCAGGAGTTGGCATTGATCCGTATTGAGAACCTCCCTG
 Utopia_Als3_ORF   (1401)    CCTCATGAACATTCAGGAGTTGGCATTGATCCGTATTGAGAACCTCCCTG
       Consensus   (1401)    CCTCATGAACATTCAGGAGTTGGCATTGATCCGTATTGAGAACCTCCCTG 1451                                              1500
    UT12_Als3       (200)    TGAAGGTGATGATATTGAACAACCAGCATCTGGGAATGGTGGTGCAATGG
    UT15_Als3      (1386)    TGAAGGTGATGATATTGAACAACCAGCATCTGGGAATGGTGGTGCAATGG
    UT19_Als3      (1373)    TGAAGGTGATGATATTGAACAACCAGCATCTGGGAATGGTGGTGCAATGG
 Utopia_Als3_ORF   (1451)    TGAAGGTGATGATATTGAACAACCAGCATCTGGGAATGGTGGTGCAATGG
       Consensus   (1451)    TGAAGGTGATGATATTGAACAACCAGCATCTGGGAATGGTGGTGCAATGG 1501                                              1550
    UT12_Als3       (250)    GAGGATAGGTTTTACAAGGCCAATCGGGCGCACACATACCTTGGCAACCC
    UT15_Als3      (1436)    GAGGATAGGTTTTACAAGGCCAATCGGGCGCACACATACCTTGGCAACCC
    UT19_Als3      (1423)    GAGGATAGGTTTTACAAGGCCAATCGGGCGCACACATACCTTGGCAACCC
 Utopia_Als3_ORF   (1501)    GAGGATAGGTTTTACAAGGCCAATCGGGCGCACACATACCTTGGCAACCC
       Consensus   (1501)    GAGGATAGGTTTTACAAGGCCAATCGGGCGCACACATACCTTGGCAACCC 1551                                              1600
    UT12_Als3       (300)    AGAAAATGAGAGTGAGATATATCCAGATTTTGTGACGATTGCTAAAGGAT
    UT15_Als3      (1486)    AGAAAATGAGAGTGAGATATATCCAGATTTTGTGACGATTGCTAAAGGAT
    UT19_Als3      (1473)    AGAAAATGAGAGTGAGATATATCCAGATTTTGTGACGATTGCTAAAGGAT
 Utopia_Als3_ORF   (1551)    AGAAAATGAGAGTGAGATATATCCAGATTTTGTGACGATTGCTAAAGGAT
       Consensus   (1551)    AGAAAATGAGAGTGAGATATATCCAGATTTTGTGACGATTGCTAAAGGAT 1601                                              1650
    UT12_Als3       (350)    TCAACGTTCCGGCAGTTCGTGTGACGAAGAAGAGCGAAGTCACTGCAGCA
    UT15_Als3      (1536)    TCAACGTTCCGGCAGTTCGTGTGACGAAGAAGAGCGAAGTCACTGCAGCA
    UT19_Als3      (1523)    TCAACGTTCCGGCAGTTCGTGTGACGAAGAAGAGCGAAGTCACTGCAGCA
 Utopia_Als3_ORF   (1601)    TCAACGTTCCGGCAGTTCGTGTGACGAAGAAGAGCGAAGTCACTGCAGCA
       Consensus   (1601)    TCAACGTTCCGGCAGTTCGTGTGACGAAGAAGAGCGAAGTCACTGCAGCA 1651                                              1700
    UT12_Als3       (400)    ATCAAGAAGATGCTTGAGACCCCAGGGCCATACTTGTTGGATATCATCGT
    UT15_Als3      (1586)    ATCAAGAAGATGCTTGAGACCCCAGGGCCATACTTGTTGGATATCATCGT
    UT19_Als3      (1573)    ATCAAGAAGATGCTTGAGACCCCAGGGCCATACTTGTTGGATATCATCGT
 Utopia_Als3_ORF   (1651)    ATCAAGAAGATGCTTGAGACCCCAGGGCCATACTTGTTGGATATCATCGT
       Consensus   (1651)    ATCAAGAAGATGCTTGAGACCCCAGGGCCATACTTGTTGGATATCATCGT 1701                                              1750
    UT12_Als3       (450)    CCCGCATCAGGAGCACGTGCTGCCTATGATCCCAAACGGTGGTGCTTTCA
    UT15_Als3      (1636)    CCCGCATCAGGAGCACGTGCTGCCTATGATCCCAAGCGGTGGTGCTTTCA
    UT19_Als3      (1623)    CCCGCATCAGGAGCACGTGCTGCCTATGATCCCAAGCGGTGGTGCTTTCA
 Utopia_Als3_ORF   (1701)    CCCGCATCAGGAGCACGTGCTGCCTATGATCCCAAGCGGTGGTGCTTTCA
       Consensus   (1701)    CCCGCATCAGGAGCACGTGCTGCCTATGATCCCAARCGGTGGTGCTTTCA
```

FIG.5E

```
                         1751                                              1800
      UT12_Als3   (500)  AGGACATGATCATGGAGGGTGATGGCAGGACCTCGTACTGAAATTTCGAC
      UT15_Als3  (1686)  AGGACATGATCATGGAGGGTGATGGCAGGACCTCGTAC-
      UT19_Als3  (1673)  AGGACATGATCATGGAGGGTGATGGCAGGACCTCGTAC-
 Utopia_Als3_ORF (1751)  AGGACATGATCATGGAGGGTGATGGCAGGACCTCGTACTGAAATTTCGAC
      Consensus  (1751)  AGGACATGATCATGGAGGGTGATGGCAGGACCTCGTACTGAAATTTCGAC 1800
      UT12_Als3   (550)  CTACAAGACCTACAAGTGTGACATGC-
      UT15_Als3
      UT19_Als3
 Utopia_Als3_ORF (1801)  CTACAAGACCTACAAGTGTGACATGCC
      Consensus  (1801)  CTACAAGACCTACAAGTGTGACATGCC
```

FIG.6A

```
                        1                                                50
UT15_Als3     (1)   ------------------------RKGADILVEALERCGIVDVFAYPGG SM
UT19_Als3     (1)   ----------------------------DILVEALERCGIVDVFAYPGG SM
Utopia_Als3   (1)   SPAATSAAPPATALRPWGPSEPRKGADILVEALERCGIVDVFAYPGGASM
Consensus     (1)                           RKGADILVEALERCGIVDVFAYPGGTSM 51                                              100
UT15_Als3    (29)   EIHQALTRSPVITNHLFRHEQGEAFAASGYARASGRVGVCVATSGPGATN
UT19_Als3    (25)   EIHQALTRSPVITNHLFRHEQGEAFAASGYARASGRVGVCVATSGPGATN
Utopia_Als3  (51)   EIHQALTRSPVITNHLFRHEQGEAFAASGYARASGRVGVCVATSGPGATN
Consensus    (51)   EIHQALTRSPVITNHLFRHEQGEAFAASGYARASGRVGVCVATSGPGATN 101                                             150
UT15_Als3    (79)   LVSALADALLDSIPMVAITGQVPRRMIGTDAFQETPIVEVTRSITKHNYL
UT19_Als3    (75)   LVSALADALLDSIPMVAITGQVPRRMIGTDAFQETPIVEVTRSITKHNYL
Utopia_Als3 (101)   LVSALADALLDSIPMVAITGQVPRRMIGTDAFQETPIVEVTRSITKHNYL
Consensus   (101)   LVSALADALLDSIPMVAITGQVPRRMIGTDAFQETPIVEVTRSITKHNYL 151                                             200
UT15_Als3   (129)   VLDVEDIPRVIQEAFFLASSGRPGPVLVDIPKDIQQQMAVPIWDTPMSLP
UT19_Als3   (125)   VLDVEDIPRVIQEAFFLASSGRPGPVLVDIPKDIQQQMAVPIWDTPMSLP
Utopia_Als3 (151)   VLDVEDIPRVIQEAFFLASSGRPGPVLVDIPKDIQQQMAVPIWDTPMSLP
Consensus   (151)   VLDVEDIPRVIQEAFFLASSGRPGPVLVDIPKDIQQQMAVPIWDTPMSLP 201                                             250
UT15_Als3   (179)   GYIARLPKPPSTESLEQVLRLVGESRRPILYVGGGCAASGEELRRFVELT
UT19_Als3   (175)   GYIARLPKPPSTESLEQVLRLVGESRRPILYVGGGCAASGEELRRFVELT
Utopia_Als3 (201)   GYIARLPKPPSTESLEQVLRLVGESRRPILYVGGGCAASGEELRRFVELT
Consensus   (201)   GYIARLPKPPSTESLEQVLRLVGESRRPILYVGGGCAASGEELRRFVELT 251                                             300
UT15_Als3   (229)   GIPVTTTLMGLGNFPSDDPLSLRMLGMHGTVYANYAVDKADLLLAFGVRF
UT19_Als3   (225)   GIPVTTTLMGLGNFPSDDPLSLRMLGMHGTVYANYAVDKADLLLAFGVRF
Utopia_Als3 (251)   GIPVTTTLMGLGNFPSDDPLSLRMLGMHGTVYANYAVDKADLLLAFGVRF
Consensus   (251)   GIPVTTTLMGLGNFPSDDPLSLRMLGMHGTVYANYAVDKADLLLAFGVRF 301                                             350
UT15_Als3   (279)   DDRVTGKIEAFASRSKIVHIDIDPAEIGKNKQPHVSICADVKLALQGLNA
UT19_Als3   (275)   DDRVTGKIEAFASRSKIVHIDIDPAEIGKNKQPHVSICADVKLALQGLNA
Utopia_Als3 (301)   DDRVTGKIEAFASRSKIVHIDIDPAEIGKNKQPHVSICADVKLALQGLNA
Consensus   (301)   DDRVTGKIEAFASRSKIVHIDIDPAEIGKNKQPHVSICADVKLALQGLNA 351                                             400
UT15_Als3   (329)   LLNGSKAQQGLDFGPWHKELDQQKREFPLGFKTFGEAIPPQYAIQVLDEL
UT19_Als3   (325)   LLNGSKAQQGLDFGPWHKELDQQKREFPLGFKTFGEAIPPQYAIQVLDEL
Utopia_Als3 (351)   LLNGSKAQQGLDFGPWHKELDQQKREFPLGFKTFGEAIPPQYAIQVLDEL
Consensus   (351)   LLNGSKAQQGLDFGPWHKELDQQKREFPLGFKTFGEAIPPQYAIQVLDEL
```

FIG.6B

```
                    401                                              450
UT12_Als3    (1)            -AAQYYTYKRPRQWLSSSGLGAMGFGLPAAAGAA
UT15_Als3    (379)   TKGEAIIATGVGQHQMWAAQYYTYKRPRQWLSSSGLGAMGFGLPAAAGAA
UT19_Als3    (375)   TKGEAIIATGVGQHQMWAAQYYTYKRPRQWLSSSGLGAMGFGLPAAAGAA
Utopia_Als3  (401)   TKGEAIIATGVGQHQMWAAQYYTYKRPRQWLSSSGLGAMGFGLPAAAGAA
Consensus    (401)   TKGEAIIATGVGQHQMWAAQYYTYKRPRQWLSSSGLGAMGFGLPAAAGAA
                    451                                              500
UT12_Als3    (34)    VANPGVTVVDIDGDGSFLMNIQELALIRIENLPVKVMILNNQHLGMVVQW
UT15_Als3    (429)   VANPGVTVVDIDGDGSFLMNIQELALIRIENLPVKVMILNNQHLGMVVQW
UT19_Als3    (425)   VANPGVTVVDIDGDGSFLMNIQELALIRIENLPVKVMILNNQHLGMVVQW
Utopia_Als3  (451)   VANPGVTVVDIDGDGSFLMNIQELALIRIENLPVKVMILNNQHLGMVVQW
Consensus    (451)   VANPGVTVVDIDGDGSFLMNIQELALIRIENLPVKVMILNNQHLGMVVQW
                    501                                              550
UT12_Als3    (84)    EDRFYKANRAHTYLGNPENESEIYPDFVTIAKGFNVPAVRVTKKSEVTAA
UT15_Als3    (479)   EDRFYKANRAHTYLGNPENESEIYPDFVTIAKGFNVPAVRVTKKSEVTAA
UT19_Als3    (475)   EDRFYKANRAHTYLGNPENESEIYPDFVTIAKGFNVPAVRVTKKSEVTAA
Utopia_Als3  (501)   EDRFYKANRAHTYLGNPENESEIYPDFVTIAKGFNVPAVRVTKKSEVTAA
Consensus    (501)   EDRFYKANRAHTYLGNPENESEIYPDFVTIAKGFNVPAVRVTKKSEVTAA
                    551                                              596
UT12_Als3    (134)   IKKMLETPGPYLLDIIVPHQEHVLPMIPNGGAFKDMIMEGDGRTSY
UT15_Als3    (529)   IKKMLETPGPYLLDIIVPHQEHVLPMIPSGGAFKDMIMEGDGRTSY
UT19_Als3    (525)   IKKMLETPGPYLLDIIVPHQEHVLPMIPSGGAFKDMIMEGDGRTSY
Utopia_Als3  (551)   IKKMLETPGPYLLDIIVPHQEHVLPMIPSGGAFKDMIMEGDGRTSY
Consensus    (551)   IKKMLETPGPYLLDIIVPHQEHVLPMIPXGGAFKDMIMEGDGRTSY
```

WHEAT PLANTS HAVING INCREASED TOLERANCE TO IMIDAZOLINONE HERBICIDES

CROSS-REFERENCE TO RELATED APPLICATIONS

This application is a divisional of U.S. patent application Ser. No. 10/559,161 filed Aug. 14, 2006, which is the U.S. National Stage of International Application PCT/EP2004/005222 filed May 14, 2004, which claims the benefit of U.S. Provisional Application No. 60/473,828 filed May 28, 2003; all of which are hereby incorporated herein in their entirety by reference.

FIELD OF THE INVENTION

The present invention relates in general to plants having an increased tolerance to imidazolinone herbicides. More specifically, the present invention relates to wheat plants obtained by mutagenesis and cross-breeding and transformation that have an increased tolerance to imidazolinone herbicides.

BACKGROUND OF THE INVENTION

Acetohydroxyacid synthase (AHAS; EC 4.1.3.18, acetolactate synthase (ALS)), encoded by the Als nucleic acid, is the first enzyme that catalyzes the biochemical synthesis of the branched chain amino acids valine, leucine, and isoleucine (Singh B. K., 1999, Biosynthesis of valine, leucine and isoleucine in: Singh B. K. (Ed) Plant amino acids. Marcel Dekker Inc. New York, N.Y. Pg 227-247). AHAS is the site of action of four structurally diverse herbicide families including the sulfonylureas (LaRossa R A and Falco S C, 1984, Trends Biotechnol 2:158-161), the imidazolinones (Shaner et al., 1984, Plant Physiol 76:545-546), the triazolopyrimidines (Subramanian and Gerwick, 1989, Inhibition of acetolactate synthase by triazolopyrimidines in (ed) Whitaker J R, Sonnet P E Biocatalysis in agricultural biotechnology. ACS Symposium Series, American Chemical Society. Washington, D.C. Pg 277-288), and the pyrimidyloxybenzoates (Subramanian et al., 1990, Plant Physiol 94: 239-244.). Imidazolinone and sulfonylurea herbicides are widely used in modem agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin), and ARSENAL® (imazapyr). Examples of sulfonylurea herbicides are chlorsulfuron, metsulfuron methyl, suifometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluazsulfuron, imazosulfuron, pyrazosulfuron ethyl, and halosulfuron.

Due to their high effectiveness and low toxicity, imidazolinone herbicides are favored for application by spraying over the top of a wide area of vegetation. The ability to spray an herbicide over the top of a wide range of vegetation decreases the costs associated with plantation establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone tolerant species of the desired vegetation in the spray over area.

Among the major agricultural crops, some leguminous species such as soybean are naturally tolerant to imidazolinone herbicides due to their ability to rapidly metabolize the herbicide compounds (Shaner and Robson, 1985, Weed Sci. 33:469-471). Other crops such as corn (Newhouse et al., 1992, Plant Physiol. 100:882-886) and rice (Barrett et al., 1989, Crop Safeners for Herbicides, Academic Press New York, pp. 195220) are susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al., 1984, Plant Physiol. 76:545-546; Brown et al., 1987, Pestic. Biochm. Physiol. 27:24-29). Other plant physiological differences such as absorption and translocation also play an important role in sensitivity (Shaner and Robson, 1985, Weed Sci. 33:469-471).

Crop cultivars tolerant to imidazolinones, sulfonylureas, and triazolopyrimidines have been successfully produced using seed, microspore, pollen, and callus mutagenesis in *Zea mays, Brassica napus, Glycine max,* and *Nicotiana tabacum* (Sebastian et al., 1989, Crop Sci. 29:1403-1408; Swanson et al., 1989, Theor. Appl. Genet. 78:525-530; Newhouse et al., 1991, Theor. Appl. Genet. 83:65-70; Sathasivan et al., 1991, Plant Physiol. 97:1044-1050; Mourand et al., 1993, J. Heredity 84:91-96). In all cases, a single, partially dominant nuclear gene conferred tolerance. Four imidazolinone tolerant wheat plants were also previously isolated following seed mutagenesis of *Triticum aestivum* L. cv Fidel (Newhouse et al., 1992, Plant Physiol. 100:882-886). Inheritance studies confirmed that a single, partially dominant gene conferred tolerance. Based on allelic studies, the authors concluded that the mutations in the four identified lines were located at the same locus. One of the Fidel cultivar tolerance genes was designated FS-4 (Newhouse et al., 1992, Plant Physiol. 100:882-886).

Computer-based modeling of the three dimensional conformation of the AHAS-inhibitor complex predicts several amino acids in the proposed inhibitor binding pocket as sites where induced mutations would likely confer selective tolerance to imidazolinones (Ott et al., 1996, J. Mol. Biol. 263:359-368) Tobacco plants produced with some of these rationally designed mutations in the proposed binding sites of the AHAS enzyme have in fact exhibited specific tolerance to a single class of herbicides (Ott et al., 1996, J. Mol. Biol. 263:359-368).

Plant tolerance to imidazolinone herbicides has also been reported in a number of patents. U.S. Pat. Nos. 4,761,373, 5,331,107, 5,304,732, 6,211,438, 6,211,439, and 6,222,100 generally describe the use of an altered Als nucleic acid to elicit herbicide tolerance in plants, and specifically disclose certain imidazolinone tolerant corn lines. U.S. Pat. No. 5,013,659 discloses plants exhibiting herbicide tolerance possessing mutations in at least one amino acid in one or more conserved regions. The mutations Described therein encode either cross-tolerance for imidazolinones and sulfonylureas sulfonylurea-specific tolerance, but imidazolinone-specific tolerance is not described. Additionally, U.S. Pat. Nos. 5,731,180 and 5,767,361 discuss an isolated gene having a single amino acid substitution in a wild type monocot AHAS amino acid sequence that results in imidazolinone-specific tolerance.

To date, the prior art has not described imidazolinone tolerant *Triticum turgidum* wheat plants or imidazolinone tolerant triticale plants. The prior art also has not described imidazolinone tolerant plants containing at least one altered *Triticum turgidum* Als nucleic acid. Nor has the prior art described imidazolinone tolerant wheat plants containing mutations on genomes other than the genome from which the FS-4 gene is derived. Therefore, what is needed in the art is the identification of imidazolinone tolerance genes from additional genomes and species. What are also needed in the art are wheat plants and triticale plants having increased tolerance to herbicides such as imidazolinone and containing at least one altered Als nucleic acid. Also needed are methods for controlling weed growth in the vicinity of such wheat plants or triticale plants. These compositions and methods would allow for the use of spray over techniques when applying herbicides to areas containing wheat plants or triticale plants.

SUMMARY OF THE INVENTION

The present invention provides wheat plants comprising IMI nucleic acids, wherein the wheat plant has increased tolerance to an imidazolinone herbicide as compared to a wild-type variety of the plant. The wheat plants can contain one, two, three, or more IMI alleles. In one embodiment, the wheat plant comprises at least one IMI nucleic acid. In another embodiment, the at least one IMI nucleic acid is selected from the group consisting of an Imi 1 nucleic acid, an Imi 2 nucleic acid, and an Imi 3 nucleic acid. In another embodiment, the at least one IMI nucleic acid comprises a *Triticum turgidum* IMI nucleic acid. In another embodiment, the at least one IMI nucleic acid comprises a *Durum* subspecies IMI nucleic acid. In yet another embodiment, the wheat plant comprises multiple IMI nucleic acids located on different genomes. In another embodiment, the multiple IMI nucleic acids comprise a *Triticum turgidum* Imi 2 nucleic acid and a *Triticum turgidum* Imi 3 nucleic acid. In another embodiment, the multiple IMI nucleic acids comprise a *Durum* subspecies Imi 2 nucleic acid and a *Durum* subspecies Imi 3 nucleic acid. Preferably, the IMI nucleic acids encode proteins comprising a mutation in a conserved amino acid sequence selected from the group consisting of a Domain A, a Domain B, a Domain C, a Domain D, and a Domain E. More preferably, the mutation is in a conserved Domain E. Also provided are plant parts and plant seeds derived from the wheat plants described herein.

The present invention also provides triticale plants comprising IMI nucleic acids, wherein the triticale plant has increased tolerance to an imidazolinone herbicide as compared to a wild-type variety of the triticale plant. In one embodiment, the triticale plant comprises at least one IMI nucleic acid. In another embodiment, the at least one IMI nucleic acid is selected from the group consisting of an Imi 1 nucleic acid, an Imi 2 nucleic acid, and an Imi 3 nucleic acid. In another embodiment, the at least one IMI nucleic acid comprises a *Triticum turgidum* IMI nucleic acid. In another embodiment, the at least one IMI nucleic acid comprises a *Durum* subspecies IMI nucleic acid. In yet another embodiment, the wheat plant comprises multiple IMI nucleic acids located on different genomes. In another embodiment, the multiple IMI nucleic acids comprise a *Triticum turgidum* Imi2 nucleic acid and a *Triticum turgidum* Imi 3 nucleic acid. In another embodiment, the multiple IMI nucleic acids comprise a *Durum* subspecies Imi 2 nucleic acid and a *Durum* subspecies Imi 3 nucleic acid. In yet another embodiment, the IMI nucleic acids encode proteins comprising a mutation in a conserved amino acid sequence selected from the group consisting of a Domain A, a Domain B, a Domain C, a Domain D, and a Domain E. More preferably, the mutation is in a conserved Domain E. Also provided are plant parts and plant seeds derived from the triticale plants described herein.

The IMI nucleic acids of the present invention can comprise a nucleotide sequence selected from the group consisting of: a polynucleotide of SEQ ID NO:1, SEQ ID NO:3, SEQ ID NO:5, or SEQ ID NO:23; a polynucleotide that encodes a polypeptide of SEQ ID NO:2, SEQ ID NO:4, SEQ ID NO:6, or SEQ ID NO:24; a polynucleotide comprising at least 60 consecutive nucleotides of any of the aforementioned polynucleotides; and a polynucleotide complementary to any of the aforementioned polynucleotides.

The plants of the present invention can be transgenic or non-transgenic. Examples of non-transgenic wheat plants having increased tolerance to imidazolinone herbicides include a wheat plant having an ATCC Patent Deposit Designation Number PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, or PTA-4960; or a mutant, recombinant, or genetically engineered derivative of the plant with ATCC Patent Deposit Designation Number PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, or PTA-4960; or of any progeny of the plant with ATCC Patent Deposit Designation Number PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, or PTA-4960; or a plant that is a progeny of any of these plants.

In addition to the compositions of the present invention, several methods are provided. Described herein are methods of modifying a plant's tolerance to an imidazolinone herbicide comprising modifying the expression of an IMI nucleic acid in the plant. Also described are methods of producing a transgenic plant having increased tolerance to an imidazolinone herbicide comprising, transforming a plant cell with an expression vector comprising one or more IMI nucleic acids and generating the plant from the plant cell. The invention further includes a method of controlling weeds within the vicinity of a plant, comprising applying an imidazolinone herbicide to the weeds and to the plant, wherein the plant has increased tolerance to the imidazolinone herbicide as compared to a wild type variety of the plant, and wherein the plant comprises one or more IMI nucleic acids. In some preferred embodiments of these methods, the plants comprise multiple IMI nucleic acids that are located on different wheat genomes.

BRIEF DESCRIPTION OF THE DRAWINGS

FIG. 1A-FIG. 1D show a DNA sequence alignment of the Als 2 gene amplified from genomic DNA from the *Durum* wheat variety Ciccio (SEQ ID NO:11), the Als 2 gene amplified from genomic DNA from the *Durum* wheat variety Colosseo (SEQ ID NO:14), the Als 2 gene amplified from genomic DNA from the *Durum* wheat variety Utopia (SEQ ID NO:16), and a *Durum* wheat Als 2 gene consensus sequence (SEQ ID NO:19). There are no polymorphisms among the varieties.

FIG. 2A-FIG. 2D show a DNA sequence alignment of the Als 3 gene amplified from genomic DNA from the *Durum* wheat variety Ciccio (SEQ ID NO:13), the Als 3 gene amplified from genomic DNA from the *Durum* wheat variety Colosseo (SEQ ID NO:15), the Als 3 gene amplified from genomic DNA from the *Durum* wheat variety Utopia (SEQ ID NO:17), and a *Durum* wheat Als 3 gene consensus sequence (SEQ ID NO:21). There are no polymorphisms among the varieties.

FIG. 3A-FIG. 3E show a DNA sequence alignment of the Als 2 gene amplified from genomic DNA from the Ciccio variety (SEQ ID NO:11), the Als 2 gene amplified from genomic DNA from the imidazolinone tolerant CI19 line (SEQ ID NO:1), the Als 2 gene amplified from genomic DNA from the imidazolinone tolerant UT15 line (SEQ ID NO:7), the Als 2 gene amplified from genomic DNA from the imidazolinone tolerant UT19 line (SEQ ID NO:9) and a *Durum* wheat Als 2 gene consensus sequence (SEQ ID NO:19). The nucleotide polymorphism conferring the imidazolinone tolerance to the C119 line is indicated in bold.

FIG. 4A-FIG. 4B show an amino acid sequence alignment of the deduced amino acid sequence of the protein encoded by the Als 2 gene from the Ciccio variety (SEQ ID NO:12), the deduced amino acid sequence of the protein encoded by the Als 2 gene from the imidazolinone tolerant C119 line (SEQ ID NO:2), the deduced amino acid sequence of the protein encoded by the Als 2 gene from the imidazolinone tolerant UT15 line (SEQ ID NO:8), the deduced amino acid sequence of the protein encoded by the Als 2 gene from the imidazolinone tolerant UT19 line (SEQ ID NO:10), and a *Durum* wheat Als 2 consensus sequence (SEQ ID NO:20). The polymorphism conferring the imidazolinone tolerance to the C119 line is indicated in bold.

FIG. 5A-FIG. 5E show a DNA sequence alignment of the Als 3 gene amplified from genomic DNA from the Utopia variety (SEQ ID NO:17), the partial Als 3 polynucleotide sequence amplified from genomic DNA from the imidazolinone tolerant UT12 line (SEQ ID NO:3), the Als 3 gene amplified from genomic DNA from the imidazolinone tolerant UT15 line (SEQ ID NO:5), the Als 3 gene amplified from genomic DNA from the imidazolinone tolerant UT19 line (SEQ ID NO:23), and a *Durum* wheat Als 3 gene consensus sequence (SEQ ID NO:21). The nucleotide polymorphisms conferring the imidazolinone tolerance to the lines are indicated in bold.

FIG. 6A and FIG. 6B show an amino acid sequence alignment of the deduced amino acid sequence of the protein encoded by the Als 3 gene from the Utopia variety (SEQ ID NO:18), the deduced amino acid sequence of the polypeptide encoded by the partial Als 3 polynucleotide sequence from the imidazolinone tolerant UT12 line (SEQ ID NO:4), the deduced amino acid sequence of the protein encoded by the Als 3 gene from the imidazolinone tolerant UT15 line (SEQ ID NO:6), the deduced amino acid sequence of the protein encoded by the Als 3 gene from the imidazolinone tolerant UT19 line (SEQ ID NO:24), and a *Durum* wheat Als 3 consensus sequence (SEQ ID NO:22). The nucleotide polymorphism conferring the imidazolinone tolerance to the UT12 line is indicated in bold.

DETAILED DESCRIPTION

Figure 7:
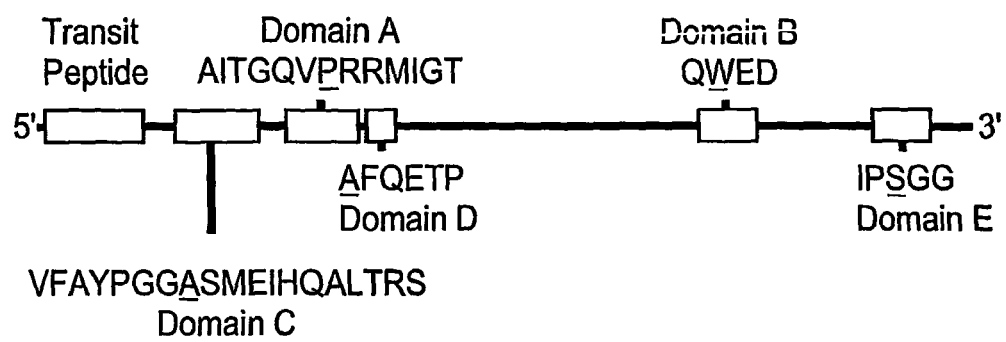
FIG. 7 is a schematic representation of the conserved amino acid sequences in the AHAS genes implicated in tolerance to various AHAS inhibitors. The specific amino acid site responsible for tolerance is indicated by an underline. (Modified from Devine, M. D. and Eberlein, C. V., 1997, Physiological, biochemical and molecular aspects of herbicide tolerance based on altered target sites in Herbicide Activity: Toxicity, Biochemistry, and Molecular Biology, IOS Press Amersterdam, p. 159-185).

The present invention is directed to wheat plants, wheat plant parts, and wheat plant cells having increased tolerance to imidazolinone herbicides. The present invention also includes seeds produced by the wheat plants described herein and methods for controlling weeds in the vicinity of the wheat plants described herein. It is to be understood that as used in the specification and in the claims, "a" or "an" can mean one or more, depending upon the context in which it is used. Thus, for example, reference to "a cell" can mean that at least one cell can be utilized.

As used herein, the term "wheat plant" refers to a plant that is a member of the *Triticum* genus. The wheat plants of the present invention can be members of a *Triticum* genus including, but not limited to, *T. aestivum, T. turgidum, T. timopheevii, T. monococcum, T. zhukovskyi,* and *T. urartu,* and hybrids thereof. Examples of *T. aestivum* subspecies included within the present invention are *aestivum* (common wheat), *compactum* (club wheat), *macha* (*macha* wheat), *vavilovi* (*vavilovi* wheat), *spelta,* and *sphaecrococcum* (shot wheat). Examples of *T. turgidum* subspecies included within the present invention are *turgidum, carthlicum, dicoccom, durum, paleocolchicum, polonicum, turanicum,* and *dicoccoides.* Examples of *T. monococcum* subspecies included within the present invention are *monococcum* (einkom) and *aegilopoides.* In one embodiment of the present invention, the wheat plant is a member of the *Triticum turgidum* species; and in particular, a member of the *Durum* subspecies, for example, a Ciccio, Colosseo, or Utopia cultivar.

The term "wheat plant" is intended to encompass wheat plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like. The present invention also includes seeds produced by the wheat plants of the present invention. In one embodiment, the seeds are true breeding for an increased tolerance to an imidazolinone herbicide as compared to a wild type variety of the wheat plant seed.

The present invention also encompasses triticale plants, triticale plant parts, and tritcale plant cells having increased tolerance to imidazolinone herbicides. As used herein, a "triticale plant" refers to a plant that is created by crossing a rye plant (*Secale cereale*) with either a tetraploid wheat plant (e.g. *Triticum turgidum*) or a hexaploid wheat plant (e.g. *Triticum aestivum*). The present invention also includes seeds produced by the triticale plants described herein and methods for controlling weeds in the vicinity of the triticale plants described herein.

The present invention describes a wheat plant comprising at least one IMI nucleic acid, wherein the wheat plant has increased tolerance to an imidazolinone herbicide as compared to a wild type variety of the plant. It is possible for the wheat plants of the present invention to have multiple IMI nucleic acids from different genomes since these plants can contain more than one genome. For example, a *Triticum turgidum* wheat plant contains two genomes, usually referred to as the A and B genomes. Because AHAS is a required metabolic enzyme, it is assumed that each genome has at least one gene coding for the AHAS enzyme (i.e. at least one Als gene), commonly seen with other metabolic enzymes in tetraploid wheat that have been mapped. As used herein, the term "Als gene locus" refers to the position of an Als gene on a genome, and the terms "Als gene" and "Als nucleic acid" refer to a nucleic acid encoding the AHAS enzyme. The Als nucleic acid on each genome differs in its nucleotide sequence from an Als nucleic acid on another genome. One of skill in the art can determine the genome of origin of each Als nucleic acid through genetic crossing and/or either sequencing methods or exonuclease digestion methods known to those of skill in the art. As used herein, the terms "Als 1 nucleic acid," "Als 2 nucleic acid," and "Als 3 nucleic acid" refer to Als nucleic acids located on three different genomes. For the purposes of this invention, the Als 3 gene locus is located on the A genome, and the Als 2 gene locus is located on the B genome. Also for the purposes of this invention, IMI nucleic acids derived from the A or B genomes are distinguished and designated as Imi 3 or Imi 2 nucleic acids, respectively.

As used herein, the term "IMI nucleic acid" refers to an Als nucleic acid having a sequence that is mutated from a wild type Als nucleic acid and that confers increased imidazolinone tolerance to a plant in which it is expressed. As used herein, the terms "Imi 1 nucleic acid," "Imi 2 nucleic acid," and "Imi 3 nucleic acid" are IMI nucleic acids that refer to the imidazolinone tolerance alleles of the Als 1, Als 2, and Als 3 genes, respectively. Because wheat plants have two copies of each genome, a wheat plant contains two copies of each particular Als nucleic acid. For example, a *Triticum turgidum* wheat plant comprises two copies of the A and B genomes, and therefore two copies each of the Als 3 and Als 2 genes. As used herein, the term "IMI allele" refers to a single copy of a particular IMI nucleic acid. Accordingly, for the purposes of the present invention, a wheat plant may have two Imi 2 alleles, one on each of two copies of the B genome.

In another embodiment, the wheat plant comprises multiple IMI nucleic acids. As used herein, when describing a plant that comprises "multiple IMI nucleic acids," the phrase "multiple IMI nucleic acids" refers to the presence of different IMI nucleic acids in the plant and not to whether the plant is homozygous or heterozygous at a particular Als locus. For example, a plant comprising multiple IMI nucleic acids may comprise an Imi 2 and an Imi 3 nucleic acid, as opposed to having two copies of an Imi 2 nucleic acid.

The Imi 2 class of nucleic acids includes the Imi 2 nucleic acid from the C119, UT01, UT03, UT05, UT07, UT08, UT10, UT13, UT14, UT16, UT17, and UT20 lines described below. The Imi 3 class of nucleic acids includes the Imi 3 nucleic acid from the UT12, UT15, and UT19 lines described below. Each Imi class can include members from different wheat species. Therefore, each Imi class includes IMI nucleic acids that differ in their nucleotide sequence but that are nevertheless designated as originating from, or being located on, the same wheat genome using inheritance studies as known to those of ordinary skill in the art.

Accordingly, the present invention includes a wheat plant comprising at least one IMI nucleic acid, wherein the wheat plant has increased tolerance to an imidazolinone herbicide, as compared to a wild-type variety of the plant and wherein the at least one IMI nucleic acid is selected from a group consisting of an Imi 1 nucleic acid, an Imi 2 nucleic acid, and an Imi 3 nucleic acid. In one embodiment, the plant comprises both an Imi 2 nucleic acid and an Imi 3 nucleic acid. In a preferred embodiment, the Imi 2 nucleic acid comprises the polynucleotide sequence of SEQ ID NO:1. In another preferred embodiment, the Imi 3 nucleic acid comprises the polynucleotide sequence of SEQ ID NO:3, SEQ ID NO:5, or SEQ ID NO:23.

The present invention also encompasses an imidazolinone tolerant triticale plant. As used herein, a "triticale plant" refers to a plant that is created by crossing a rye plant (*Secale cereale*) with either a tetraploid wheat plant (e.g. *Triticum turgidum*) or a hexaploid wheat plant (e.g. *Triticum aestivum*). For the purposes of the present invention, an imidazolinone tolerant triticale plant comprises at least one IMI nucleic acid, wherein the triticale plant has increased tolerance to an imidazolinone herbicide as compared to a wild-type variety of the plant and wherein the at least one IMI nucleic acid is selected from a group consisting of an Imi 1 nucleic acid, an Imi 2 nucleic acid, and an Imi 3 nucleic acid. In one embodiment, the plant comprises both an Imi 2 nucleic acid and an Imi 3 nucleic acid. In a preferred embodiment, the Imi 2 nucleic acid comprises the polynucleotide sequence of SEQ ID NO:1. In another preferred embodiment, the Imi 3 nucleic acid comprises the polynucleotide sequence of SEQ ID NO:3, SEQ ID NO:5, or SEQ ID NO:23.

As used herein with regard to nucleic acids, the term "from" refers to a nucleic acid "located on" or "derived from" a particular genome. The term "located on" refers to a nucleic acid contained within that particular genome. As also used herein with regard to a genome, the term "derived from" refers to a nucleic acid that has been removed or isolated from that genome. The term "isolated" is defined in more detail below.

The present invention includes wheat plants comprising one, two, three, or more IMI alleles, wherein the wheat plant has increased tolerance to an imidazolinone herbicide as compared to a wild-type variety of the plant. The IMI alleles can comprise a nucleotide sequence selected from the group consisting of a polynucleotide as defined in SEQ ID NO:1, SEQ ID NO:3, SEQ ID NO:5, or SEQ ID NO:23; a polynucleotide encoding a polypeptide as defined in SEQ ID NO:2, SEQ ID NO:4, SEQ ID NO:6, or SEQ ID NO:24; a polynucleotide comprising at least 60 consecutive nucleotides of any of the aforementioned polynucleotides; and a polynucleotide complementary to any of the aforementioned polynucleotides. The present invention also includes triticale plants comprising one, two, three, or more IMI alleles, wherein the triticale plant has increased tolerance to an imidazolinone herbicide as compared to a wild-type variety of the plant. The IMI alleles can comprise a nucleotide sequence selected from the group consisting of a polynucleotide as defined in SEQ ID NO:1, SEQ ID NO:3, SEQ ID NO:5, or SEQ ID NO:23; a polynucleotide encoding a polypeptide as defined in SEQ ID NO:2, SEQ ID NO:4, SEQ ID NO:6, or SEQ ID NO:24; a polynucleotide comprising at least 60 consecutive nucleotides of any of the aforementioned polynucleotides; and a polynucleotide complementary to any of the aforementioned polynucleotides.

In one embodiment, the wheat plant or triticale plant comprises two different IMI nucleic acids, wherein the nucleic acids are derived from or located on different wheat genomes. Preferably, the two nucleic acids are an Imi 2 nucleic acid and an Imi 3 nucleic acid. More preferably, the Imi 2 nucleic acid comprises the polynucleotide sequence of SEQ ID NO:1, and the Imi 3 nucleic acid comprises the polynucleotide sequence of SEQ ID NO:3, SEQ ID NO:5, or SEQ ID NO:23. In another embodiment, the wheat plant or triticale plant comprises one IMI nucleic acid, wherein the nucleic acid comprises the polynucleotide sequence of SEQ ID NO:1, SEQ ID NO:3, SEQ ID NO:5, or SEQ ID NO:23. In yet another embodiment, the wheat plant comprises greater than two IMI nucleic acids wherein each IMI nucleic acid is from a different genome. Preferably, at least one of the IMI nucleic acids comprises a polynucleotide sequence selected from the group consisting of SEQ ID NO:1, SEQ ID NO:3, SEQ ID NO:5, or SEQ ID NO:23.

In a preferred embodiment of the present invention, the isolated IMI nucleic acid encodes an amino acid sequence comprising a mutation in a domain that is conserved among several AHAS proteins. These conserved domains are referred to herein as Domain A, Domain B, Domain C, Domain D, and Domain E. FIG. 7 shows the general location of each domain in an AHAS protein. Domain A contains the amino acid sequence AITGQVPRRMIGT (SEQ ID NO:25). Domain B contains the amino acid sequence QWED (SEQ ID NO:26). Domain C contains the amino acid sequence VFAYPGGASMEIHQALTRS (SEQ ID NO:27). Domain D contains the amino acid sequence AFQETP (SEQ ID NO:28). Domain E contains the amino acid sequence IPSGG (SEQ ID NO:29). The present invention also contemplates that there may be slight variations in the conserved domains, for example, in cockleber plants, the serine residue in Domain E is replaced by an alanine residue.

Accordingly, the present invention includes a wheat plant comprising an IMI nucleic acid that encodes an amino acid sequence having a mutation in a conserved domain selected from the group consisting of a Domain A, a Domain B, a Domain C, a Domain D, and a Domain E. In one embodiment, the wheat plant comprises an IMI nucleic acid that encodes an amino acid sequence having a mutation in a Domain E. In further preferred embodiments, the mutations in the conserved domains occur at the locations indicated by the following underlining: AITGQV<u>P</u>RRMIGT (SEQ ID NO:25); Q<u>W</u>ED (SEQ ID NO:26); VFAYPGG<u>A</u>SMEIHQALTRS (SEQ ID NO:27); <u>A</u>FQETP (SEQ ID NO:28), and IP<u>S</u>GG (SEQ ID NO:29). One preferred substitution is asparagine for serine in Domain E.

The imidazolinone herbicide can be selected from, but is not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, or a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidazolin-2-yl)-nicotinic acid, 2-(4-isopropyl)-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate, and methyl 2-(4-isopropyl-4-methyl-5-oxo-2-imidazolin-2-yl)-p-toluate. The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5-(methoxymethyl)-nicotinic acid is particularly preferred.

The wheat plants described herein can be either transgenic wheat plants or non-transgenic wheat plants. Similarly, the triticale plants described herein can be either transgenic triticale plants or non-transgenic triticale plants. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding. Plants containing mutations arising due to non-spontaneous mutagenesis and selective breeding are referred to herein as non-transgenic plants and are included in the present invention. In embodiments wherein the wheat plant is transgenic and comprises multiple IMI nucleic acids, the nucleic acids can be derived from different genomes or from the same genome. Alternatively, in embodiments wherein the wheat plant is non-transgenic and comprises multiple IMI nucleic acids, the nucleic acids are located on different genomes or on the same genome.

An example of a non-transgenic wheat plant line comprising one IMI nucleic acid is the plant line deposited with the ATCC under Patent Deposit Designation Number PTA-4960 and designated herein as the C119 wheat line. The C119 wheat line contains an Imi 2 nucleic acid. The nucleotide sequence corresponding to the C119 Als 2 gene locus is shown in SEQ ID NO:1. Other examples of non-transgenic wheat plant lines comprising one IMI nucleic acid are the plant lines deposited with the ATCC under Patent Deposit Designation Numbers PTA-4910, PTA-4911, PTA-4912, PTA-4913, PTA-4914, PTA-4915, PTA-4917, PTA-4918, PTA-4920, PTA-4921, PTA-4923, and PTA-4960; and designated herein as the UT01, UT03, UT05, UT07, UT08, UT10, UT13, UT14, UT16, UT17, and UT20 lines, respectively. The nucleotide sequence corresponding to the Als 2 gene locus in the UT01, UT03, UT05, UT07, UT08, UT10, UT13, UT14, UT16, UT17, and UT20 lines is identical to the polynucleotide sequence as defined in SEQ ID NO:1.

Another example of a non-transgenic wheat plant line comprising one IMI nucleic acid is the plant line deposited with the ATCC under Patent Deposit Designation Number PTA-4916 and designated herein as the UT12 wheat line. The UT12 wheat line contains an Imi 3 nucleic acid. The nucleotide sequence corresponding to the Als 3 gene locus in the UT12 line is shown in SEQ ID NO:3.

Another example of a non-transgenic wheat plant line comprising one IMI nucleic acid is the plant line deposited with the ATCC under Patent Deposit Designation Number PTA-4919 and designated herein as the UT15 wheat line. The UT15 wheat line contains an Imi 3 nucleic acid. The nucleotide sequence corresponding to the Als 3 gene locus in the UT15 line is shown in SEQ ID NO:5. Another example of a non-transgenic wheat plant line comprising one IMI nucleic acid is the plant line deposited with the ATCC under Patent Deposit Designation Number PTA-4922. The nucleotide sequence corresponding to the Als 3 gene locus in the UT19 line is identical to the polynucleotide sequence as defined in SEQ ID NO:23.

Separate deposits of about 2500 seeds each of the imidazolinone tolerant wheat lines were made with the American Type Culture Collection, Manassas, Va. on Jan. 7, 2003 and Jan. 28, 2003. These deposits were made in accordance with the terms and provisions of the Budapest Treaty relating to the deposit of microorganisms. The deposits were made for a term of at least thirty years and at least five years after the most recent request for the furnishing of a sample of the deposit is received by the ATCC. The deposited seeds were accorded Patent Deposit Designation Numbers PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, and PTA-4960.

The present invention includes the wheat plant having a Patent Deposit Designation Number PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, or PTA-4960; a mutant, recombinant, or genetically engineered derivative of the plant with Patent Deposit Designation Number PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, or PTA-4960; any progeny of the plant with Patent Deposit Designation Number PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, or PTA-4960; and a plant that is the progeny of any of these plants. In a preferred embodiment, the wheat plant of the present invention additionally has the herbicide tolerance characteristics of the plant with Patent Deposit Designation Number PTA-4910, PTA-4911, PTA-4912, PTA-4913, PTA-4914, PTA-4915, PTA-4916, PTA-4917, PTA-4918, PTA-4919, PTA-4920, PTA-4921, PTA-4922, PTA-4923, and PTA-4960.

Also included in the present invention are hybrids of the wheat plants described herein and another wheat plant. The other wheat plant includes, but is not limited to, *T. aestivum* L. cv Fidel and any wheat plant harboring a mutant gene FS-1, FS-2, FS-3 or FS-4. (See U.S. Pat. No. 6,339,184 and U.S. patent application Ser. No. 08/474,832). Preferred hybrids contain a combination of Imi 1, Imi 2, and/or Imi 3 nucleic acids.

The terms "cultivar" and "variety" refer to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or 'line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in an Als gene of the wheat or triticale plant or seed.

It is to be understood that the wheat or triticale plant of the present invention can comprise a wild type Als nucleic acid in addition to an IMI nucleic acid. It is contemplated that the imidazolinone tolerant lines may contain a mutation in only one of multiple AHAS isoenzymes. Therefore, the present invention includes a wheat or triticale plant comprising one or more IMI nucleic acids in addition to one or more wild type Als nucleic acids.

In addition to wheat and triticale plants, the present invention encompasses isolated IMI proteins and nucleic acids. The nucleic acids comprise a polynucleotide selected from the group consisting of a polynucleotide of SEQ ID NO:1, SEQ ID NO:3, SEQ ID NO:5, or SEQ ID NO:23; a polynucleotide encoding a polypeptide of SEQ ID NO:2, SEQ ID NO:4, SEQ ID NO:6, or SEQ ID NO:24; a polynucleotide comprising at least 60 consecutive nucleotides of any of the aforementioned polynucleotides; and a polynucleotide complementary to any of the aforementioned polynucleotides. In a preferred embodiment, the IMI nucleic acid comprises a polynucleotide sequence of SEQ ID NO:1. In another preferred embodiment, the IMI nucleic acid comprises a polynucleotide sequence of SEQ ID NO:3. In yet another preferred embodiment, the IMI nucleic acid comprises a polynucleotide sequence of SEQ ID NO:5.

The term "AHAS protein" or "AHAS polypeptide" refers to a wild type acetohydroxy acid synthase protein, and the term "IMI protein" refers to any AHAS protein that is mutated from a wild type AHAS protein and that confers increased imidazolinone tolerance to a plant, plant cell, plant part, plant seed, or plant tissue when it is expressed therein. In a preferred embodiment, the IMI protein comprises a polypeptide encoded by a polynucleotide sequence comprising SEQ ID NO:1. In another preferred embodiment, the IMI protein comprises a polypeptide encoded by a polynucleotide sequence comprising SEQ ID NO:3. In still another preferred embodiment, the IMI protein comprises a polypeptide encoded by a polynucleotide sequence comprising SEQ ID NO:5 or SEQ ID NO:23. As also used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypokanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated IMI nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Triticum turgidum* cell). A nucleic acid is also considered isolated if it has been altered by human intervention, or placed in a locus or location that is not its natural site, or if it is introduced into a cell by agroinfection, biolistics, or any other method of plant transformation. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally—occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule containing a nucleotide sequence of SEQ ID NO:1, SEQ ID NO:3, SEQ ID NO:5, or SEQ ID NO:23, or a portion thereof, can be isolated using standard molecular biology techniques and the sequence information provided herein. For example, a *T. turgidum* IMI cDNA can be isolated from a *T. turgidum* library using all or a portion of the sequence of SEQ ID NO:1, SEQ ID NO:3, SEQ ID NO:5, or SEQ ID NO:23. Moreover, a nucleic acid molecule encompassing all or a portion of SEQ ID NO:1, SEQ ID NO:3, SEQ ID NO:5, or SEQ ID NO:23 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gib-Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1, SEQ ID NO:3, SEQ ID NO:5, or SEQ ID NO:23. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an IMI nucleotide sequence can be prepared by standard synthetic techniques, e.g., using an automated DNA synthesizer.

The IMI nucleic acids of the present invention can comprise sequences encoding an IMI protein (i.e., "coding regions"), as well as 5' untranslated sequences and 3' untranslated sequences. Alternatively, the nucleic acid molecules of the present invention can comprise only the coding regions of an IMI gene, or can contain whole genomic fragments isolated from genomic DNA. A coding region of these sequences is indicated as an "ORF position." Moreover, the nucleic acid molecule of the invention can comprise a portion of a coding region of an IMI gene, for example, a fragment that can be used as a probe or primer. The nucleotide sequences determined from the cloning of the IMI genes from *T. turgidum* allow for the generation of probes and primers designed for use in identifying and/or cloning IMI homologs in other cell types and organisms, as well as IMI homologs from other wheat plants and related species. The portion of the coding region can also encode a biologically active fragment of an IMI protein.

As used herein, the term "biologically active portion of an IMI protein is intended to include a portion, e.g., a domain/motif, of an IMI protein that, when produced in a plant increases the plant's tolerance to an imidazolinone herbicide as compared to a wild-type variety of the plant. Methods for quantitating increased tolerance to imidazolinone herbicides are provided in the Examples below. Biologically active portions of an IMI protein include peptides derived from SEQ ID NO:2, SEQ ID NO:4, SEQ ID NO:6, or SEQ ID NO:24 which include fewer amino acids than a full length IMI protein and impart increased tolerance to an imidazolinone herbicide upon expression in a plant. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an IMI protein. Moreover, other biologically active portions in which other regions of the polypeptide are deleted, can be prepared by recombinant techniques and evaluated for one or more of the activities described herein. Preferably, the biologically active portions of an IMI protein include one or more conserved domains selected from the group consisting of a Domain A, a Domain B, a Domain C, a Domain D, and a Domain E, wherein the conserved domain contains a mutation.

The invention also provides IMI chimeric or fusion polypeptides. As used herein, an IMI "chimeric polypeptide" or "fusion polypeptide" comprises an IMI polypeptide operatively linked to a non-IMI polypeptide. A "non-IMI polypeptide" refers to a polypeptide having an amino acid sequence that is not substantially identical to an IMI polypeptide, e.g., a polypeptide that is not an IMI isoenzyme, which peptide performs a different function than an IMI polypeptide. As used herein with respect to the fusion polypeptide, the term "operatively linked" is intended to indicate that the IMI polypeptide and the non-IMI polypeptide are fused to each other so that both sequences fulfill the proposed function attributed to the sequence used. The non-IMI polypeptide can be fused to the N-terminus or C-terminus of the IMI polypeptide. For example, in one embodiment, the fusion polypeptide is a GST-IMI fusion polypeptide in which the IMI sequence is fused to the C-terminus of the GST sequence. Such fusion polypeptides can facilitate the purification of recombinant IMI polypeptides. In another embodiment, the fusion polypeptide is an IMI polypeptide containing a heterologous signal sequence at its N-terminus. In certain host cells (e.g., mammalian host cells), expression and/or secretion of an IMI polypeptide can be increased through use of a heterologous signal sequence.

An isolated nucleic acid molecule encoding an IMI polypeptide having sequence identity to a polypeptide encoded by a polynucleotide sequence of SEQ ID NO:1, SEQ ID NO:3, SEQ ID NO:5, or SEQ ID NO:23 can be created by introducing one or more nucleotide substitutions, additions, or deletions into a nucleotide sequence of SEQ ID NO:1, SEQ ID NO:3, SEQ ID NO:5, or SEQ ID NO:23 such that one or more amino acid substitutions, additions, or deletions are introduced into the encoded polypeptide. Mutations can be introduced into a sequence of SEQ ID NO:1, SEQ ID NO:3, SEQ ID NO:5, or SEQ ID NO:23 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted non-essential amino acid residue in an IMI polypeptide is preferably replaced with another amino acid residue from the same side chain family. Alternatively, in another embodiment, mutations can be introduced randomly along all or part of an IMI coding sequence, such as by saturation mutagenesis, and the resultant mutants can be screened for an IMI activity described herein to identify mutants that retain IMI activity. Following mutagenesis of the sequence of SEQ ID NO:1, SEQ ID NO:3, SEQ ID NO:5, or SEQ ID NO:23, the encoded polypeptide can be expressed recombinantly and the activity of the polypeptide can be determined by analyzing the imidazolinone tolerance of a plant expressing the polypeptide as described in the Examples below.

To determine the percent sequence identity of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings.

It is to be understood that for the purposes of determining sequence identity, when comparing a DNA sequence to an RNA sequence, a thymidine nucleotide is equivalent to a uracil nucleotide. Preferably, the isolated IMI polypeptides included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2, SEQ ID NO:4, SEQ ID NO:6, or SEQ ID NO:24. In another embodiment, the isolated IMI polypeptides included in the present invention are at least about 50-60%, preferably at least about 60-70%, and more preferably at least about 70-75%; 75-80%, 80-85%, 85-90%, or 90-95%, and most preferably at least about 96%, 97%, 98%, 99%, or more identical to an entire amino acid sequence shown in SEQ ID NO:2, SEQ ID NO:4, SEQ ID NO:6, or SEQ ID NO:24. Additionally, optimized IMI nucleic acids can be created. Preferably, an optimized IMI nucleic acid encodes an IMI polypeptide that modulates a plant's tolerance to imidazolinone herbicides, and more preferably increases a plant's tolerance to an imidazolinone herbicide upon its overexpression in the plant. As used herein, "optimized" refers to a nucleic acid that is genetically engineered to increase its expression in a given plant or animal. To provide plant optimized IMI nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) eliminate sequences that cause destabilization, inappropriate polyadenylation, degradation and termination of RNA, or that form secondary structure hairpins or RNA splice sites. Increased expression of IMI nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. Nos. 5,380,831; 5,436,391; Perlack et al., 1991, Proc. Natl. Acad. Sci. USA 88:3324-3328; and Murray et al., 1989, Nucleic Acids Res. 17:477-498.

As used herein; "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation 1A=n=1 Z Xn−Yn Xn times 100 Z where Xn=frequency of usage for codon n in the host cell; Yn=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, an IMI nucleic acid can be optimized. such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position; whereas dicotyledons do not). it is also recognized that the XCG (where X is A, T, C, or G) nucleotide is the least preferred codon in dicots whereas the XTA codon is avoided in both monocots and dicots. Optimized IMI nucleic acids of this invention also preferably have CG and TA doublet avoidance indices closely approximating those of the chosen host plant (i.e., *Triticum turgidum*). More preferably these indices deviate from that of the host by no more than about 10-15%.

In addition to the nucleic acid molecules encoding the IMI polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide sequence of SEQ ID NO:2, SEQ ID NO:4, SEQ ID NO:6, or SEQ ID NO:24.

In addition to the IMI nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of the sequence set forth in SEQ ID NO:1, SEQ ID NO:3, SEQ ID NO:5, or SEQ ID NO:23, an anti-sense sequence of the sequence set forth in SEQ ID NO:1, SEQ ID NO:3, SEQ ID NO:5, or SEQ ID NO:23, or naturally occurring mutants thereof. Primers based on a nucleotide sequence of SEQ ID NO:1, SEQ ID NO:3, SEQ ID NO:5, or SEQ ID NO:23 can be used in PCR reactions to clone IMI homologs. Probes based on the IMI nucleotide sequences can be used to detect transcripts or genomic sequences encoding the same or homologous polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an IMI polypeptide, such as by measuring a level of an IMI-encoding nucleic acid, in a sample of cells, e.g., detecting IMI mRNA levels or determining whether a genomic IMI pane has beer, mutated or deleted.

The invention further provides an isolated recombinant expression vector comprising an IMI nucleic acid as described above, wherein expression of the vector in a host cell results in increased tolerance to an imidazolinone herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. With respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., IMI polypeptides, fusion polypeptides, etc.).

In a preferred embodiment of the present invention, the IMI polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). An IMI polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As increased tolerance to imidazolinone herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. In a preferred embodiment, the plant is a wheat plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of an IMI polynucleotide into a plant is achieved by Agrobacterium mediated gene transfer. One transformation method known to those of skill in the art is the dipping of a flowering plant into an Agrobacteria solution, wherein the Agrobacteria contains the IMI nucleic acid, followed by breeding of the transformed gametes. Agrobacterium mediated plant transformation can be performed using for example the GV3101(pMP90) (Koncz and Schell, 1986, Mol. Gen. Genet. 204:383-396) or LBA4404 (Clontech) Agrobacterium tumefaciens strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur BT11-P ISBN 07923-2731-4; Giick, Bernard R. and Thompson, John E., Methods in Plant Molecular Biology and Biotechnology, Boca Raton: CRC Press, 1993 360 S., ISBN 0-8493-51642). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced IMI polynucleotide may be maintained in the plant cell stably if it is incorporated into a non-chromosomal autonomous replicon or integrated into the plant chromosomes. Alternatively, the introduced IMI polynucleotide may be present on an extra-chromosomal non-replicating vector and be transiently expressed or transiently active. In one embodiment, a homologous recombinant microorganism can be created wherein the IMI polynucleotide is integrated into a chromosome, a vector is prepared which contains at least a portion of an AHAS gene into which a deletion, addition, or substitution has been introduced to thereby alter, e.g., functionally disrupt, the endogenous AHAS gene and to create an IMI gene. To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene therapy American Scientist 87(3):240247). Other homologous recombination procedures in Triticum species are also well known in the art and are contemplated for use herein.

In the homologous recombination vector, the IMI gene can be flanked at its 5' and 3' ends by an additional nucleic acid molecule of the AHAS gene to allow for homologous recombination to occur between the exogenous IMI gene carried by the vector and an endogenous AHAS gene, in a microorganism or plant. The additional flanking AHAS nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in Physcomitrella patens). However, since the IMI gene normally differs from the AHAS gene at very few amino acids, a flanking sequence is not always necessary. The homologous recombination vector is introduced into a microorganism or plant cell (e.g., via polyethylene glycol mediated DNA), and cells in which the introduced IMI gene has homologously recombined with the endogenous AHAS gene are selected using art-known techniques.

In another embodiment, recombinant microorganisms can be produced that contain selected systems that allow for regulated expression of the introduced gene. For example, inclusion of an IMI gene on a vector placing it under control of the lac operon permits expression of the IMI gene only in the presence of IPTG. Such regulatory systems are well known in the art.

Whether present in an extra-chromosomal non-replicating vector or a vector that is integrated into a chromosome, the IMI polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell type-preferred, or tissue-preferred manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssu-RUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if time-specific gene expression is desired. Examples of such promoters are a salicylic acid inducible promoter (PCT Application No. WO 95/19443), a tetracycline inducible promoter (Getz et al., 1992, Plant J. 2:397-404), and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include; but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to, cellulose synthase (celA), Cim1, gamma-zein, globulin-1, maize 19 kD zein (cZ19131), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086, 169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptash-ne, 1985, Cell 43:729-736).

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an IMI polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) an IMI polynucleotide. Accordingly, the invention further provides methods for producing IMI polypeptides using the host cells of the invention. In one embodiment, the method comprises culturing the host cell of invention (into which a recombinant expression vector encoding an IMI polypeptide has been introduced, or into which genome has been introduced a gene encoding a wild-type or IMI polypeptide) in a suitable medium until IMI polypeptide is produced. In another embodiment, the method further comprises isolating IMI polypeptides from the medium or the host cell. Another aspect of the invention pertains to isolated IMI polypeptides, and biologically active portions thereof. An isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of IMI polypeptide in which the polypeptide is separated from some of the cellular components of the cells in which it is naturally or recombinantly produced. In one embodiment, the language "substantially free of cellular material" includes preparations of an IMI polypeptide having less than about 30% (by dry weight) of non-IMI material (also referred to herein as a "contaminating polypeptide"), more preferably less than about 20% of non-IMI material, still more preferably less than about 10% of non-IMI material, and most preferably less than about 5% non-IMI material.

When the IMI polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of IMI polypeptide in which the polypeptide is separated from chemical precursors or other chemicals that are involved in the synthesis of the polypeptide. In one embodiment, the language "substantially free of chemical precursors or other chemicals" includes preparations of an IMI polypeptide having less than about 30% (by dry weight) of chemical precursors or non-IMI chemicals, more preferably less than about 20% chemical precursors or non-IMI chemicals, still more preferably less than about 10% chemical precursors or non-IMI chemicals, and most preferably less than about 5% chemical precursors or non-IMI chemicals. In preferred embodiments, isolated polypeptides, or biologically active portions thereof, lack contaminating polypeptides from the same organism from which the IMI polypeptide is derived. Typically, such polypeptides are produced by recombinant expression of, for example, a *Triticum turgidum* IMI polypeptide in plants other than *Triticum turgidum*, or in microorganisms such as *C. glutamicum*, ciliates, algae, or fungi.

The IMI polynucleotide and polypeptide sequences of the invention have a variety of uses. The nucleic acid and amino acid sequences of the present invention can be used to transform plants, thereby modulating the plant's tolerance to imidazolinone herbicides. Accordingly, the invention provides a method of producing a transgenic plant having increased tolerance to an imidazolinone herbicide comprising, (a) transforming a plant cell with one or more expression vectors comprising one or more IMI nucleic acids, and (b) generating from the plant cell a transgenic plant with an increased tolerance to an imidazolinone herbicide as compared to a wild type variety of the plant. In one embodiment, the multiple IMI nucleic acids are derived from different genomes. Also included in the present invention are methods of producing a transgenic plant having increased tolerance to an imidazolinone herbicide comprising, (a) transforming a plant cell with an expression vector comprising an IMI nucleic acid, wherein the nucleic acid is a non-lmi 1 nucleic acid and (b) generating from the plant cell a transgenic plant with an increased tolerance to an imidazolinone herbicide as compared to a wild type variety of the plant.

The present invention includes methods of modifying a plant's tolerance to an imidazolinone herbicide comprising modifying the expression of one or more IMI nucleic acids. Preferably, the nucleic acids are located on or derived from different genomes. The plant's tolerance to the imidazolinone herbicide can be increased or decreased as achieved by increasing or decreasing the expression of an IMI polynucleotide, respectively. Preferably, the plant's tolerance to the imidazolinone herbicide is increased by increasing expression of an IMI polynucleotide. Expression of an IMI polynucleotide can be modified by any method known to those of skill in the art. The methods of increasing expression of IMI polynucleotides can be used wherein the plant is either transgenic or not transgenic. In cases when the plant is transgenic, the plant can be transformed with a vector containing any of the above described IMI coding nucleic acids, or the plant can be transformed with a promoter that directs expression of endogenous IMI polynucleotides in the plant, for example. The invention provides that such a promoter can be tissue specific or developmentally regulated. Alternatively, non-transgenic plants can have endogenous IMI polynucleotide expression modified by inducing a native promoter. The expression of polynucleotides comprising a polynucleotide sequence as defined in SEQ ID NO:1, SEQ ID NO:3, SEQ ID NO:5, or SEQ ID NO:23 in target plants can be accomplished by, but is not limited to, one of the following examples: (a) constitutive promoter, (b) chemical-induced promoter, and (c) engineered promoter over-expression with for example zinc-finger derived transcription factors (Greisman and Pabo, 1997, Science 275: 657).

In a preferred embodiment, transcription of the IMI polynucleotide is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as an IMI nucleic acid. Therefore, activating and repressing ZFPs can be created that specifically recognize the IMI polynucleotide promoters described above and used to increase or decrease IMI polynucleotide expression in a plant, thereby modulating the herbicide tolerance of the plant.

As described in more detail above, the plants produced by the methods of the present invention can be monocots or divots. The plants can be selected from maize, wheat, rye, oat, triticale, rice, barley, soybean, peanut, cotton, rapeseed, canola, *manihot*, pepper, sunflower, *tagetes*, solanaceous plants, potato, tobacco, eggplant, tomato, *Vicia* species, pea, alfalfa, coffee, cacao, tea, *Salix* species, oil palm, coconut, perennial grass, and forage crops, for example. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover. In a preferred embodiment, the plant is a wheat plant. In each of the methods described above, the plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations.

As described above, the present invention teaches compositions and methods for increasing the imidazolinone tolerance of a wheat plant or seed as compared to a wild-type variety of the plant or seed. In a preferred embodiment, the imidazolinone tolerance of a wheat plant or seed is increased such that the plant or seed can withstand an imidazolinone herbicide application of preferably approximately 10-400 g ai ha$^{-1}$, more preferably 20-160 g ai ha$^{-1}$, and most preferably 40-80 g ai ha$^{-1}$. As used herein, to "withstand" an imidazolinone herbicide application means that the plant is either not killed or not injured by such application.

Additionally provided herein is a method of controlling weeds within the vicinity of a wheat or triticale plant, comprising applying an imidazolinone herbicide to the weeds and to the wheat or triticale plant, wherein the wheat or triticale plant has increased tolerance to the imidazolinone herbicide as compared to a wild type variety of the wheat or triticale plant, and wherein the wheat or triticale plant comprises one or more IMI nucleic acids. In one embodiment, the wheat or triticale plant comprises multiple IMI nucleic acids located on or derived from different genomes, wherein the IMI nucleic acids are selected from the group consisting of an Imi 1 nucleic acid, an Imi 2 nucleic acid, and an Imi 3 nucleic acid. In another embodiment, the plant comprises an Imi 2 nucleic acid and an Imi 3 nucleic acid. By providing for wheat and triticale plants having increased tolerance to imidazolinone, a wide variety of formulations can be employed for protecting wheat and triticale plants from weeds, so as to enhance plant growth and reduce competition for nutrients. An imidazolinone herbicide can be used by itself for pre-emergence, post-emergence, pre-planting, and at-planting control of weeds in areas surrounding the wheat plants described herein, or an imidazolinone herbicide formulation can be used that contains other additives. The imidazolinone herbicide can also be used as a seed treatment. Additives found in an imidazolinone herbicide formulation include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates, and liquid concentrates. The imidazolinone herbicide and herbicide formulations can be applied in accordance with conventional methods, for example, by spraying, irrigation, dusting, or the like.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Mutagenesis and Selection of Tolerant *Durum* Wheat Lines

The imidazolinone tolerant wheat lines were derived through mutation and subsequent conventional selection techniques. Initial seed mutagenesis was by treating seed of the wheat variety *Durum* with either 3 or 3.5 ml EMS (ethylmethane sulfonate) per liter for 2 hrs, after a tap water presoak treatment of 5.5 hr, then rinsing with distilled water. During EMS treatment, the seeds were shaken every 10-15 minutes. After the 2 hr EMS treatment, that mutagen was poured off, and replaced with phosphate buffer (0.001 M, pH 3.5). Seeds were then treated with sodium azide (2 ml/liter of a 1 M stock solution), during which the seeds were shaken intermittently for 1 hr. The liquid was decanted, and the seeds were rinsed twice with distilled water, drained, and laid out on trays in a greenhouse for 24-36 hours to dry, before planting in the field in moist soil.

The M1 generation plants arising from the treated seeds were harvested in bulk, and the resulting M2 seeds were planted. M2 plants were treated with 10 oz/ac of Raptor herbicide (88.6 g imazamox/ha) at the three true leaf stage. Plants surviving the herbicide application were transplanted to a greenhouse for M3 seed production.

M2:3 lines were screened in a greenhouse using either 10 oz/acre (88.6 g imazamox/ha) or 12 oz/acre (106.3 g imazamox/ha) of Raptor® herbicide. Herbicide was applied at the three true leaf stage. M3:4 seed was produced from the most tolerant M3 plants.

Example 2

Tolerance of *Durum* Wheat Lines to Imidazolinione Herbicides

Field Trials (1):
Nine M4:6 lines derived from four M2 plants (C119, C132, C137, CO12) were evaluated in a replicated trial at one location in a *durum* growing area in Italy. 75 g/ha of imazamox was applied to BBCH growth stage 21-25 plants. A rate of 35 g/ha would typically result in virtually 100% mortality of susceptible wheat. Percent crop response (overall injury) varied from 0 to 13% 21 days after treatment (DAT), and from 0 to 17% 43 DAT. Yield as a percent of the same line untreated varied from 85% to 102%.

Field Trials (2):
One hundred ten M3:4 lines derived from sixteen M2 plants were screened at 71 g/ha and 160 g/ha imazamox. The number of M4 lines per M2 plant varied from one to twenty. Tolerance of M3:4 lines was compared to untreated plots of the same line as well as to treated plots of a wild-type cultivar from which some of them were derived. Table 1 summarizes the results.

All tested lines survived at both rates of herbicide treatment, whereas all plants of the wild type were killed at both rates. Based on comparison to the wild type line, all lines tested expressed considerable tolerance to the applied rates, particularly when looking at height reduction relative to untreated plots. A rate of 35 g/ha imazamox is adequate to kill susceptible *durum* wheat. Therefore, the lines evaluated were tolerant to a rate from almost 3 times to over 4 times that rate.

TABLE 1

Table 1. Tolerance scores of M3:4 lines derived from 14 different M2 plants treated at two different rates of imazamox

| | % Chlorosis | | | | | | % Height Reduction | | | | | |
|---|---|---|---|---|---|---|---|---|---|---|---|---|
| | 14 DAT[1] | | | 30 DAT | | | 14 DAT | | | 30 DAT | | |
| M2 Designation | 0 | 71[2] | 160[3] | 0 | 71 | 160 | 0 | 71 | 160 | 0 | 71 | 160 |
| Wild Type | 0 | 90 | 90 | 0 | 100 | 100 | 0 | 100 | 100 | 0 | 100 | 100 |
| UT01 | 0 | 0-10 | 1-10 | 0 | 0 | 0-5 | 0 | 0 | 0 | 0 | 0-10 | 0-20 |
| UT03 | 0 | 0 | 5 | 0 | 5 | 5 | 0 | 10 | 10 | 0 | 5 | 5 |
| UT05 | 0 | 5-10 | 5-15 | 0 | 5-10 | 5-20 | 0 | 5-10 | 10-30 | 0 | 5-10 | 5-20 |
| UT07 | 0 | 0-5 | 5-10 | 0 | 0-10 | 5-15 | 0 | 0-10 | 0-10 | 0 | 0-5 | 0-10 |
| UT08 | 0 | 0-10 | 0-10 | 0 | 0-10 | 0-15 | 0 | 0-10 | 0-10 | 0 | 0-10 | 520 |
| UT10 | 0 | 5-10 | 10 | 0 | 5 | 5 | 0 | 0-10 | 0-20 | 0 | 0-5 | 0-10 |
| UT12 | 0 | 0-10 | 10-15 | 0 | 0-5 | 5-10 | 0 | 0-10 | 10-20 | 0 | 0-10 | 5-10 |
| UT13 | 0 | 5 | 5 | 0 | 5 | 5-10 | 0 | 0-10 | 0-10 | 0 | 5 | 5 |
| UT14 | 0 | 5-10 | 10 | 0 | 0 | 0 | 0 | 0 | 0-10 | 0 | 0-10 | 0-10 |
| UT15 | 0 | 30-70 | 30-70 | 0-5 | 0-10 | 0-15 | 0 | 0-10 | 0-10 | 0 | 5-20 | 5-30 |
| UT16 | 0 | 5-10 | 10-20 | 0 | 0 | 0-5 | 0 | 0 | 0-10 | 0 | 0-10 | 0-10 |
| UT17 | 0 | 5-20 | 5-30 | 0 | 0 | 0-5 | 0 | 0-20 | 0-30 | 0 | 5-20 | 5-30 |
| UT19 | 0 | 30-40 | 40 | 0 | 0 | 0-5 | 0 | 0-10 | 0-10 | 0 | 5-20 | 10-20 |
| UT20 | 0 | 0-5 | 5-10 | 0 | 0 | 0 | 0 | 0 | 0-20 | 0 | 5-10 | 10-15 |

[1]DAT refers to days after treatment with applicable rate of herbicide that rating was made
[2,3]Numbers are rates of herbicide application in g/ha
Numbers in the body of the table represent the range of reaction across M3:4 lines derived from each listed M2 plant.

Greenhouse Trial:

Fifteen *Durum* lines, each derived from a different M2 plant, and two wild type *durum* lines were evaluated for tolerance to the imidazolinone herbicide imazamox at rates of 100 and 160 g/ha in a greenhouse trial. Evaluations of tolerance were made at 14 and 21 days after treatment. Injury was scored on a 0-9 scale, with 0 representing no injury and 9 plant death. Table 2 summarizes the results.

All lines exhibited greater tolerance than the wild type lines in that all wild type plants were killed by 21 days after treatment, a time at which even the lines with significant injury at 14 days had begun to recover. A rate of 35 g/ha imazamox is adequate to kill susceptible *Durum* wheat. Therefore, all fifteen lines derived from mutagenesis exhibited excellent tolerance to imazamox.

TABLE 2

Average plant injury ratings of progeny derived from fifteen durum M2 plants and one wild type durum line treated at two different rates of imazamox.

| Line | 14 DAT[1] | | 21 DAT | |
|---|---|---|---|---|
| | 100 g/ha | 160 g/ha | 100 g/ha | 160 g/ha |
| UT01 | 4.0 | 4.1 | 1.4 | 2.6 |
| UT03 | 4.8 | 5.2 | 2.2 | 2.8 |
| UT05 | 3.0 | 3.3 | 1.3 | 1.8 |
| UT07 | 3.7 | 4.4 | 1.9 | 2.5 |
| UT08 | 4.5 | 5.5 | 1.9 | 3.0 |
| UT10 | 5.8 | 6.5 | 4.3 | 5.1 |
| UT12 | 4.8 | 5.7 | 2.1 | 2.8 |
| UT13 | 4.7 | 5.8 | 2.3 | 3.4 |
| UT14 | 3.1 | 4.8 | 1.7 | 3.5 |
| UT15 | 4.3 | 4.6 | 2.7 | 3.0 |
| UT16 | 5.4 | 4.9 | 2.0 | 2.8 |
| UT17 | 4.1 | 4.7 | 2.5 | 3.1 |
| UT19 | 3.3 | 3.6 | 1.1 | 1.7 |
| UT20 | 5.0 | 5.3 | 2.1 | 2.5 |
| C119 Wild Type Line | 4.8 | 4.9 | 1.0 | 1.4 |
| UT | 8.9 | 9.0 | 9.0 | 9.0 |

[1]DAT refers to days after treatment with applicable rate of herbicide that rating was made
Numbers in the body of the table represent the average of 24 plants per treatment. Plants were scored on a 0-9 scale, with 0 = no injury, and 9 = plant death Example 3

Biochemical Basis of Tolerance

The enzyme targeted by imidazolinone herbicides is acetohydroxyacid synthase (AHAS) the first catalytic enzyme in the biochemical synthesis of the branched chain amino acids valine, leucine, and isoleucine. The herbicide is thought to bind to sites within a pocket in the enzyme, but does not bind to the active site.

The in vitro activity of AHAS enzyme extracted from the plant can be measured biochemically. The effect on activity of adding different concentrations of an imidazolinone herbicide such as imazamox to AHAS protein extracted from wild type Durum wheat plants (Line UT) can be seen in Table 3. Even at relatively low concentrations, AHAS activity falls off rapidly.

Table 3 also contains AHAS activity data for several M2-derived imidazolinone herbicide tolerant lines. Inhibition of activity is markedly less at lower concentrations of imazamox, and even at the highest concentration, activity is generally one third to one half that of the control. These data combined with greenhouse and field tolerance data would appear to support a mutagenesis-derived change in at least one AHAS gene in the Durum genome that results in AHAS protein being produced with decreased inhibition by imazamox.

TABLE 3

In vitro AHAS activity, expressed as percent of control, of thirteen durum lines and a wild type control (UT), in the presence of various concentrations of imazamox

| Line | uM Imazamox | | | | |
|---|---|---|---|---|---|
| | 0 | 13 | 25 | 50 | 100 |
| C119 | 100.0 | 54.0 | 56.3 | 55.3 | 41.9 |
| UT01 | 100.0 | 61.6 | 58.5 | 54.1 | 49.6 |
| UT03 | 100.0 | 73.7 | 63.5 | 60.3 | 52.2 |
| UT05 | 100.0 | 54.1 | 59.5 | 56.9 | 45.4 |
| UT07 | 100.0 | 64.3 | 61.3 | 46.9 | 50.6 |
| UT08 | 100.0 | 60.3 | 55.3 | 49.6 | 41.2 |
| UT10 | 100.0 | 68.4 | 59.7 | 54.9 | 46.6 |
| UT12 | 100.0 | 58.3 | 55.6 | 52.7 | 44.9 |
| UT13 | 100.0 | 73.2 | 60.4 | 51.8 | 46.5 |
| UT14 | 100.0 | 62.4 | 53.5 | 56.8 | 55.6 |
| UT16 | 100.0 | 51.9 | 46.7 | 45.5 | 41.7 |
| UT17 | 100.0 | 59.3 | 48.0 | 48.0 | 36.5 |
| UT20 | 100.0 | 63.4 | 61.8 | 50.3 | 40.3 |
| UT | 100.0 | 15.9 | 11.1 | 10.2 | 5.4 |

Example 4

Molecular Basis of Tolerance

Molecular characterization of the imidazolinone tolerant lines confirmed the presence of specific mutations in the genes encoding the AHAS enzyme (Als 2 and Als 3). The imidazolinone tolerant C119 line contained a guanine to adenine base pair substitution in the Als 2 gene that resulted in a serine to asparagine substitution in Domain E of the AHAS enzyme. The C119 line did not contain any mutations in the Als 3 gene. Similarly, imidazolinone tolerant lines UT01, UT03, UT05, UT07, UT08, UT10, UT13, UT14, UT16, UT17, UT20, all contained a wild type sequence Als 3 gene and the guanine to adenine base pair substitution in the Als 2 gene.

The imidazolinone tolerant UT12 line contained a guanine to adenine base pair substitution in the Als 3 gene that resulted in a serine to asparagine substitution in Domain E of the AHAS enzyme. The UT12 line did not contain any mutations in the Als 2 gene.

The imidazolinone tolerant Utopia lines UT15 and UT19 contained a novel mutation in the Als 3 gene, a guanine to adenine base pair substitution that resulted in an alanine to threonine amino acid substitution in the amino terminal portion of the AHAS enzyme. The imidazolinone tolerant Utopia line UT15 also contained a thymine to cytosine base pair substitution in the Als 2 gene that did not result in an amino acid substitution.

Example 5

Engineering Imidazolinone Tolerant Wheat Plants

Imidazolinone tolerant wheat plants are produced by a method as described by Ishida et al. (1996, Nature Biotech. 14:745-750). Immature embryos sized 1-2 mm are isolated 10-15 days after pollination and sterilized with Ethanol and 30% Chlorox solution. Immature embryos are infected with Agrobacterium cells harboring the construct of interest in a Japan Tobacco vector on LS-infection medium and then co-cultivated on LS-co-cultivation medium for 3 to 7 days (All medium is derived from Japan Tobacco according to Ishida et al. (1996, Nature Biotech. 14:745-750)). Explants are then transferred to LS medium containing 0.05 to 0.1 µM PURSUIT® and are cultured under dim light for 1 to 2 weeks. Actively growing calli are transferred for 2nd and 3rd selection on LS medium supplemented with 0.5 to 1.0 µM imazethapyr (PURSUIT®) and cultured for 2 to 3 weeks. After 3rd selection, calli are transferred to regeneration medium supplemented with 0.25 to 0.75 µM imazethapyr (PURSUIT®) for three weeks. Shoots are then transferred to ½ LS rooting medium and cultured for three weeks before transplanted to soil and grown in the greenhouse. Putative transgenic plants are sprayed with 25 to 50 g/ha imazamox (RAPTOR®) to eliminate escapes.

We claim:

1. A wheat plant, wherein the wheat plant was obtained by a process comprising:
   crossing a plant of line UT15 or UT19, a representative sample of seed of each line having been deposited with the ATCC under Patent Deposit No. PTA-4919 and ATCC PTA-4922, respectively, with another wheat variety,
   wherein the plant comprises the UT15 or UT19 Imi3 nucleic acid, said UT15 or UT19 Imi3 nucleic acid comprising a polynucleotide sequence encoding an IMI polypeptide having an alanine to threonine substitution in Domain C, said polynucleotide sequence being of the A genome, and
   said plant having increased tolerance to an imidazolinone herbicide as compared to that of a wild type wheat plant.

2. The plant of claim 1, wherein the Imi3 nucleic acid is selected from the group consisting of:
   a. polynucleotides comprising a nucleic acid sequence as defined in SEQ ID NO:5; and
   b. polynucleotides encoding a polypeptide comprising an amino acid sequence as defined in SEQ ID NO:6.

3. The plant of claim 1, wherein the plant comprises at least one additional *Triticum turgidum* IMI nucleic acid.

4. The plant of claim 1, wherein the imidazolinone herbicide comprises at least one of: imazethapyr, imazapic, imazamox, imazaquin, imazethabenz, imazapyr, a mixture of imazapyr and imazamox, or a combination thereof.

5. The plant of claim 4, wherein the imidazolinone herbicide comprises imazethapyr.

6. The plant of claim 4, wherein the imidazolinone herbicide comprises imazamox.

7. A part of the wheat plant of claim 1.

8. A wheat seed of the wheat plant of claim 1.

9. The seed of claim 8 further comprising a seed treatment.

10. The seed of claim 9, wherein said seed treatment comprises an herbicidal composition.

11. The seed of claim 10, wherein said herbicidal composition comprises an imidazolinone herbicide.

12. The seed of claim 11, wherein said imidazolinone herbicide comprises at least one of: imazethapyr, imazapic, imazamox, imazaquin, imazethabenz, imazapyr, a mixture of imazapyr and imazamox, or a combination thereof.

13. The seed of claim 12, wherein the imidazolinone herbicide comprises imazethapyr.

14. The seed of claim 12, wherein the imidazolinone herbicide comprises imazamox.

15. A method for treating a seed comprising:
   a. providing the seed of claim 8; and
   b. treating the seed with an herbicidal composition comprising an imidazolinone.

16. A method for identifying the presence of an Imi3 nucleic acid in a plant, plant part, cell, or seed thereof, comprising:
  a) providing a plant, plant part, cell, or seed of the plant of claim 1;
  b) extracting nucleic acid material from said plant, plant part, cell, or seed;
  c) assaying the extracted nucleic acid material for the presence of the Imi3 nucleic acid, wherein said Imi3 nucleic acid comprises:
    (i) a nucleic acid comprising the polynucleotide sequence of SEQ ID NO:5; or
    (ii) a nucleic acid encoding an IMI polypeptide comprising the amino acid sequence of SEQ ID NO:6.

\* \* \* \* \*

SEQUENCE LISTING

```
<160> NUMBER OF SEQ ID NOS: 29

<210> SEQ ID NO 1
<211> LENGTH: 1788
<212> TYPE: DNA
<213> ORGANISM: Triticum durum

<400> SEQUENCE: 1
tcccccgccg ccacctccgc cgcgcctccc gccaccgcgc tccggccgtg gggcccctcc      60
gagccccgta agggcgccga catcctcgtc gaggcgctgg agcgctgcgg catcgtcgac     120
gtcttcgcct accctggcgg cgcgtccatg gagatccacc aggcgctgac gcgctcgcca     180
```

-continued

```
gtcatcacca accacctctt ccgccacgag caggggagg cgttcgcggc gtccgggtac    240
gcccgcgcgt ccggccgcgt cggcgtctgc gtcgccacct ccggcccggg ggccaccaac    300
ctcgtctccg cgctcgccga cgctctcctc gactccatcc ccatggtcgc catcacgggc    360
caggtccccc gccgcatgat cggcacggat gcgttccagg agacgcccat cgtggaggtc    420
acgcgctcca tcaccaagca caactacctg gtccttgacg tggaggatat ccccgcgtc     480
atccaggaag ccttcttcct cgcatcctct ggccgcccgg ggccggtgct ggttgatatc    540
cccaaggaca tccagcagca gatggctgtg cctgtctggg acacgccgat gagtttgcca    600
gggtacatcg cccgcctgcc caagccacca tctactgaat cgcttgagca ggtcctgcgt    660
ctggttggcg agtcacggcg cccaattctg tatgttggtg gtggctgcgc tgcatctggt    720
gaggagttgc gccgctttgt tgagctcact gggattccag ttacaactac tcttatgggc    780
cttggcaact tccccagtga cgaccactg tctctgcgca tgctggggat gcatggcact    840
gtgtatgcaa attatgcagt agataaggct gacctgttgc ttgcatttgg tgtgcggttt    900
gatgatcgtg tgaccgggaa aatcgaggct tttgcaagca ggtccaagat tgtgcacatt    960
gacattgacc cagctgagat tggcaagaac aagcagccac atgtctccat ttgtgcagat   1020
gttaagcttg ctttacaggg gttgaatgct ctattaaatg ggagcaaagc acaacagggt   1080
ctggattttg gtccatggca aaggagttg gatcagcaga gagggagtt cctctagga    1140
ttcaagactt ttggtgaggc catcccgccg caatatgcta tccaggtact ggatgagctg   1200
acaaaagggg aggcgatcat tgccaccggt gttgggcagc atcagatgtg ggcggctcag   1260
tattacactt acaagcggcc acggcagtgg ctgtcttcgt ccggtttggg tgcaatggga   1320
tttgggttgc cagctgcagc tggcgctgct gtggccaacc caggtgttac agttgttgac   1380
attgatgggg atggtagttt cctcatgaac attcaggagt tggcgttgat ccgtattgag   1440
aacctcccag tgaaggtgat gatattgaac aaccagcatc tgggaatggt ggtgcagtgg   1500
gaggataggt tttacaaggc caaccgggcg cacacatacc ttggcaaccc agaaaatgag   1560
ggtgagatat atccagattt tgtgacgatt gctaaaggat tcaacgttcc ggcagttcgt   1620
gtgacgaaga agagcgaagt cactgcagca atcaagaaga tgcttgagac cccagggcca   1680
tacttgttgg atatcattgt cccgcatcag gagcacgtgc tgcctatgat cccaaacggt   1740
ggtgctttta aggacatgat catggagggt gatggcagga cctcgtac               1788
```

<210> SEQ ID NO 2
<211> LENGTH: 596
<212> TYPE: PRT
<213> ORGANISM: Triticum durum

<400> SEQUENCE: 2

```
Ser Pro Ala Ala Thr Ser Ala Ala Pro Pro Ala Thr Ala Leu Arg Pro
1               5                   10                  15

Trp Gly Pro Ser Glu Pro Arg Lys Gly Ala Asp Ile Leu Val Glu Ala
            20                  25                  30

Leu Glu Arg Cys Gly Ile Val Asp Val Phe Ala Tyr Pro Gly Gly Ala
        35                  40                  45

Ser Met Glu Ile His Gln Ala Leu Thr Arg Ser Pro Val Ile Thr Asn
    50                  55                  60

His Leu Phe Arg His Glu Gln Gly Glu Ala Phe Ala Ala Ser Gly Tyr
65                  70                  75                  80

Ala Arg Ala Ser Gly Arg Val Gly Val Cys Val Ala Thr Ser Gly Pro
                85                  90                  95
```

```
Gly Ala Thr Asn Leu Val Ser Ala Leu Ala Asp Ala Leu Leu Asp Ser
            100                 105                 110

Ile Pro Met Val Ala Ile Thr Gly Gln Val Pro Arg Met Ile Gly
            115                 120                 125

Thr Asp Ala Phe Gln Glu Thr Pro Ile Val Glu Val Thr Arg Ser Ile
130                 135                 140

Thr Lys His Asn Tyr Leu Val Leu Asp Val Glu Asp Ile Pro Arg Val
145                 150                 155                 160

Ile Gln Glu Ala Phe Phe Leu Ala Ser Ser Gly Arg Pro Gly Pro Val
                    165                 170                 175

Leu Val Asp Ile Pro Lys Asp Ile Gln Gln Met Ala Val Pro Val
            180                 185                 190

Trp Asp Thr Pro Met Ser Leu Pro Gly Tyr Ile Ala Arg Leu Pro Lys
            195                 200                 205

Pro Pro Ser Thr Glu Ser Leu Glu Gln Val Leu Arg Leu Val Gly Glu
            210                 215                 220

Ser Arg Arg Pro Ile Leu Tyr Val Gly Gly Cys Ala Ala Ser Gly
225                 230                 235                 240

Glu Glu Leu Arg Arg Phe Val Glu Leu Thr Gly Ile Pro Val Thr Thr
                    245                 250                 255

Thr Leu Met Gly Leu Gly Asn Phe Pro Ser Asp Asp Pro Leu Ser Leu
            260                 265                 270

Arg Met Leu Gly Met His Gly Thr Val Tyr Ala Asn Tyr Ala Val Asp
            275                 280                 285

Lys Ala Asp Leu Leu Leu Ala Phe Gly Val Arg Phe Asp Asp Arg Val
            290                 295                 300

Thr Gly Lys Ile Glu Ala Phe Ala Ser Arg Ser Lys Ile Val His Ile
305                 310                 315                 320

Asp Ile Asp Pro Ala Glu Ile Gly Lys Asn Lys Gln Pro His Val Ser
                    325                 330                 335

Ile Cys Ala Asp Val Lys Leu Ala Leu Gln Gly Leu Asn Ala Leu Leu
            340                 345                 350

Asn Gly Ser Lys Ala Gln Gln Gly Leu Asp Phe Gly Pro Trp His Lys
            355                 360                 365

Glu Leu Asp Gln Gln Lys Arg Glu Phe Pro Leu Gly Phe Lys Thr Phe
            370                 375                 380

Gly Glu Ala Ile Pro Pro Gln Tyr Ala Ile Gln Val Leu Asp Glu Leu
385                 390                 395                 400

Thr Lys Gly Glu Ala Ile Ile Ala Thr Gly Val Gly Gln His Gln Met
                    405                 410                 415

Trp Ala Ala Gln Tyr Tyr Thr Tyr Lys Arg Pro Arg Gln Trp Leu Ser
            420                 425                 430

Ser Ser Gly Leu Gly Ala Met Gly Phe Gly Leu Pro Ala Ala Gly
            435                 440                 445

Ala Ala Val Ala Asn Pro Gly Val Thr Val Val Asp Ile Asp Gly Asp
            450                 455                 460

Gly Ser Phe Leu Met Asn Ile Gln Glu Leu Ala Leu Ile Arg Ile Glu
465                 470                 475                 480

Asn Leu Pro Val Lys Val Met Ile Leu Asn Asn Gln His Leu Gly Met
                    485                 490                 495

Val Val Gln Trp Glu Asp Arg Phe Tyr Lys Ala Asn Arg Ala His Thr
            500                 505                 510
```

Tyr Leu Gly Asn Pro Glu Asn Glu Gly Glu Ile Tyr Pro Asp Phe Val
            515                 520                 525

Thr Ile Ala Lys Gly Phe Asn Val Pro Ala Val Arg Val Thr Lys Lys
        530                 535                 540

Ser Glu Val Thr Ala Ala Ile Lys Lys Met Leu Glu Thr Pro Gly Pro
545                 550                 555                 560

Tyr Leu Leu Asp Ile Ile Val Pro His Gln Glu His Val Leu Pro Met
                565                 570                 575

Ile Pro Asn Gly Gly Ala Phe Lys Asp Met Ile Met Glu Gly Asp Gly
            580                 585                 590

Arg Thr Ser Tyr
        595

<210> SEQ ID NO 3
<211> LENGTH: 575
<212> TYPE: DNA
<213> ORGANISM: Triticum durum

<400> SEQUENCE: 3
gcggctcagt attacactta caagcggcca cggcagtggc tgtcttcgtc tggtttgggg      60
gcaatgggat ttgggttacc agctgcagct ggcgctgctg tggccaaccc aggtgttaca     120
gttgttgaca ttgatggaga tggtagtttc ctcatgaaca ttcaggagtt ggcattgatc     180
cgtattgaga acctccctgt gaaggtgatg atattgaaca accagcatct gggaatggtg     240
gtgcaatggg aggataggtt ttacaaggcc aatcgggcgc acacatacct tggcaaccca     300
gaaaatgaga gtgagatata tccagatttt gtgacgattg ctaaaggatt caacgttccg     360
gcagttcgtg tgacgaagaa gagcgaagtc actgcagcaa tcaagaagat gcttgagacc     420
ccagggccat acttgttgga tatcatcgtc ccgcatcagg agcacgtgct gcctatgatc     480
ccaaacggtg gtgctttcaa ggacatgatc atggagggtg atggcaggac ctcgtactga     540
aatttcgacc tacaagacct acaagtgtga catgc                                575

<210> SEQ ID NO 4
<211> LENGTH: 179
<212> TYPE: PRT
<213> ORGANISM: Triticum durum

<400> SEQUENCE: 4

Ala Ala Gln Tyr Tyr Thr Tyr Lys Arg Pro Arg Gln Trp Leu Ser Ser
1               5                   10                  15

Ser Gly Leu Gly Ala Met Gly Phe Gly Leu Pro Ala Ala Gly Ala
            20                  25                  30

Ala Val Ala Asn Pro Gly Val Thr Val Val Asp Ile Asp Gly Asp Gly
            35                  40                  45

Ser Phe Leu Met Asn Ile Gln Glu Leu Ala Leu Ile Arg Ile Glu Asn
    50                  55                  60

Leu Pro Val Lys Val Met Ile Leu Asn Asn Gln His Leu Gly Met Val
65                  70                  75                  80

Val Gln Trp Glu Asp Arg Phe Tyr Lys Ala Asn Arg Ala His Thr Tyr
                85                  90                  95

Leu Gly Asn Pro Glu Asn Glu Ser Glu Ile Tyr Pro Asp Phe Val Thr
            100                 105                 110

Ile Ala Lys Gly Phe Asn Val Pro Ala Val Arg Val Thr Lys Lys Ser
            115                 120                 125

Glu Val Thr Ala Ala Ile Lys Lys Met Leu Glu Thr Pro Gly Pro Tyr

```
              130                 135                140
Leu Leu Asp Ile Ile Val Pro His Gln Glu His Val Leu Pro Met Ile
145                 150                155                160

Pro Asn Gly Gly Ala Phe Lys Asp Met Ile Met Glu Gly Asp Gly Arg
                165                170                175

Thr Ser Tyr
```

<210> SEQ ID NO 5
<211> LENGTH: 1723
<212> TYPE: DNA
<213> ORGANISM: Triticum durum

<400> SEQUENCE: 5

```
ccgcaagggc gccgacatcc tcgtcgaggc gctcgagcgc tgcggcatcg tcgacgtatt     60
cgcctacccc ggcggcacgt ccatggagat ccaccaggcg ctgacgcgct cgcccgtcat    120
caccaaccac ctcttccgcc acgagcaggg ggaggcgttc gcggcgtccg gctacgcccg    180
cgcgtccggc gcgtcggcg  tctgcgtcgc cacctccggc ccgggggcca ccaacctcgt    240
ctccgcgctc gctgacgccc tcctcgactc catccccatg gtcgccatca cgggccaggt    300
ccccccgccgc atgatcggca cggacgcgtt ccaggagacg cccatagtgg aggtcacgcg    360
ctccatcacc aagcacaact acctggtcct tgacgtggag atatccccc  gcgtcatcca    420
ggaagccttc ttcctcgcgt cctctggccg ccgggggccg tgctggttg  atatccccaa    480
ggatatccag cagcagatgg ccgtgcctat ctgggacacg ccgatgagtt tgccagggta    540
catcgcccgc ctgcccaagc caccatctac tgaatcgctt gagcaggtcc tgcgtctggt    600
tggcgagtca cggcgcccaa ttctgtatgt tggtggtggc tgcgctgcat ccggcgagga    660
gttgcgccgc tttgttgagc tcactgggat tccggttaca actactctga tgggccttgg    720
caacttcccc agcgacgacc cactgtctct gcgcatgctt gggatgcatg gcactgtgta    780
tgcaaattat gcagtcgata aggctgacct gttgcttgca tttggtgtgc ggtttgatga    840
tcgcgtgact gggaaaatcg aggcctttgc aagcaggtcc aagattgtgc acattgacat    900
tgacccagct gagattggca agaacaagca gccacatgtc tccatttgtg cagatgttaa    960
gcttgcttta caggggttga atgctctatt aaatgggagc aaagcacaac agggtctgga   1020
ttttggtcca tggcacaagg agttggatca gcagaagagg gagtttcctc taggattcaa   1080
gacttttggc gaggccatcc cgccgcaata tgctatccag gtactggatg agctgacaaa   1140
aggggaggcg atcattgcta ctggtgttgg gcagcaccag atgtgggcgg ctcagtatta   1200
cacttacaag cggccacggc agtggctgtc ttcgtctggt ttgggggcaa tgggatttgg   1260
gttaccagct gcagctggcg ctgctgtggc aacccaggt gttacagttg ttgacattga   1320
tggagatggt agtttcctca tgaacattca ggagttggca ttgatccgta ttgagaacct   1380
ccctgtgaag gtgatgatat tgaacaacca gcatctggga atggtggtgc aatgggagga   1440
taggttttac aaggccaatc gggcgcacac ataccttggc aacccagaaa atgagagtga   1500
gatatatcca gattttgtga cgattgctaa aggattcaac gttccggcag ttcgtgtgac   1560
gaagaagagc gaagtcactg cagcaatcaa gaagatgctt gagacccag gccatactt   1620
gttggatatc atcgtcccgc atcaggagca cgtgctgcct atgatcccaa gcggtggtgc   1680
tttcaaggac atgatcatgg agggtgatgg caggacctcg tac                    1723
```

<210> SEQ ID NO 6
<211> LENGTH: 574

<212> TYPE: PRT
<213> ORGANISM: Triticum durum

<400> SEQUENCE: 6

```
Arg Lys Gly Ala Asp Ile Leu Val Glu Ala Leu Glu Arg Cys Gly Ile
1               5                   10                  15

Val Asp Val Phe Ala Tyr Pro Gly Gly Thr Ser Met Glu Ile His Gln
            20                  25                  30

Ala Leu Thr Arg Ser Pro Val Ile Thr Asn His Leu Phe Arg His Glu
        35                  40                  45

Gln Gly Glu Ala Phe Ala Ala Ser Gly Tyr Ala Arg Ala Ser Gly Arg
    50                  55                  60

Val Gly Val Cys Val Ala Thr Ser Gly Pro Gly Ala Thr Asn Leu Val
65                  70                  75                  80

Ser Ala Leu Ala Asp Ala Leu Leu Asp Ser Ile Pro Met Val Ala Ile
                85                  90                  95

Thr Gly Gln Val Pro Arg Arg Met Ile Gly Thr Asp Ala Phe Gln Glu
            100                 105                 110

Thr Pro Ile Val Glu Val Thr Arg Ser Ile Thr Lys His Asn Tyr Leu
        115                 120                 125

Val Leu Asp Val Glu Asp Ile Pro Arg Val Ile Gln Glu Ala Phe Phe
    130                 135                 140

Leu Ala Ser Ser Gly Arg Pro Gly Pro Val Leu Val Asp Ile Pro Lys
145                 150                 155                 160

Asp Ile Gln Gln Gln Met Ala Val Pro Ile Trp Asp Thr Pro Met Ser
                165                 170                 175

Leu Pro Gly Tyr Ile Ala Arg Leu Pro Lys Pro Pro Ser Thr Glu Ser
            180                 185                 190

Leu Glu Gln Val Leu Arg Leu Val Gly Glu Ser Arg Arg Pro Ile Leu
        195                 200                 205

Tyr Val Gly Gly Gly Cys Ala Ala Ser Gly Glu Glu Leu Arg Arg Phe
    210                 215                 220

Val Glu Leu Thr Gly Ile Pro Val Thr Thr Thr Leu Met Gly Leu Gly
225                 230                 235                 240

Asn Phe Pro Ser Asp Asp Pro Leu Ser Leu Arg Met Leu Gly Met His
                245                 250                 255

Gly Thr Val Tyr Ala Asn Tyr Ala Val Asp Lys Ala Asp Leu Leu Leu
            260                 265                 270

Ala Phe Gly Val Arg Phe Asp Asp Arg Val Thr Gly Lys Ile Glu Ala
        275                 280                 285

Phe Ala Ser Arg Ser Lys Ile Val His Ile Asp Ile Asp Pro Ala Glu
    290                 295                 300

Ile Gly Lys Asn Lys Gln Pro His Val Ser Ile Cys Ala Asp Val Lys
305                 310                 315                 320

Leu Ala Leu Gln Gly Leu Asn Ala Leu Asn Gly Ser Lys Ala Gln
                325                 330                 335

Gln Gly Leu Asp Phe Gly Pro Trp His Lys Glu Leu Asp Gln Gln Lys
            340                 345                 350

Arg Glu Phe Pro Leu Gly Phe Lys Thr Phe Gly Glu Ala Ile Pro Pro
        355                 360                 365

Gln Tyr Ala Ile Gln Val Leu Asp Glu Leu Thr Lys Gly Glu Ala Ile
    370                 375                 380

Ile Ala Thr Gly Val Gly Gln His Gln Met Trp Ala Ala Gln Tyr Tyr
385                 390                 395                 400
```

```
Thr Tyr Lys Arg Pro Arg Gln Trp Leu Ser Ser Gly Leu Gly Ala
                405                 410                 415
Met Gly Phe Gly Leu Pro Ala Ala Ala Gly Ala Ala Val Ala Asn Pro
            420                 425                 430
Gly Val Thr Val Val Asp Ile Asp Gly Asp Gly Ser Phe Leu Met Asn
                435                 440                 445
Ile Gln Glu Leu Ala Leu Ile Arg Ile Glu Asn Leu Pro Val Lys Val
            450                 455                 460
Met Ile Leu Asn Asn Gln His Leu Gly Met Val Val Gln Trp Glu Asp
465                 470                 475                 480
Arg Phe Tyr Lys Ala Asn Arg Ala His Thr Tyr Leu Gly Asn Pro Glu
                485                 490                 495
Asn Glu Ser Glu Ile Tyr Pro Asp Phe Val Thr Ile Ala Lys Gly Phe
                500                 505                 510
Asn Val Pro Ala Val Arg Val Thr Lys Lys Ser Glu Val Thr Ala Ala
            515                 520                 525
Ile Lys Lys Met Leu Glu Thr Pro Gly Pro Tyr Leu Leu Asp Ile Ile
            530                 535                 540
Val Pro His Gln Glu His Val Leu Pro Met Ile Pro Ser Gly Gly Ala
545                 550                 555                 560
Phe Lys Asp Met Ile Met Glu Gly Asp Gly Arg Thr Ser Tyr
                565                 570

<210> SEQ ID NO 7
<211> LENGTH: 1768
<212> TYPE: DNA
<213> ORGANISM: Triticum durum

<400> SEQUENCE: 7
cgcgcctccc gccaccgcgc tccggccgtg gggcccctcc gagccccgca agggcgccga      60
catcctcgtc gaggcgctgg agcgctgcgg catcgtcgac gtcttcgcct acctggcgg     120
cgcgtccatg gagatccacc aggcgctgac gcgctcgcca gtcatcacca accacctctt     180
ccgccacgag caggggagg cgttcgcggc gtccgggtac gcccgcgcgt ccggccgcgt     240
cggcgtctgc gtcgccacct ccggcccggg ggccaccaac ctcgtctccg cgctcgccga     300
cgctctcctc gactccatcc ccatggtcgc catcacgggc caggtccccc gccgcatgat     360
cggcacggat gcgttccagg agacgcccat cgtggaggtc acgcgctcca tcaccaagca     420
caactacctg gtccttgacg tggaggatat ccccgcgtc atccaggaag ccttcttcct     480
cgcatcctct ggccgccgg ggccggtgct ggttgatatc cccaaggaca tccagcagca     540
gatggctgtg cctgtctggg acacgccgat gagtttgcca gggtacatcg cccgcctgcc     600
caagccacca tctactgaat cgcttgagca ggtcctgcgt ctggttggcg agtcacggcg     660
cccaattctg tatgttggtg gtggctgcgc tgcatctggt gaggagttgc gccgctttgt     720
tgagctcact gggattccag ttacaactac tcttatgggc cttggcaact cccccagtga     780
cgacccactg tctctgcgca tgctggggat gcatggcact gtgtatgcaa attatgcagt     840
agataaggct gacctgttgc ttgcatttgg tgtgcggttt gatgatcgtg tgaccgggaa     900
aatcgaggct tttgcaagca ggtccaagat tgtgcacatt gacattgacc cagctgagat     960
tggcaagaac aagcagccac atgtctccat tgtgcagat gttaagcttg ctttacaggg    1020
gttgaatgct ctattaaatg ggagcaaagc acaacagggt ctggattttg tccatggca    1080
caaggagttg gatcagcaga agaggagttt cctctagga ttcaagactt ttggtgaggc    1140
```

-continued

```
catcccgccg caatatgcta tccaggtact ggatgagctg acaaaagggg aggcgatcat    1200
tgccaccggt gttgggcagc atcagatgtg ggcggctcag tattacactt acaagcggcc    1260
acggcagtgg ctgtcttcgt ccggtttggg tgcaatggga tttgggttgc agctgcagc     1320 tggcgctgct gtggccaacc caggtgttac agttgttgac attgatgggg atggtagttt    1380
cctcatgaac attcaggagt tggcgttgat ccgtattgag aacctcccag tgaaggtgat    1440
gatattgaac aaccagcatc tgggaatggt ggtgcagtgg gaggataggt tttacaaggc    1500
caaccgggcg cacacatacc ttggcaaccc agaaaatgag ggtgagatat atccagattt    1560
tgtgacgatt gctaaaggat tcaacgttcc ggcagttcgt gtgacgaaga agagcgaagt    1620
cactgcagca atcaagaaga tgcttgagac cccagggcca tacttgttgg atatcattgt    1680
cccgcatcag gagcacgtgc tgcctatgat cccaagcggt ggtgctttta aggacatgat    1740
catggagggt gatggcagga cctcgtac                                       1768
```

<210> SEQ ID NO 8
<211> LENGTH: 589
<212> TYPE: PRT
<213> ORGANISM: Triticum durum

<400> SEQUENCE: 8

```
Ala Pro Pro Ala Thr Ala Leu Arg Pro Trp Gly Pro Ser Glu Pro Arg
1               5                   10                  15

Lys Gly Ala Asp Ile Leu Val Glu Ala Leu Glu Arg Cys Gly Ile Val
            20                  25                  30

Asp Val Phe Ala Tyr Pro Gly Gly Ala Ser Met Glu Ile His Gln Ala
        35                  40                  45

Leu Thr Arg Ser Pro Val Ile Thr Asn His Leu Phe Arg His Glu Gln
    50                  55                  60

Gly Glu Ala Phe Ala Ala Ser Gly Tyr Ala Arg Ala Ser Gly Arg Val
65                  70                  75                  80

Gly Val Cys Val Ala Thr Ser Gly Pro Gly Ala Thr Asn Leu Val Ser
                85                  90                  95

Ala Leu Ala Asp Ala Leu Leu Asp Ser Ile Pro Met Val Ala Ile Thr
            100                 105                 110

Gly Gln Val Pro Arg Arg Met Ile Gly Thr Asp Ala Phe Gln Glu Thr
        115                 120                 125

Pro Ile Val Glu Val Thr Arg Ser Ile Thr Lys His Asn Tyr Leu Val
    130                 135                 140

Leu Asp Val Glu Asp Ile Pro Arg Val Ile Gln Glu Ala Phe Phe Leu
145                 150                 155                 160

Ala Ser Ser Gly Arg Pro Gly Pro Val Leu Val Asp Ile Pro Lys Asp
                165                 170                 175

Ile Gln Gln Gln Met Ala Val Pro Val Trp Asp Thr Pro Met Ser Leu
            180                 185                 190

Pro Gly Tyr Ile Ala Arg Leu Pro Lys Pro Ser Thr Glu Ser Leu
        195                 200                 205

Glu Gln Val Leu Arg Leu Val Gly Glu Ser Arg Pro Ile Leu Tyr
    210                 215                 220

Val Gly Gly Gly Cys Ala Ala Ser Gly Glu Glu Leu Arg Arg Phe Val
225                 230                 235                 240

Glu Leu Thr Gly Ile Pro Val Thr Thr Thr Leu Met Gly Leu Gly Asn
                245                 250                 255
```

Phe Pro Ser Asp Asp Pro Leu Ser Leu Arg Met Leu Gly Met His Gly
                260                 265                 270

Thr Val Tyr Ala Asn Tyr Ala Val Asp Lys Ala Asp Leu Leu Leu Ala
            275                 280                 285

Phe Gly Val Arg Phe Asp Asp Arg Val Thr Gly Lys Ile Glu Ala Phe
        290                 295                 300

Ala Ser Arg Ser Lys Ile Val His Ile Asp Ile Asp Pro Ala Glu Ile
305                 310                 315                 320

Gly Lys Asn Lys Gln Pro His Val Ser Ile Cys Ala Asp Val Lys Leu
                325                 330                 335

Ala Leu Gln Gly Leu Asn Ala Leu Leu Asn Gly Ser Lys Ala Gln Gln
            340                 345                 350

Gly Leu Asp Phe Gly Pro Trp His Lys Glu Leu Asp Gln Gln Lys Arg
        355                 360                 365

Glu Phe Pro Leu Gly Phe Lys Thr Phe Gly Glu Ala Ile Pro Pro Gln
370                 375                 380

Tyr Ala Ile Gln Val Leu Asp Glu Leu Thr Lys Gly Glu Ala Ile Ile
385                 390                 395                 400

Ala Thr Gly Val Gly Gln His Gln Met Trp Ala Ala Gln Tyr Tyr Thr
            405                 410                 415

Tyr Lys Arg Pro Arg Gln Trp Leu Ser Ser Ser Gly Leu Gly Ala Met
        420                 425                 430

Gly Phe Gly Leu Pro Ala Ala Ala Gly Ala Ala Val Ala Asn Pro Gly
        435                 440                 445

Val Thr Val Val Asp Ile Asp Gly Asp Gly Ser Phe Leu Met Asn Ile
        450                 455                 460

Gln Glu Leu Ala Leu Ile Arg Ile Glu Asn Leu Pro Val Lys Val Met
465                 470                 475                 480

Ile Leu Asn Asn Gln His Leu Gly Met Val Val Gln Trp Glu Asp Arg
                485                 490                 495

Phe Tyr Lys Ala Asn Arg Ala His Thr Tyr Leu Gly Asn Pro Glu Asn
            500                 505                 510

Glu Gly Glu Ile Tyr Pro Asp Phe Val Thr Ile Ala Lys Gly Phe Asn
        515                 520                 525

Val Pro Ala Val Arg Val Thr Lys Lys Ser Glu Val Thr Ala Ala Ile
        530                 535                 540

Lys Lys Met Leu Glu Thr Pro Gly Pro Tyr Leu Leu Asp Ile Ile Val
545                 550                 555                 560

Pro His Gln Glu His Val Leu Pro Met Ile Pro Ser Gly Gly Ala Phe
                565                 570                 575

Lys Asp Met Ile Met Glu Gly Asp Gly Arg Thr Ser Tyr
            580                 585

<210> SEQ ID NO 9
<211> LENGTH: 1756
<212> TYPE: DNA
<213> ORGANISM: Triticum durum

<400> SEQUENCE: 9
caccgcgctc cggccgtggg gcccctccga gccccgtaag ggcgccgaca tcctcgtcga     60
ggcgctggag cgctgcggca tcgtcgacgt cttcgcctac cctggcggcg cgtccatgga    120
gatccaccag gcgctgacgc gctcgccagt catcaccaac cacctcttcc gccacgagca    180
gggggaggcg ttcgcggcgt ccgggtacgc ccgcgcgtcc ggccgcgtcg gcgtctgcgt    240

-continued

```
cgccacctcc ggcccggggg ccaccaacct cgtctccgcg ctcgccgacg ctctcctcga    300
ctccatcccc atggtcgcca tcacgggcca ggtccccgc cgcatgatcg gcacggatgc     360
gttccaggag acgcccatcg tggaggtcac gcgctccatc accaagcaca actacctggt    420
ccttgacgtg gaggatatcc cccgcgtcat ccaggaagcc ttcttcctcg catcctctgg    480
ccgcccgggg ccggtgctgg ttgatatccc caaggacatc cagcagcaga tggctgtgcc    540
tgtctgggac acgccgatga gtttgccagg gtacatcgcc cgcctgccca agccaccatc    600
tactgaatcg cttgagcagg tcctgcgtct ggttggcgag tcacggcgcc caattctgta    660
tgttggtggt ggctgcgctg catctggtga ggagttgcgc cgctttgttg agctcactgg    720
gattccagtt acaactactc ttatgggcct tggcaacttc cccagtgacg acccactgtc    780
tctgcgcatg ctggggatgc atggcactgt gtatgcaaat tatgcagtag ataaggctga    840
cctgttgctt gcatttggtg tgcggtttga tgatcgtgtg accgggaaaa tcgaggcttt    900
tgcaagcagg tccaagattg tgcacattga cattgaccca gctgagattg caagaacaa     960
gcagccacat gtctccattt gtgcagatgt taagcttgct ttacaggggt tgaatgctct   1020
attaaatggg agcaaagcac aacagggtct ggattttggt ccatggcaca aggagttgga   1080
tcagcagaag agggagtttc ctctaggatt caagactttt ggtgaggcca tcccgccgca   1140
atatgctatc caggtactgg atgagctgac aaaaggggag gcgatcattg ccaccggtgt   1200
tgggcagcat cagatgtggg cggctcagta ttacacttac aagcggccac ggcagtggct   1260
gtcttcgtcc ggtttgggtg caatgggatt tgggttgcca gctgcagctg cgctgctgt    1320
ggccaaccca ggtgttacag ttgttgacat tgatggggat ggtagtttcc tcatgaacat   1380
tcaggagttg gcgttgatcc gtattgagaa cctcccagtg aaggtgatga tattgaacaa   1440
ccagcatctg ggaatggtgg tgcagtggga ggataggttt tacaaggcca accgggcgca   1500
cacataccct tggcaaccccag aaaatgaggg tgagatatat ccagattttg tgacgattgc   1560
taaaggattc aacgttccgg cagttcgtgt gacgaagaag agcgaagtca ctgcagcaat   1620
caagaagatg cttgagaccc agggccata cttgttggat atcattgtcc cgcatcagga   1680
gcacgtgctg cctatgatcc caagcggtgg tgcttttaag gacatgatca tggagggtga   1740
tggcaggacc tcgtac                                                   1756
```

<210> SEQ ID NO 10
<211> LENGTH: 585
<212> TYPE: PRT
<213> ORGANISM: Triticum durum

<400> SEQUENCE: 10

```
Thr Ala Leu Arg Pro Trp Gly Pro Ser Glu Pro Arg Lys Gly Ala Asp
1               5                   10                  15

Ile Leu Val Glu Ala Leu Glu Arg Cys Gly Ile Val Asp Val Phe Ala
            20                  25                  30

Tyr Pro Gly Gly Ala Ser Met Glu Ile His Gln Ala Leu Thr Arg Ser
        35                  40                  45

Pro Val Ile Thr Asn His Leu Phe Arg His Glu Gln Gly Glu Ala Phe
    50                  55                  60

Ala Ala Ser Gly Tyr Ala Arg Ala Ser Gly Arg Val Gly Val Cys Val
65                  70                  75                  80

Ala Thr Ser Gly Pro Gly Ala Thr Asn Leu Val Ser Ala Leu Ala Asp
                85                  90                  95

Ala Leu Leu Asp Ser Ile Pro Met Val Ala Ile Thr Gly Gln Val Pro
```

```
                100             105             110
Arg Arg Met Ile Gly Thr Asp Ala Phe Gln Glu Thr Pro Ile Val Glu
            115                 120                 125

Val Thr Arg Ser Ile Thr Lys His Asn Tyr Leu Val Leu Asp Val Glu
130                 135                 140

Asp Ile Pro Arg Val Ile Gln Glu Ala Phe Phe Leu Ala Ser Ser Gly
145                 150                 155                 160

Arg Pro Gly Pro Val Leu Val Asp Ile Pro Lys Asp Ile Gln Gln Gln
                165                 170                 175

Met Ala Val Pro Val Trp Asp Thr Pro Met Ser Leu Pro Gly Tyr Ile
            180                 185                 190

Ala Arg Leu Pro Lys Pro Pro Ser Thr Glu Ser Leu Glu Gln Val Leu
        195                 200                 205

Arg Leu Val Gly Glu Ser Arg Arg Pro Ile Leu Tyr Val Gly Gly Gly
    210                 215                 220

Cys Ala Ala Ser Gly Glu Glu Leu Arg Arg Phe Val Glu Leu Thr Gly
225                 230                 235                 240

Ile Pro Val Thr Thr Thr Leu Met Gly Leu Gly Asn Phe Pro Ser Asp
                245                 250                 255

Asp Pro Leu Ser Leu Arg Met Leu Gly Met His Gly Thr Val Tyr Ala
            260                 265                 270

Asn Tyr Ala Val Asp Lys Ala Asp Leu Leu Leu Ala Phe Gly Val Arg
        275                 280                 285

Phe Asp Asp Arg Val Thr Gly Lys Ile Glu Ala Phe Ala Ser Arg Ser
    290                 295                 300

Lys Ile Val His Ile Asp Ile Asp Pro Ala Glu Ile Gly Lys Asn Lys
305                 310                 315                 320

Gln Pro His Val Ser Ile Cys Ala Asp Val Lys Leu Ala Leu Gln Gly
                325                 330                 335

Leu Asn Ala Leu Leu Asn Gly Ser Lys Ala Gln Gln Gly Leu Asp Phe
            340                 345                 350

Gly Pro Trp His Lys Glu Leu Asp Gln Gln Lys Arg Glu Phe Pro Leu
        355                 360                 365

Gly Phe Lys Thr Phe Gly Glu Ala Ile Pro Pro Gln Tyr Ala Ile Gln
    370                 375                 380

Val Leu Asp Glu Leu Thr Lys Gly Glu Ala Ile Ile Ala Thr Gly Val
385                 390                 395                 400

Gly Gln His Gln Met Trp Ala Ala Gln Tyr Tyr Thr Tyr Lys Arg Pro
                405                 410                 415

Arg Gln Trp Leu Ser Ser Ser Gly Leu Gly Ala Met Gly Phe Gly Leu
            420                 425                 430

Pro Ala Ala Ala Gly Ala Ala Val Ala Asn Pro Gly Val Thr Val Val
        435                 440                 445

Asp Ile Asp Gly Asp Gly Ser Phe Leu Met Asn Ile Gln Glu Leu Ala
    450                 455                 460

Leu Ile Arg Ile Glu Asn Leu Pro Val Lys Val Met Ile Leu Asn Asn
465                 470                 475                 480

Gln His Leu Gly Met Val Val Gln Trp Glu Asp Arg Phe Tyr Lys Ala
                485                 490                 495

Asn Arg Ala His Thr Tyr Leu Gly Asn Pro Glu Asn Glu Gly Glu Ile
            500                 505                 510

Tyr Pro Asp Phe Val Thr Ile Ala Lys Gly Phe Asn Val Pro Ala Val
        515                 520                 525
```

```
Arg Val Thr Lys Lys Ser Glu Val Thr Ala Ala Ile Lys Lys Met Leu
        530                 535                 540

Glu Thr Pro Gly Pro Tyr Leu Leu Asp Ile Ile Val Pro His Gln Glu
545                 550                 555                 560

His Val Leu Pro Met Ile Pro Ser Gly Gly Ala Phe Lys Asp Met Ile
                565                 570                 575

Met Glu Gly Asp Gly Arg Thr Ser Tyr
            580                 585

<210> SEQ ID NO 11
<211> LENGTH: 1788
<212> TYPE: DNA
<213> ORGANISM: Triticum durum

<400> SEQUENCE: 11
tcccccgccg ccacctccgc cgcgcctccc gccaccgcgc tccggccgtg gggcccctcc      60
gagccccgta agggcgccga catcctcgtc gaggcgctgg agcgctgcgg catcgtcgac     120
gtcttcgcct accctggcgg cgcgtccatg gagatccacc aggcgctgac gcgctcgcca     180
gtcatcacca accacctctt ccgccacgag caggggagg cgttcgcggc gtccgggtac      240
gcccgcgcgt ccggccgcgt cggcgtctgc gtcgccacct ccggcccggg ggccaccaac     300
ctcgtctccg cgctcgccga cgctctcctc gactccatcc ccatggtcgc catcacgggc     360
caggtccccc gccgcatgat cggcacggat gcgttccagg agacgcccat cgtggaggtc     420
acgcgctcca tcaccaagca caactacctg gtccttgacg tggaggatat cccccgcgtc     480
atccaggaag ccttcttcct cgcatcctct ggccgcccgg ggccggtgct ggttgatatc     540
cccaaggaca tccagcagca gatggctgtg cctgtctggg acgccgat gagtttgcca       600 gggtacatcg cccgcctgcc caagccacca tctactgaat cgcttgagca ggtcctgcgt     660
ctggttggcg agtcacggcg cccaattctg tatgttggtg gtgctgcgc tgcatctggt      720 gaggagttgc gccgctttgt tgagctcact gggattccag ttacaactac tcttatgggc     780
cttggcaact tccccagtga cgacccactg tctctgcgca tgctgggat gcatggcact      840 gtgtatgcaa attatgcagt agataaggct gacctgttgc ttgcatttgg tgtgcggttt     900
gatgatcgtg tgaccgggaa aatcgaggct tttgcaagca ggtccaagat tgtgcacatt     960
gacattgacc cagctgagat tggcaagaac aagcagccac atgtctccat ttgtgcagat    1020
gttaagcttg ctttacaggg gttgaatgct ctattaaatg ggagcaaagc acaacagggt    1080
ctggattttg gtccatggca caaggagttg atcagcaga agagggagtt cctctagga     1140 ttcaagactt ttggtgaggc catcccgccg caatatgcta tccaggtact ggatgagctg    1200
acaaaagggg aggcgatcat tgccaccggt gttgggcagc atcagatgtg gcggctcag    1260 tattacactt acaagcggcc acggcagtgg ctgtcttcgt ccggtttggg tgcaatggga    1320
tttgggttgc cagctgcagc tggcgctgct gtggccaacc caggtgttac agttgttgac    1380
attgatgggg atggtagttt cctcatgaac attcaggagt tggcgttgat ccgtattgag    1440
aacctcccag tgaaggtgat gatattgaac aaccagcatc tgggaatggt ggtgcagtgg    1500
gaggataggt tttacaaggc caaccgggcg cacacatacc ttggcaaccc agaaaatgag    1560
ggtgagatat atccagattt tgtgacgatt gctaaggat tcaacgttcc ggcagttcgt     1620
gtgacgaaga gagcgaagt cactgcagca atcaagaaga tgcttgagac cccgggcca     1680 tacttgttgg atatcattgt cccgcatcag gagcacgtgc tgcctatgat cccaagcggt    1740
```
ggtgctttta aggacatgat catggagggt gatggcagga cctcgtac    1788

<210> SEQ ID NO 12
<211> LENGTH: 596
<212> TYPE: PRT
<213> ORGANISM: Triticum durum

<400> SEQUENCE: 12

```
Ser Pro Ala Ala Thr Ser Ala Ala Pro Pro Thr Ala Leu Arg Pro
1               5                   10                  15

Trp Gly Pro Ser Glu Pro Arg Lys Gly Ala Asp Ile Leu Val Glu Ala
            20                  25                  30

Leu Glu Arg Cys Gly Ile Val Asp Val Phe Ala Tyr Pro Gly Gly Ala
        35                  40                  45

Ser Met Glu Ile His Gln Ala Leu Thr Arg Ser Pro Val Ile Thr Asn
50                  55                  60

His Leu Phe Arg His Glu Gln Gly Glu Ala Phe Ala Ala Ser Gly Tyr
65                  70                  75                  80

Ala Arg Ala Ser Gly Arg Val Gly Val Cys Val Ala Thr Ser Gly Pro
                85                  90                  95

Gly Ala Thr Asn Leu Val Ser Ala Leu Ala Asp Ala Leu Leu Asp Ser
            100                 105                 110

Ile Pro Met Val Ala Ile Thr Gly Gln Val Pro Arg Arg Met Ile Gly
        115                 120                 125

Thr Asp Ala Phe Gln Glu Thr Pro Ile Val Glu Val Thr Arg Ser Ile
130                 135                 140

Thr Lys His Asn Tyr Leu Val Leu Asp Val Glu Asp Ile Pro Arg Val
145                 150                 155                 160

Ile Gln Glu Ala Phe Phe Leu Ala Ser Ser Gly Arg Pro Gly Pro Val
                165                 170                 175

Leu Val Asp Ile Pro Lys Asp Ile Gln Gln Gln Met Ala Val Pro Val
            180                 185                 190

Trp Asp Thr Pro Met Ser Leu Pro Gly Tyr Ile Ala Arg Leu Pro Lys
        195                 200                 205

Pro Pro Ser Thr Glu Ser Leu Glu Gln Val Leu Arg Leu Val Gly Glu
210                 215                 220

Ser Arg Arg Pro Ile Leu Tyr Val Gly Gly Gly Cys Ala Ala Ser Gly
225                 230                 235                 240

Glu Glu Leu Arg Arg Phe Val Glu Leu Thr Gly Ile Pro Val Thr Thr
                245                 250                 255

Thr Leu Met Gly Leu Gly Asn Phe Pro Ser Asp Asp Pro Leu Ser Leu
            260                 265                 270

Arg Met Leu Gly Met His Gly Thr Val Tyr Ala Asn Tyr Ala Val Asp
        275                 280                 285

Lys Ala Asp Leu Leu Leu Ala Phe Gly Val Arg Phe Asp Asp Arg Val
290                 295                 300

Thr Gly Lys Ile Glu Ala Phe Ala Ser Arg Ser Lys Ile Val His Ile
305                 310                 315                 320

Asp Ile Asp Pro Ala Glu Ile Gly Lys Asn Lys Gln Pro His Val Ser
                325                 330                 335

Ile Cys Ala Asp Val Lys Leu Ala Leu Gln Gly Leu Asn Ala Leu Leu
            340                 345                 350

Asn Gly Ser Lys Ala Gln Gln Gly Leu Asp Phe Gly Pro Trp His Lys
        355                 360                 365
```

```
Glu Leu Asp Gln Gln Lys Arg Glu Phe Pro Leu Gly Phe Lys Thr Phe
    370                 375                 380

Gly Glu Ala Ile Pro Pro Gln Tyr Ala Ile Gln Val Leu Asp Glu Leu
385                 390                 395                 400

Thr Lys Gly Glu Ala Ile Ile Ala Thr Gly Val Gly Gln His Gln Met
                405                 410                 415

Trp Ala Ala Gln Tyr Tyr Thr Tyr Lys Arg Pro Arg Gln Trp Leu Ser
                420                 425                 430

Ser Ser Gly Leu Gly Ala Met Gly Phe Gly Leu Pro Ala Ala Ala Gly
        435                 440                 445

Ala Ala Val Ala Asn Pro Gly Val Thr Val Val Asp Ile Asp Gly Asp
450                 455                 460

Gly Ser Phe Leu Met Asn Ile Gln Glu Leu Ala Leu Ile Arg Ile Glu
465                 470                 475                 480

Asn Leu Pro Val Lys Val Met Ile Leu Asn Asn Gln His Leu Gly Met
                485                 490                 495

Val Val Gln Trp Glu Asp Arg Phe Tyr Lys Ala Asn Arg Ala His Thr
            500                 505                 510

Tyr Leu Gly Asn Pro Glu Asn Glu Gly Glu Ile Tyr Pro Asp Phe Val
        515                 520                 525

Thr Ile Ala Lys Gly Phe Asn Val Pro Ala Val Arg Val Thr Lys Lys
    530                 535                 540

Ser Glu Val Thr Ala Ala Ile Lys Lys Met Leu Glu Thr Pro Gly Pro
545                 550                 555                 560

Tyr Leu Leu Asp Ile Ile Val Pro His Gln Glu His Val Leu Pro Met
                565                 570                 575

Ile Pro Ser Gly Gly Ala Phe Lys Asp Met Ile Met Glu Gly Asp Gly
            580                 585                 590

Arg Thr Ser Tyr
        595

<210> SEQ ID NO 13
<211> LENGTH: 1788
<212> TYPE: DNA
<213> ORGANISM: Triticum durum

<400> SEQUENCE: 13
tcccccgccg ccacctccgc cgcgcccccc gccaccgcgc tccggccctg gggcccgtcc      60
gagccccgca agggcgccga catcctcgtc gaggcgctcg agcgctgcgg catcgtcgac     120
gtattcgcct accccggcgg cgcgtccatg gagatccacc aggcgctgac gcgctcgccc     180
gtcatcacca accacctctt ccgccacgag caggggagg cgttcgcggc gtccggctac     240
gcccgcgcgt ccgccgcgt cggcgtctgc gtcgccacct ccggcccggg ggccaccaac     300
ctcgtctccg cgctcgctga cgccctcctc gactccatcc ccatggtcgc catcacgggc     360
caggtccccc gccgcatgat cggcacggac gcgttccagg agacgcccat agtggaggtc     420
acgcgctcca tcaccaagca caactacctg gtccttgacg tggaggatat ccccgcgtc     480 atccaggaag ccttcttcct cgcgtcctct ggccgcccgg ggccggtgct ggttgatatc     540
cccaaggata tccagcagca gatggccgtg cctatctggg acacgccgat gagtttgcca     600
gggtacatcg cccgcctgcc caagccacca tctactgaat cgcttgagca ggtcctgcgt     660
ctggttggcg agtcacggcg cccaattctg tatgttggtg gtggctgcgc tgcatccggc     720
gaggagttgc gccgctttgt tgagctcact gggattccgg ttacaactac tctgatgggc     780
```

| | |
|---|---|
| cttggcaact tccccagcga cgacccactg tctctgcgca tgcttgggat gcatggcact | 840 |
| gtgtatgcaa attatgcagt cgataaggct gacctgttgc ttgcatttgg tgtgcggttt | 900 |
| gatgatcgcg tgactgggaa aatcgaggcc tttgcaagca ggtccaagat tgtgcacatt | 960 |
| gacattgacc cagctgagat tggcaagaac aagcagccac atgtctccat ttgtgcagat | 1020 |
| gttaagcttg ctttacaggg gttgaatgct ctattaaatg ggagcaaagc acaacagggt | 1080 |
| ctggattttg gtccatggca caaggagttg atcagcaga agagggagtt tcctctagga | 1140 |
| ttcaagactt ttggcgaggc catcccgccg caatatgcta tccaggtact ggatgagctg | 1200 |
| acaaaagggg aggcgatcat tgctactggt gttgggcagc accagatgtg gcggctcag | 1260 |
| tattacactt acaagcggcc acggcagtgg ctgtcttcgt ctggtttggg ggcaatggga | 1320 |
| tttgggttac cagctgcagc tggcgctgct gtggccaacc caggtgttac agttgttgac | 1380 |
| attgatggag atggtagttt cctcatgaac attcaggagt tggcattgat ccgtattgag | 1440 |
| aacctccctg tgaaggtgat gatattgaac aaccagcatc tgggaatggt ggtgcaatgg | 1500 |
| gaggataggt tttacaaggc caatcgggcg cacacatacc ttggcaaccc agaaaatgag | 1560 |
| agtgagatat atccagattt tgtgacgatt gctaaaggat tcaacgttcc ggcagttcgt | 1620 |
| gtgacgaaga gagcgaagt cactgcagca atcaagaaga tgcttgagac cccagggcca | 1680 |
| tacttgttgg atatcatcgt cccgcatcag gagcacgtgc tgcctatgat cccaagcggt | 1740 |
| ggtgctttca aggacatgat catggagggt gatggcagga cctcgtac | 1788 |

<210> SEQ ID NO 14
<211> LENGTH: 1788
<212> TYPE: DNA
<213> ORGANISM: Triticum durum

<400> SEQUENCE: 14

| | |
|---|---|
| tcccccgccg ccacctccgc cgcgcctccc gccaccgcgc tccggccgtg gggcccctcc | 60 |
| gagccccgta agggcgccga catcctcgtc gaggcgctgg agcgctgcgg catcgtcgac | 120 |
| gtcttcgcct accctggcgg cgcgtccatg gagatccacc aggcgctgac gcgctcgcca | 180 |
| gtcatcacca accacctctt ccgccacgag caggggggag cgttcgcggc gtccgggtac | 240 |
| gcccgcgcgt ccggccgcgt cggcgtctgc gtcgccacct ccgcccgggg gccaccaac | 300 |
| ctcgtctccg cgctcgccga cgctctcctc gactccatcc ccatggtcgc catcacgggc | 360 |
| caggtccccc gccgcatgat cggcacggat gcgttccagg agacgcccat cgtggaggtc | 420 |
| acgcgctcca tcaccaagca caactacctg gtccttgacg tggaggatat cccccgcgtc | 480 |
| atccaggaag ccttcttcct cgcatcctct ggccgcccgg ggccggtgct ggttgatatc | 540 |
| cccaaggaca tccagcagca gatggctgtg cctgtctggg acacgccgat gagtttgcca | 600 |
| gggtacatcg cccgcctgcc caagccacca tctactgaat cgcttgagca ggtcctgcgt | 660 |
| ctggttggcg agtcacggcg cccaattctg tatgttggtg gtggctgcgc tgcatctggt | 720 |
| gaggagttgc gccgctttgt tgagctcact gggattccag ttacaactac tcttatgggc | 780 |
| cttggcaact tccccagtga cgacccactg tctctgcgca tgctggggat gcatggcact | 840 |
| gtgtatgcaa attatgcagt agataaggct gacctgttgc ttgcatttgg tgtgcggttt | 900 |
| gatgatcgtg tgaccgggaa aatcgaggct tttgcaagca ggtccaagat tgtgcacatt | 960 |
| gacattgacc cagctgagat tggcaagaac aagcagccac atgtctccat ttgtgcagat | 1020 |
| gttaagcttg ctttacaggg gttgaatgct ctattaaatg ggagcaaagc acaacagggt | 1080 |
| ctggattttg gtccatggca caaggagttg atcagcaga agagggagtt tcctctagga | 1140 |

| | |
|---|---|
| ttcaagactt ttggtgaggc catcccgccg caatatgcta tccaggtact ggatgagctg | 1200 |
| acaaaagggg aggcgatcat tgccaccggt gttgggcagc atcagatgtg gcggctcag | 1260 |
| tattacactt acaagcggcc acggcagtgg ctgtcttcgt ccggtttggg tgcaatggga | 1320 |
| tttggggttgc cagctgcagc tggcgctgct gtggccaacc caggtgttac agttgttgac | 1380 |
| attgatgggg atggtagttt cctcatgaac attcaggagt tggcgttgat ccgtattgag | 1440 |
| aacctcccag tgaaggtgat gatattgaac aaccagcatc tgggaatggt ggtgcagtgg | 1500 |
| gaggataggt tttacaaggc aaccgggcg cacacatacc ttggcaaccc agaaaatgag | 1560 |
| ggtgagatat atccagattt tgtgacgatt gctaaaggat tcaacgttcc ggcagttcgt | 1620 |
| gtgacgaaga agagcgaagt cactgcagca atcaagaaga tgcttgagac cccagggcca | 1680 |
| tacttgttgg atatcattgt cccgcatcag gagcacgtgc tgcctatgat cccaagcggt | 1740 |
| ggtgctttta aggacatgat catggagggt gatggcagga cctcgtac | 1788 |

<210> SEQ ID NO 15
<211> LENGTH: 1788
<212> TYPE: DNA
<213> ORGANISM: Triticum durum

<400> SEQUENCE: 15

| | |
|---|---|
| tcccccgccg ccacctccgc cgcgcccccc gccaccgcgc tccggccctg gggcccgtcc | 60 |
| gagccccgca agggcgccga catcctcgtc gaggcgctcg agcgctgcgg catcgtcgac | 120 |
| gtattcgcct accccggcgg cgcgtccatg gagatccacc aggcgctgac gcgctcgccc | 180 |
| gtcatcacca accacctctt ccgccacgag caggggagg cgttcgcggc gtccggctac | 240 |
| gcccgcgcgt ccggccgcgt cggcgtctgc gtcgccacct ccggcccggg ggccaccaac | 300 |
| ctcgtctccg cgctcgctga cgccctcctc gactccatcc ccatggtcgc catcacgggc | 360 |
| caggtccccc gccgcatgat cggcacggac gcgttccagg agacgcccat agtggaggtc | 420 |
| acgcgctcca tcaccaagca caactacctg gtccttgacg tggaggatat ccccccgcgtc | 480 |
| atccaggaag ccttcttcct cgcgtcctct ggccgcccgg ggccggtgct ggttgatatc | 540 |
| cccaaggata tccagcagca gatggccgtg cctatctggg acacgccgat gagtttgcca | 600 |
| gggtacatcg cccgcctgcc caagccacca tctactgaat cgcttgagca ggtcctgcgt | 660 |
| ctggttggcg agtcacggcg cccaattctg tatgttggtg gtggctgcgc tgcatccggc | 720 |
| gaggagttgc gccgctttgt tgagctcact gggattccgg ttacaactac tctgatgggc | 780 |
| cttggcaact tccccagcga cgaccccactg tctctgcgca tgcttgggat gcatggcact | 840 |
| gtgtatgcaa attatgcagt cgataaggct gacctgttgc ttgcatttgg tgtgcggttt | 900 |
| gatgatcgcg tgactgggaa aatcgaggcc tttgcaagca ggtccaagat tgtgcacatt | 960 |
| gacattgacc cagctgagat tggcaagaac aagcagccac atgtctccat ttgtgcagat | 1020 |
| gttaagcttg ctttacaggg gttgaatgct ctattaaatg ggagcaaagc acaacagggt | 1080 |
| ctggattttg gtccatggca caaggagttg gatcagcaga gagggagtt tcctctagga | 1140 |
| ttcaagactt ttggcgaggc catcccgccg caatatgcta tccaggtact ggatgagctg | 1200 |
| acaaaagggg aggcgatcat tgctactggt gttgggcagc accagatgtg gcggctcag | 1260 |
| tattacactt acaagcggcc acggcagtgg ctgtcttcgt ctggtttggg ggcaatggga | 1320 |
| tttggggttac cagctgcagc tggcgctgct gtggccaacc caggtgttac agttgttgac | 1380 |
| attgatggag atggtagttt cctcatgaac attcaggagt tggcattgat ccgtattgag | 1440 |

```
aacctccctg tgaaggtgat gatattgaac aaccagcatc tgggaatggt ggtgcaatgg      1500
gaggataggt tttacaaggc caatcgggcg cacacatacc ttggcaaccc agaaaatgag      1560
agtgagatat atccagattt tgtgacgatt gctaaaggat tcaacgttcc ggcagttcgt      1620
gtgacgaaga agagcgaagt cactgcagca atcaagaaga tgcttgagac cccagggcca      1680
tacttgttgg atatcatcgt cccgcatcag gagcacgtgc tgcctatgat cccaagcggt      1740
ggtgctttca aggacatgat catggagggt gatggcagga cctcgtac                   1788

<210> SEQ ID NO 16
<211> LENGTH: 1788
<212> TYPE: DNA
<213> ORGANISM: Triticum durum

<400> SEQUENCE: 16
tcccccgccg ccacctccgc cgcgcctccc gccaccgcgc tccggccgtg gggcccctcc        60 gagcccgta agggcgccga catcctcgtc gaggcgctgg agcgctgcgg catcgtcgac       120
gtcttcgcct accctggcgg cgcgtccatg gagatccacc aggcgctgac gcgctcgcca       180
gtcatcacca accacctctt ccgccacgag caggggagg cgttcgcggc gtccgggtac       240
gcccgcgcgt ccgccgcgt cggcgtctgc gtcgccacct ccggcccggg ggccaccaac       300
ctcgtctccg cgctcgccga cgctctcctc gactccatcc ccatggtcgc catcacgggc       360
caggtccccc gccgcatgat cggcacggat gcgttccagg agacgccat cgtggaggtc       420 acgcgctcca tcaccaagca caactacctg gtccttgacg tggaggatat ccccgcgtc       480 atccaggaag ccttcttcct cgcatcctct ggccgcccgg ggccggtgct ggttgatatc       540
cccaaggaca tccagcagca gatggctgtg cctgtctggg acacgccgat gagtttgcca       600
gggtacatcg cccgcctgcc caagccacca tctactgaat cgcttgagca ggtcctgcgt       660
ctggttggcg agtcacggcg cccaattctg tatgttggtg gtggctgcgc tgcatctggt       720
gaggagttgc gccgctttgt tgagctcact gggattccag ttacaactac tcttatgggc       780
cttggcaact tccccagtga cgacccactg tctctgcgca tgctggggat gcatggcact       840
gtgtatgcaa attatgcagt agataaggct gacctgttgc ttgcatttgg tgtgcggttt       900
gatgatcgtg tgaccgggaa aatcgaggct tttgcaagca ggtccaagat tgtgcacatt       960
gacattgacc cagctgagat tggcaagaac aagcagccac atgtctccat tgtgcagat      1020 gttaagcttg ctttacaggg gttgaatgct ctattaaatg ggagcaaagc acaacagggt      1080
ctggattttg gtccatggca caaggagttg atcagcaga agaggagtt tcctctagga      1140 ttcaagactt ttggtgaggc catcccgccg caatatgcta tccaggtact ggatgagctg      1200
acaaaagggg aggcgatcat tgccaccggt gttgggcagc atcagatgtg gcggctcag      1260 tattacactt acaagcggcc acggcagtgg ctgtcttcgt ccggtttggg tgcaatggga      1320
tttgggttgc cagctgcagc tggcgctgct gtggccaacc caggtgttac agttgttgac      1380
attgatgggg atggtagttt cctcatgaac attcaggagt tggcgttgat ccgtattgag      1440
aacctcccag tgaaggtgat gatattgaac aaccagcatc tgggaatggt ggtgcagtgg      1500
gaggataggt tttacaaggc caaccgggcg cacacatacc ttggcaaccc agaaaatgag      1560
ggtgagatat atccagattt tgtgacgatt gctaaaggat tcaacgttcc ggcagttcgt      1620
gtgacgaaga agagcgaagt cactgcagca atcaagaaga tgcttgagac cccagggcca      1680
tacttgttgg atatcattgt cccgcatcag gagcacgtgc tgcctatgat cccaagcggt      1740
ggtgctttta aggacatgat catggagggt gatggcagga cctcgtac                   1788
```

<210> SEQ ID NO 17
<211> LENGTH: 1788
<212> TYPE: DNA
<213> ORGANISM: Triticum durum

<400> SEQUENCE: 17

```
tcccccgccg ccacctccgc cgcgccccccc gccaccgcgc tccggccctg gggcccgtcc      60
gagccccgca agggcgccga catcctcgtc gaggcgctcg agcgctgcgg catcgtcgac     120
gtattcgcct accccggcgg cgcgtccatg gagatccacc aggcgctgac gcgctcgccc     180
gtcatcacca accacctctt ccgccacgag caggggagg cgttcgcggc gtccggctac      240
gcccgcgcgt ccggccgcgt cggcgtctgc gtcgccacct ccggcccggg ggccaccaac     300
ctcgtctccg cgctcgctga cgccctcctc gactccatcc ccatggtcgc catcacgggc     360
caggtccccc gccgcatgat cggcacggac gcgttccagg agacgcccat agtggaggtc     420
acgcgctcca tcaccaagca caactacctg gtccttgacg tggaggatat cccccgcgtc     480
atccaggaag ccttcttcct cgcgtcctct ggccgcccgg ggccggtgct ggttgatatc     540
cccaaggata tccagcagca gatggccgtg cctatctggg acacgccgat gagtttgcca     600
gggtacatcg cccgcctgcc caagccacca tctactgaat cgcttgagca ggtcctgcgt     660
ctggttggcg agtcacggcg cccaattctg tatgttggtg gtggctgcgc tgcatccggc     720
gaggagttgc gccgctttgt tgagctcact gggattccgg ttacaactac tctgatgggc     780
cttggcaact tccccagcga cgacccactg tctctgcgca tgcttgggat gcatggcact     840
gtgtatgcaa attatgcagt cgataaggct gacctgttgc ttgcatttgg tgtgcggttt     900
gatgatcgcg tgactgggaa aatcgaggcc tttgcaagca ggtccaagat tgtgcacatt     960
gacattgacc cagctgagat tggcaagaac aagcagccac atgtctccat tgtgcagat    1020
gttaagcttg cttttacaggg gttgaatgct ctattaaatg ggagcaaagc acaacagggt    1080
ctggattttg gtccatggca caaggagttg gatcagcaga gagggagtt tcctctagga    1140
ttcaagactt ttggcgaggc catcccgccg caatatgcta tccaggtact ggatgagctg    1200
acaaaagggg aggcgatcat tgctactggt gttgggcagc accagatgtg ggcggctcag    1260
tattacactt acaagcggcc acggcagtgg ctgtcttcgt ctggtttggg ggcaatggga    1320
tttgggttac cagctgcagc tggcgctgct gtggccaacc caggtgttac agttgttgac    1380
attgatggag atggtagttt cctcatgaac attcaggagt tggcattgat ccgtattgag    1440
aacctccctg tgaaggtgat gatattgaac aaccagcatc tgggaatggt ggtgcaatgg    1500
gaggataggt tttacaaggc caatcgggcg cacacatacc ttggcaaccc agaaaatgag    1560
agtgagatat atccagattt tgtgacgatt gctaaaggat tcaacgttcc ggcagttcgt    1620
gtgacgaaga agagcgaagt cactgcagca atcaagaaga tgcttgagac cccagggcca    1680
tacttgttgg atatcatcgt cccgcatcag gagcacgtgc tgcctatgat cccaagcggt    1740
ggtgctttca aggacatgat catggagggt gatggcagga cctcgtac                 1788
```

<210> SEQ ID NO 18
<211> LENGTH: 596
<212> TYPE: PRT
<213> ORGANISM: Triticum durum

<400> SEQUENCE: 18

```
Ser Pro Ala Ala Thr Ser Ala Ala Pro Pro Ala Thr Ala Leu Arg Pro
1               5                  10                  15
```

```
Trp Gly Pro Ser Glu Pro Arg Lys Gly Ala Asp Ile Leu Val Glu Ala
            20                  25                  30

Leu Glu Arg Cys Gly Ile Val Asp Val Phe Ala Tyr Pro Gly Gly Ala
        35                  40                  45

Ser Met Glu Ile His Gln Ala Leu Thr Arg Ser Pro Val Ile Thr Asn
 50                  55                  60

His Leu Phe Arg His Glu Gln Gly Ala Phe Ala Ala Ser Gly Tyr
 65                  70                  75                  80

Ala Arg Ala Ser Gly Arg Val Gly Val Cys Val Ala Thr Ser Gly Pro
                85                  90                  95

Gly Ala Thr Asn Leu Val Ser Ala Leu Ala Asp Ala Leu Leu Asp Ser
                100                 105                 110

Ile Pro Met Val Ala Ile Thr Gly Gln Val Pro Arg Arg Met Ile Gly
            115                 120                 125

Thr Asp Ala Phe Gln Glu Thr Pro Ile Val Glu Val Thr Arg Ser Ile
130                 135                 140

Thr Lys His Asn Tyr Leu Val Leu Asp Val Glu Asp Ile Pro Arg Val
145                 150                 155                 160

Ile Gln Glu Ala Phe Phe Leu Ala Ser Ser Gly Arg Pro Gly Pro Val
                165                 170                 175

Leu Val Asp Ile Pro Lys Asp Ile Gln Gln Gln Met Ala Val Pro Ile
            180                 185                 190

Trp Asp Thr Pro Met Ser Leu Pro Gly Tyr Ile Ala Arg Leu Pro Lys
        195                 200                 205

Pro Pro Ser Thr Glu Ser Leu Glu Gln Val Leu Arg Leu Val Gly Glu
        210                 215                 220

Ser Arg Arg Pro Ile Leu Tyr Val Gly Gly Gly Cys Ala Ala Ser Gly
225                 230                 235                 240

Glu Glu Leu Arg Arg Phe Val Glu Leu Thr Gly Ile Pro Val Thr Thr
                245                 250                 255

Thr Leu Met Gly Leu Gly Asn Phe Pro Ser Asp Asp Pro Leu Ser Leu
            260                 265                 270

Arg Met Leu Gly Met His Gly Thr Val Tyr Ala Asn Tyr Ala Val Asp
        275                 280                 285

Lys Ala Asp Leu Leu Leu Ala Phe Gly Val Arg Phe Asp Asp Arg Val
290                 295                 300

Thr Gly Lys Ile Glu Ala Phe Ala Ser Arg Ser Lys Ile Val His Ile
305                 310                 315                 320

Asp Ile Asp Pro Ala Glu Ile Gly Lys Asn Lys Gln Pro His Val Ser
                325                 330                 335

Ile Cys Ala Asp Val Lys Leu Ala Leu Gln Gly Leu Asn Ala Leu Leu
            340                 345                 350

Asn Gly Ser Lys Ala Gln Gln Gly Leu Asp Phe Gly Pro Trp His Lys
        355                 360                 365

Glu Leu Asp Gln Gln Lys Arg Glu Phe Pro Leu Gly Phe Lys Thr Phe
        370                 375                 380

Gly Glu Ala Ile Pro Pro Gln Tyr Ala Ile Gln Val Leu Asp Glu Leu
385                 390                 395                 400

Thr Lys Gly Glu Ala Ile Ile Ala Thr Gly Val Gly Gln His Gln Met
                405                 410                 415

Trp Ala Ala Gln Tyr Tyr Thr Tyr Lys Arg Pro Arg Gln Trp Leu Ser
            420                 425                 430
```

Ser Ser Gly Leu Gly Ala Met Gly Phe Gly Leu Pro Ala Ala Ala Gly
        435                 440                 445

Ala Ala Val Ala Asn Pro Gly Val Thr Val Val Asp Ile Asp Gly Asp
450                 455                 460

Gly Ser Phe Leu Met Asn Ile Gln Glu Leu Ala Leu Ile Arg Ile Glu
465                 470                 475                 480

Asn Leu Pro Val Lys Val Met Ile Leu Asn Asn Gln His Leu Gly Met
                485                 490                 495

Val Val Gln Trp Glu Asp Arg Phe Tyr Lys Ala Asn Arg Ala His Thr
            500                 505                 510

Tyr Leu Gly Asn Pro Glu Asn Glu Ser Glu Ile Tyr Pro Asp Phe Val
        515                 520                 525

Thr Ile Ala Lys Gly Phe Asn Val Pro Ala Val Arg Val Thr Lys Lys
530                 535                 540

Ser Glu Val Thr Ala Ala Ile Lys Lys Met Leu Glu Thr Pro Gly Pro
545                 550                 555                 560

Tyr Leu Leu Asp Ile Ile Val Pro His Gln His Val Leu Pro Met
                565                 570                 575

Ile Pro Ser Gly Gly Ala Phe Lys Asp Met Ile Met Glu Gly Asp Gly
            580                 585                 590

Arg Thr Ser Tyr
        595

<210> SEQ ID NO 19
<211> LENGTH: 1788
<212> TYPE: DNA
<213> ORGANISM: Artificial Sequence
<220> FEATURE:
<223> OTHER INFORMATION: Consensus sequence

<400> SEQUENCE: 19
tcccccgccg ccacctccgc cgcgcctccc gccaccgcgc tccggccgtg gggcccctcc      60
gagccccgta agggcgccga catcctcgtc gaggcgctgg agcgctgcgg catcgtcgac     120
gtcttcgcct accctggcgg cgcgtccatg gagatccacc aggcgctgac gcgctcgcca     180
gtcatcacca accacctctt ccgccacgag caggggagg cgttcgcggc gtccgggtac     240
gcccgcgcgt ccggccgcgt cggcgtctgc gtcgccacct ccggcccggg ggccaccaac     300
ctcgtctccg cgctcgccga cgctctcctc gactccatcc ccatggtcgc catcacgggc     360
caggtccccc gccgcatgat cggcacggat gcgttccagg agacgcccat cgtggaggtc     420
acgcgctcca tcaccaagca caactacctg gtccttgacg tggaggatat ccccgcgtc     480 atccaggaag ccttcttcct cgcatcctct ggccgcccgg ggccggtgct ggttgatatc     540
cccaaggaca tccagcagca gatggctgtg cctgtctggg acacgccgat gagtttgcca     600
gggtacatcg cccgcctgcc caagccacca tctactgaat cgcttgagca ggtcctgcgt     660
ctggttggcg agtcacggcg cccaattctg tatgttggtg gtggctgcgc tgcatctggt     720
gaggagttgc gccgctttgt tgagctcact gggattccag ttacaactac tcttatgggc     780
cttggcaact tccccagtga cgacccactg tctctgcgca tgctggggat gcatggcact     840
gtgtatgcaa attatgcagt agataaggct gacctgttgc ttgcatttgg tgtgcggttt     900
gatgatcgtg tgaccgggaa aatcgaggct tttgcaagca ggtccaagat tgtgcacatt     960
gacattgacc cagctgagat tggcaagaac aagcagccac atgtctccat tgtgcagat    1020 gttaagcttg ctttacaggg gttgaatgct ctattaaatg ggagcaaagc acaacagggt    1080

```
ctggattttg gtccatggca caaggagttg gatcagcaga agagggagtt tcctctagga    1140
ttcaagactt ttggtgaggc catcccgccg caatatgcta tccaggtact ggatgagctg    1200
acaaaagggg aggcgatcat tgccaccggt gttgggcagc atcagatgtg gcggctcag    1260 tattacactt acaagcggcc acggcagtgg ctgtcttcgt ccggtttggg tgcaatggga    1320
tttgggttgc cagctgcagc tggcgctgct gtggccaacc caggtgttac agttgttgac    1380
attgatgggg atggtagttt cctcatgaac attcaggagt tggcgttgat ccgtattgag    1440
aacctcccag tgaaggtgat gatattgaac aaccagcatc tgggaatggt ggtgcagtgg    1500
gaggataggt tttacaaggc caaccgggcg cacacatacc ttggcaaccc agaaaatgag    1560
ggtgagatat atccagattt tgtgacgatt gctaaaggat tcaacgttcc ggcagttcgt    1620
gtgacgaaga agagcgaagt cactgcagca atcaagaaga tgcttgagac cccagggcca    1680
tacttgttgg atatcattgt cccgcatcag gagcacgtgc tgcctatgat cccaagcggt    1740 ggtgcttta aggacatgat catggagggt gatggcagga cctcgtac    1788
```

<210> SEQ ID NO 20
<211> LENGTH: 596
<212> TYPE: PRT
<213> ORGANISM: Artificial Sequence
<220> FEATURE:
<223> OTHER INFORMATION: Consensus sequence
<220> FEATURE:
<221> NAME/KEY: MOD_RES
<222> LOCATION: (579)
<223> OTHER INFORMATION: Variable amino acid

<400> SEQUENCE: 20

```
Ser Pro Ala Ala Thr Ser Ala Ala Pro Pro Ala Thr Ala Leu Arg Pro
1               5                   10                  15

Trp Gly Pro Ser Glu Pro Arg Lys Gly Ala Asp Ile Leu Val Glu Ala
            20                  25                  30

Leu Glu Arg Cys Gly Ile Val Asp Val Phe Ala Tyr Pro Gly Gly Ala
        35                  40                  45

Ser Met Glu Ile His Gln Ala Leu Thr Arg Ser Pro Val Ile Thr Asn
    50                  55                  60

His Leu Phe Arg His Glu Gln Gly Glu Ala Phe Ala Ala Ser Gly Tyr
65                  70                  75                  80

Ala Arg Ala Ser Gly Arg Val Gly Val Cys Val Ala Thr Ser Gly Pro
                85                  90                  95

Gly Ala Thr Asn Leu Val Ser Ala Leu Ala Asp Ala Leu Leu Asp Ser
            100                 105                 110

Ile Pro Met Val Ala Ile Thr Gly Gln Val Pro Arg Arg Met Ile Gly
        115                 120                 125

Thr Asp Ala Phe Gln Glu Thr Pro Ile Val Glu Val Thr Arg Ser Ile
    130                 135                 140

Thr Lys His Asn Tyr Leu Val Leu Asp Val Glu Asp Ile Pro Arg Val
145                 150                 155                 160

Ile Gln Glu Ala Phe Phe Leu Ala Ser Ser Gly Arg Pro Gly Pro Val
                165                 170                 175

Leu Val Asp Ile Pro Lys Asp Ile Gln Gln Gln Met Ala Val Pro Val
            180                 185                 190

Trp Asp Thr Pro Met Ser Leu Pro Gly Tyr Ile Ala Arg Leu Pro Lys
        195                 200                 205

Pro Pro Ser Thr Glu Ser Leu Glu Gln Val Leu Arg Leu Val Gly Glu
    210                 215                 220
```

Ser Arg Arg Pro Ile Leu Tyr Val Gly Gly Cys Ala Ala Ser Gly
225                 230                 235                 240

Glu Glu Leu Arg Arg Phe Val Glu Leu Thr Gly Ile Pro Val Thr Thr
            245                 250                 255

Thr Leu Met Gly Leu Gly Asn Phe Pro Ser Asp Asp Pro Leu Ser Leu
        260                 265                 270

Arg Met Leu Gly Met His Gly Thr Val Tyr Ala Asn Tyr Ala Val Asp
        275                 280                 285

Lys Ala Asp Leu Leu Leu Ala Phe Gly Val Arg Phe Asp Asp Arg Val
        290                 295                 300

Thr Gly Lys Ile Glu Ala Phe Ala Ser Arg Ser Lys Ile Val His Ile
305                 310                 315                 320

Asp Ile Asp Pro Ala Glu Ile Gly Lys Asn Lys Gln Pro His Val Ser
                325                 330                 335

Ile Cys Ala Asp Val Lys Leu Ala Leu Gln Gly Leu Asn Ala Leu Leu
            340                 345                 350

Asn Gly Ser Lys Ala Gln Gln Gly Leu Asp Phe Gly Pro Trp His Lys
        355                 360                 365

Glu Leu Asp Gln Gln Lys Arg Glu Phe Pro Leu Gly Phe Lys Thr Phe
370                 375                 380

Gly Glu Ala Ile Pro Pro Gln Tyr Ala Ile Gln Val Leu Asp Glu Leu
385                 390                 395                 400

Thr Lys Gly Glu Ala Ile Ile Ala Thr Gly Val Gly Gln His Gln Met
                405                 410                 415

Trp Ala Ala Gln Tyr Tyr Thr Tyr Lys Arg Pro Arg Gln Trp Leu Ser
            420                 425                 430

Ser Ser Gly Leu Gly Ala Met Gly Phe Gly Leu Pro Ala Ala Ala Gly
        435                 440                 445

Ala Ala Val Ala Asn Pro Gly Val Thr Val Val Asp Ile Asp Gly Asp
        450                 455                 460

Gly Ser Phe Leu Met Asn Ile Gln Glu Leu Ala Leu Ile Arg Ile Glu
465                 470                 475                 480

Asn Leu Pro Val Lys Val Met Ile Leu Asn Asn Gln His Leu Gly Met
                485                 490                 495

Val Val Gln Trp Glu Asp Arg Phe Tyr Lys Ala Asn Arg Ala His Thr
            500                 505                 510

Tyr Leu Gly Asn Pro Glu Asn Glu Gly Glu Ile Tyr Pro Asp Phe Val
        515                 520                 525

Thr Ile Ala Lys Gly Phe Asn Val Pro Ala Val Arg Val Thr Lys Lys
        530                 535                 540

Ser Glu Val Thr Ala Ala Ile Lys Lys Met Leu Glu Thr Pro Gly Pro
545                 550                 555                 560

Tyr Leu Leu Asp Ile Ile Val Pro His Gln Glu His Val Leu Pro Met
                565                 570                 575

Ile Pro Xaa Gly Gly Ala Phe Lys Asp Met Ile Met Glu Gly Asp Gly
            580                 585                 590

Arg Thr Ser Tyr
        595

<210> SEQ ID NO 21
<211> LENGTH: 1788
<212> TYPE: DNA
<213> ORGANISM: Artificial Sequence
<220> FEATURE:

<223> OTHER INFORMATION: Consensus sequence

<400> SEQUENCE: 21

```
tccccgccg  ccacctccgc  cgcgcccccc  gccaccgcgc  tccggccctg  gggcccgtcc     60
gagccccgca aggcgccga  catcctcgtc  gaggcgctcg  agcgctgcgg  catcgtcgac    120
gtattcgcct accccggcgg cgcgtccatg gagatccacc  aggcgctgac  gcgctcgccc    180
gtcatcacca accacctctt  ccgccacgag  caggggagg  cgttcgcggc  gtccggctac    240
gcccgcgcgt ccggccgcgt cggcgtctgc gtcgccacct  ccgcccgggg ggccaccaac    300
ctcgtctccg cgctcgctga cgccctcctc  gactccatcc  ccatggtcgc  catcacgggc    360
caggtccccc  gccgcatgat  cggcacggac  gcgttccagg  agacgcccat  agtggaggtc    420
acgcgctcca  tcaccaagca  caactacctg  gtccttgacg  tggaggatat  ccccgcgtc     480
atccaggaag  ccttcttcct  cgcgtcctct  ggccgcccgg  ggccggtgct  ggttgatatc    540
cccaaggata  tccagcagca  gatggccgtg  cctatctggg  acacgccgat  gagtttgcca    600
gggtacatcg  cccgcctgcc  caagccacca  tctactgaat  cgcttgagca  ggtcctgcgt    660
ctggttggcg  agtcacggcg  cccaattctg  tatgttggtg  gtggctgcgc  tgcatccggc    720
gaggagttgc  gccgctttgt  tgagctcact  gggattccgg  ttacaactac  tctgatgggc    780
cttggcaact  tccccagcga  cgacccactg  tctctgcgca  tgcttgggat  gcatggcact    840
gtgtatgcaa  attatgcagt  cgataaggct  gacctgttgc  ttgcatttgg  tgtgcggttt    900
gatgatcgcg  tgactgggaa  aatcgaggcc  tttgcaagca  ggtccaagat  tgtgcacatt    960
gacattgacc  cagctgagat  tggcaagaac  aagcagccac  atgtctccat  ttgtgcagat   1020
gttaagcttg  ctttacaggg  gttgaatgct  ctattaaatg  ggagcaaagc  acaacagggt   1080
ctggattttg  gtccatggca  caaggagttg  atcagcaga   agagggagtt tcctctagga    1140
ttcaagactt  ttggcgaggc  catcccgccg  caatatgcta  tccaggtact  ggatgagctg   1200
acaaaagggg  aggcgatcat  tgctactggt  gttgggcagc  accagatgtg  gcggctcag    1260
tattacactt  acaagcggcc  acggcagtgg  ctgtcttcgt  ctggtttggg  ggcaatggga   1320
tttgggttac  cagctgcagc  tggcgctgct  gtggccaacc  caggtgttac  agttgttgac   1380
attgatggag  atggtagttt  cctcatgaac  attcaggagt  tggcattgat  ccgtattgag   1440
aacctccctg  tgaaggtgat  gatattgaac  aaccagcatc  tgggaatggt  ggtgcaatgg   1500
gaggataggt  tttacaaggc  caatcgggcg  cacacatacc  ttggcaaccc  agaaaatgag   1560
agtgagatat  atccagattt  tgtgacgatt  gctaaaggat  tcaacgttcc  ggcagttcgt   1620
gtgacgaaga  agagcgaagt  cactgcagca  atcaagaaga  tgcttgagac  cccagggcca   1680
tacttgttgg  atatcatcgt  cccgcatcag  gagcacgtgc  tgcctatgat  cccaagcggt   1740
ggtgctttca  aggacatgat  catggagggt  gatggcagga  cctcgtac              1788
```

<210> SEQ ID NO 22
<211> LENGTH: 574
<212> TYPE: PRT
<213> ORGANISM: Artificial Sequence
<220> FEATURE:
<223> OTHER INFORMATION: Consensus sequence
<220> FEATURE:
<221> NAME/KEY: MOD_RES
<222> LOCATION: (557)
<223> OTHER INFORMATION: Variable amino acid

<400> SEQUENCE: 22

Arg Lys Gly Ala Asp Ile Leu Val Glu Ala Leu Glu Arg Cys Gly Ile

```
1               5                   10                  15
Val Asp Val Phe Ala Tyr Pro Gly Gly Thr Ser Met Glu Ile His Gln
                20                  25                  30
Ala Leu Thr Arg Ser Pro Val Ile Thr Asn His Leu Phe Arg His Glu
                35                  40                  45
Gln Gly Glu Ala Phe Ala Ala Ser Gly Tyr Ala Arg Ala Ser Gly Arg
                50                  55                  60
Val Gly Val Cys Val Ala Thr Ser Gly Pro Gly Ala Thr Asn Leu Val
65                  70                  75                  80
Ser Ala Leu Ala Asp Ala Leu Leu Asp Ser Ile Pro Met Val Ala Ile
                85                  90                  95
Thr Gly Gln Val Pro Arg Arg Met Ile Gly Thr Asp Ala Phe Gln Glu
                100                 105                 110
Thr Pro Ile Val Glu Val Thr Arg Ser Ile Thr Lys His Asn Tyr Leu
                115                 120                 125
Val Leu Asp Val Glu Asp Ile Pro Arg Val Ile Gln Glu Ala Phe Phe
                130                 135                 140
Leu Ala Ser Ser Gly Arg Pro Gly Pro Val Leu Val Asp Ile Pro Lys
145                 150                 155                 160
Asp Ile Gln Gln Gln Met Ala Val Pro Ile Trp Asp Thr Pro Met Ser
                165                 170                 175
Leu Pro Gly Tyr Ile Ala Arg Leu Pro Lys Pro Pro Ser Thr Glu Ser
                180                 185                 190
Leu Glu Gln Val Leu Arg Leu Val Gly Glu Ser Arg Arg Pro Ile Leu
                195                 200                 205
Tyr Val Gly Gly Gly Cys Ala Ala Ser Gly Glu Glu Leu Arg Arg Phe
                210                 215                 220
Val Glu Leu Thr Gly Ile Pro Val Thr Thr Thr Leu Met Gly Leu Gly
225                 230                 235                 240
Asn Phe Pro Ser Asp Asp Pro Leu Ser Leu Arg Met Leu Gly Met His
                245                 250                 255
Gly Thr Val Tyr Ala Asn Tyr Ala Val Asp Lys Ala Asp Leu Leu Leu
                260                 265                 270
Ala Phe Gly Val Arg Phe Asp Asp Arg Val Thr Gly Lys Ile Glu Ala
                275                 280                 285
Phe Ala Ser Arg Ser Lys Ile Val His Ile Asp Ile Asp Pro Ala Glu
                290                 295                 300
Ile Gly Lys Asn Lys Gln Pro His Val Ser Ile Cys Ala Asp Val Lys
305                 310                 315                 320
Leu Ala Leu Gln Gly Leu Asn Ala Leu Leu Asn Gly Ser Lys Ala Gln
                325                 330                 335
Gln Gly Leu Asp Phe Gly Pro Trp His Lys Glu Leu Asp Gln Gln Lys
                340                 345                 350
Arg Glu Phe Pro Leu Gly Phe Lys Thr Phe Gly Glu Ala Ile Pro Pro
                355                 360                 365
Gln Tyr Ala Ile Gln Val Leu Asp Glu Leu Thr Lys Gly Glu Ala Ile
                370                 375                 380
Ile Ala Thr Gly Val Gly Gln His Gln Met Trp Ala Ala Gln Tyr Tyr
385                 390                 395                 400
Thr Tyr Lys Arg Pro Arg Gln Trp Leu Ser Ser Gly Leu Gly Ala
                405                 410                 415
Met Gly Phe Gly Leu Pro Ala Ala Ala Gly Ala Ala Val Ala Asn Pro
                420                 425                 430
```

```
Gly Val Thr Val Val Asp Ile Asp Gly Asp Gly Ser Phe Leu Met Asn
            435                 440                 445

Ile Gln Glu Leu Ala Leu Ile Arg Ile Glu Asn Leu Pro Val Lys Val
450                 455                 460

Met Ile Leu Asn Asn Gln His Leu Gly Met Val Val Gln Trp Glu Asp
465                 470                 475                 480

Arg Phe Tyr Lys Ala Asn Arg Ala His Thr Tyr Leu Gly Asn Pro Glu
                485                 490                 495

Asn Glu Ser Glu Ile Tyr Pro Asp Phe Val Thr Ile Ala Lys Gly Phe
            500                 505                 510

Asn Val Pro Ala Val Arg Val Thr Lys Lys Ser Glu Val Thr Ala Ala
            515                 520                 525

Ile Lys Lys Met Leu Glu Thr Pro Gly Pro Tyr Leu Leu Asp Ile Ile
530                 535                 540

Val Pro His Gln Glu His Val Leu Pro Met Ile Pro Xaa Gly Gly Ala
545                 550                 555                 560

Phe Lys Asp Met Ile Met Glu Gly Asp Gly Arg Thr Ser Tyr
                565                 570

<210> SEQ ID NO 23
<211> LENGTH: 1710
<212> TYPE: DNA
<213> ORGANISM: Triticum durum

<400> SEQUENCE: 23
gacatcctcg tcgaggcgct cgagcgctgc ggcatcgtcg acgtattcgc ctaccccggc      60
ggcacgtcca tggagatcca ccaggcgctg acgcgctcgc ccgtcatcac caaccacctc     120
ttccgccacg agcaggggga ggcgttcgcg gcgtccggct acgcccgcgc gtccggccgc     180
gtcggcgtct cgtcgccac  ctccggcccg ggggccacca acctcgtctc cgcgctcgct     240
gacgccctcc tcgactccat ccccatggtc gccatcacgg gccaggtccc ccgccgcatg     300
atcggcacgg acgcgttcca ggagacgccc atagtggagg tcacgcgctc catcaccaag     360
cacaactacc tggtccttga cgtggaggat atccccccgcg tcatccagga agccttcttc     420
ctcgcgtcct ctggccgccc ggggccggtg ctggttgata tccccaagga tatccagcag     480
cagatggccg tgcctatctg ggacacgccg atgagttttgc cagggtacat cgcccgcctg     540
cccaagccac catctactga atcgcttgag caggtcctgc gtctggttgg cgagtcacgg     600
cgcccaattc tgtatgttgg tggtggctgc gctgcatccg gcgaggagtt cgccgcttt      660 gttgagctca ctgggattcc ggttacaact actctgatgg gccttggcaa cttccccagc     720
gacgacccac tgtctctgcg catgcttggg atgcatggca ctgtgtatgc aaattatgca     780
gtcgataagg ctgacctgtt gcttgcattt ggtgtgcggt ttgatgatcg cgtgactggg     840
aaaatcgagg cctttgcaag caggtccaag attgtgcaca ttgacattga cccagctgag     900
attggcaaga caagcagcc  acatgtctcc atttgtgcag atgttaagct tgctttacag     960
gggttgaatg ctctattaaa tgggagcaaa gcacaacagg gtctggattt tggtccatgg    1020
cacaaggagt tggatcagca aagagggag  tttcctctag gattcaagac tttttggcgag    1080 gccatcccgc cgcaatatgc tatccaggta ctggatgagc tgacaaaagg ggaggcgatc    1140
attgctactg gtgttgggca gcaccagatg tgggcggctc agtattacac ttacaagcgg    1200
ccacggcagt ggctgtcttc gtctggttg  ggggcaatgg gatttgggtt accagctgca    1260
gctggcgctg ctgtggccaa cccaggtgtt acagttgttg acattgatgg agatggtagt    1320
```

```
ttcctcatga acattcagga gttggcattg atccgtattg agaacctccc tgtgaaggtg    1380
atgatattga acaaccagca tctgggaatg gtggtgcaat gggaggatag gttttacaag    1440
gccaatcggg cgcacacata ccttggcaac ccagaaaatg agagtgagat atatccagat    1500
tttgtgacga ttgctaaagg attcaacgtt ccggcagttc gtgtgacgaa gaagagcgaa    1560
gtcactgcag caatcaagaa gatgcttgag accccagggc atacttgtt ggatatcatc     1620 gtcccgcatc aggagcacgt gctgcctatg atcccaagcg gtggtgcttt caaggacatg    1680
atcatggagg gtgatggcag gacctcgtac                                     1710

<210> SEQ ID NO 24
<211> LENGTH: 570
<212> TYPE: PRT
<213> ORGANISM: Triticum durum

<400> SEQUENCE: 24
```

Asp Ile Leu Val Glu Ala Leu Glu Arg Cys Gly Ile Val Asp Val Phe
 1               5                  10                  15

Ala Tyr Pro Gly Gly Thr Ser Met Glu Ile His Gln Ala Leu Thr Arg
            20                  25                  30

Ser Pro Val Ile Thr Asn His Leu Phe Arg His Glu Gln Gly Glu Ala
        35                  40                  45

Phe Ala Ala Ser Gly Tyr Ala Arg Ala Ser Gly Arg Val Gly Val Cys
    50                  55                  60

Val Ala Thr Ser Gly Pro Gly Ala Thr Asn Leu Val Ser Ala Leu Ala
65                  70                  75                  80

Asp Ala Leu Leu Asp Ser Ile Pro Met Val Ala Ile Thr Gly Gln Val
                85                  90                  95

Pro Arg Arg Met Ile Gly Thr Asp Ala Phe Gln Glu Thr Pro Ile Val
            100                 105                 110

Glu Val Thr Arg Ser Ile Thr Lys His Asn Tyr Leu Val Leu Asp Val
        115                 120                 125

Glu Asp Ile Pro Arg Val Ile Gln Glu Ala Phe Phe Leu Ala Ser Ser
    130                 135                 140

Gly Arg Pro Gly Pro Val Leu Val Asp Ile Pro Lys Asp Ile Gln Gln
145                 150                 155                 160

Gln Met Ala Val Pro Ile Trp Asp Thr Pro Met Ser Leu Pro Gly Tyr
                165                 170                 175

Ile Ala Arg Leu Pro Lys Pro Pro Ser Thr Glu Ser Leu Glu Gln Val
            180                 185                 190

Leu Arg Leu Val Gly Glu Ser Arg Arg Pro Ile Leu Tyr Val Gly Gly
        195                 200                 205

Gly Cys Ala Ala Ser Gly Glu Glu Leu Arg Arg Phe Val Glu Leu Thr
    210                 215                 220

Gly Ile Pro Val Thr Thr Thr Leu Met Gly Leu Gly Asn Phe Pro Ser
225                 230                 235                 240

Asp Asp Pro Leu Ser Leu Arg Met Leu Gly Met His Gly Thr Val Tyr
                245                 250                 255

Ala Asn Tyr Ala Val Asp Lys Ala Asp Leu Leu Leu Ala Phe Gly Val
            260                 265                 270

Arg Phe Asp Asp Arg Val Thr Gly Lys Ile Glu Ala Phe Ala Ser Arg
        275                 280                 285

Ser Lys Ile Val His Ile Asp Ile Asp Pro Ala Glu Ile Gly Lys Asn
    290                 295                 300

```
Lys Gln Pro His Val Ser Ile Cys Ala Asp Val Lys Leu Ala Leu Gln
305                 310                 315                 320

Gly Leu Asn Ala Leu Asn Gly Ser Lys Ala Gln Gln Gly Leu Asp
            325                 330                 335

Phe Gly Pro Trp His Lys Glu Leu Asp Gln Gln Lys Arg Glu Phe Pro
            340                 345                 350

Leu Gly Phe Lys Thr Phe Gly Glu Ala Ile Pro Pro Gln Tyr Ala Ile
            355                 360                 365

Gln Val Leu Asp Glu Leu Thr Lys Gly Glu Ala Ile Ile Ala Thr Gly
            370                 375                 380

Val Gly Gln His Gln Met Trp Ala Ala Gln Tyr Tyr Thr Tyr Lys Arg
385                 390                 395                 400

Pro Arg Gln Trp Leu Ser Ser Ser Gly Leu Gly Ala Met Gly Phe Gly
            405                 410                 415

Leu Pro Ala Ala Ala Gly Ala Ala Val Ala Asn Pro Gly Val Thr Val
            420                 425                 430

Val Asp Ile Asp Gly Asp Gly Ser Phe Leu Met Asn Ile Gln Glu Leu
            435                 440                 445

Ala Leu Ile Arg Ile Glu Asn Leu Pro Val Lys Val Met Ile Leu Asn
450                 455                 460

Asn Gln His Leu Gly Met Val Val Gln Trp Glu Asp Arg Phe Tyr Lys
465                 470                 475                 480

Ala Asn Arg Ala His Thr Tyr Leu Gly Asn Pro Glu Asn Glu Ser Glu
            485                 490                 495

Ile Tyr Pro Asp Phe Val Thr Ile Ala Lys Gly Phe Asn Val Pro Ala
            500                 505                 510

Val Arg Val Thr Lys Lys Ser Glu Val Thr Ala Ala Ile Lys Lys Met
            515                 520                 525

Leu Glu Thr Pro Gly Pro Tyr Leu Leu Asp Ile Ile Val Pro His Gln
            530                 535                 540

Glu His Val Leu Pro Met Ile Pro Ser Gly Gly Ala Phe Lys Asp Met
545                 550                 555                 560

Ile Met Glu Gly Asp Gly Arg Thr Ser Tyr
            565                 570

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved domain peptide

<400> SEQUENCE: 25

Ala Ile Thr Gly Gln Val Pro Arg Arg Met Ile Gly Thr
1               5                   10

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:
      Illustrative conserved domain peptide

<400> SEQUENCE: 26

Gln Trp Glu Asp
1
```

```
<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence:
      Illustrative conserved domain peptide

<400> SEQUENCE: 27

Val Phe Ala Tyr Pro Gly Gly Ala Ser Met Glu Ile His Gln Ala Leu
1               5                   10                  15

Thr Arg Ser

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:
      Illustrative conserved domain peptide

<400> SEQUENCE: 28

Ala Phe Gln Glu Thr Pro
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence:
      Illustrative conserved domain peptide

<400> SEQUENCE: 29

Ile Pro Ser Gly Gly
1               5
```